(12) United States Patent
Brierton et al.

(10) Patent No.: US 6,361,518 B1
(45) Date of Patent: Mar. 26, 2002

(54) EXTRACORPOREAL BLOOD PROCESSING METHODS AND APPARATUS

(75) Inventors: Mark J. Brierton, Littleton; Victor D. Dolecek, Englewood; Leon E. Bilodeau, Littleton; Russell Hempstead, Boulder, all of CO (US)

(73) Assignee: Gambro Inc., Lakewood, CO (US)

( * ) Notice: Subject to any disclaimer, the term of this patent is extended or adjusted under 35 U.S.C. 154(b) by 0 days.

(21) Appl. No.: 09/067,209

(22) Filed: Apr. 28, 1998

Related U.S. Application Data

(62) Division of application No. 08/486,217, filed on Jun. 7, 1995, now Pat. No. 5,795,317.

(51) Int. Cl.[7] .................. A61M 37/00; B01D 35/00; B01D 33/15; B04B 3/00
(52) U.S. Cl. ............... 604/6.01; 604/6.11; 604/5.01; 210/782; 210/88
(58) Field of Search ................ 604/4–6, 4.01, 604/5.01, 5.02–5.04, 6.01–6.05, 6.1, 6.15, 45; 494/18, 42, 45, 17, 36, 85, 21, 43, 37; 210/645–47, 739, 741, 767, 787, 781–82, 790, 252, 256, 258, 259–61, 254; 422/44

(56) References Cited

U.S. PATENT DOCUMENTS

| | | | |
|---|---|---|---|
| 3,946,731 A | 3/1976 | Lichtenstein | 128/214 |
| 4,114,802 A | 9/1978 | Brown | 233/26 |
| 4,263,808 A | 4/1981 | Bellotti et al. | 73/714 |
| 4,303,193 A | 12/1981 | Latham, Jr. | 233/23 A |
| 4,370,983 A | 2/1983 | Lichtenstein | 128/630 |
| 4,379,452 A | 4/1983 | DeVries | 604/6 |
| 4,425,112 A | 1/1984 | Ito | 494/18 |
| 4,436,620 A | 3/1984 | Bellotti et al. | 210/90 |

(List continued on next page.)

FOREIGN PATENT DOCUMENTS

| | | |
|---|---|---|
| DE | 26 36 290 | 2/1978 |
| EP | 0 096 217 | 5/1983 |
| EP | 0 165 751 | 6/1985 |
| EP | 0 214 803 | 8/1986 |
| FR | 2 390 173 | 12/1978 |
| GB | 2 176 717 A | 1/1987 |
| WO | WO 88/01880 | 3/1988 |
| WO | WO 88/05691 | 8/1988 |
| WO | WO 93/12888 | 7/1993 |

OTHER PUBLICATIONS

"Haemonetics Mobile Collection System Owner's Operating and Maintenance Manual: Chapter 1–Introduction to the Haemonetics Mobile Collection System", Haemonetics Corporation, Braintree, Massachussetts, Dec. 1, 1991, Rev. B.

(List continued on next page.)

Primary Examiner—Jeffrey R. Jastrzab
Assistant Examiner—Patricia Bianco
(74) Attorney, Agent, or Firm—Edna M. O'Connor; Peter B. Scull; Laura M. Butterfield

(57) ABSTRACT

An extracorporeal blood processing system is disclosed which includes a variety of novel components and which may be operated in accordance with a variety of novel methodologies. For instance, the system includes a graphical operator interface which directs the operator through various aspects of the apheresis procedure. Moreover, the system also includes a variety of features relating to loading a blood processing vessel into a blood processing channel and removing the same after completion of the procedure. Furthermore, the system also includes a variety of features relating to utilizing a blood priming of at least portions of the apheresis system in preparation for the procedure. In addition, the system includes a variety of features enhancing the performance of the apheresis system, including the interrelationship between the blood processing vessel and the blood processing vessel and the utilization of high packing factors for the procedure.

12 Claims, 51 Drawing Sheets

U.S. PATENT DOCUMENTS

| | | |
|---|---|---|
| 4,479,760 A | 10/1984 | Bilstad et al. ............... 417/395 |
| 4,479,761 A | 10/1984 | Bilstad et al. ............... 417/395 |
| 4,526,515 A | 7/1985 | DeVries ........................ 417/63 |
| 4,626,243 A | 12/1986 | Singh et al. ................. 604/141 |
| 4,637,813 A | 1/1987 | DeVries .......................... 604/6 |
| 4,661,246 A | 4/1987 | Ash ............................ 210/87 |
| 4,798,090 A | 1/1989 | Heath et al. .................. 73/715 |
| 4,834,890 A | 5/1989 | Brown et al. ................ 210/739 |
| 4,851,126 A | 7/1989 | Schoendorfer .............. 210/651 |
| 4,897,184 A | 1/1990 | Shouldice et al. ............. 210/87 |
| 4,968,295 A | 11/1990 | Nenmann ....................... 604/6 |
| 5,078,671 A | 1/1992 | Dennehey et al. ............ 494/27 |
| 5,120,303 A | 6/1992 | Hombrouckx ................. 604/4 |
| 5,174,894 A | 12/1992 | Ohsawa et al. ............... 210/86 |
| 5,178,603 A | 1/1993 | Prince ........................... 604/6 |
| 5,217,426 A | 6/1993 | Bacehowski et al. ......... 494/45 |
| 5,267,956 A | 12/1993 | Beuchat ........................ 604/30 |
| 5,273,517 A | 12/1993 | Barone et al. ................ 494/37 |
| 5,316,667 A | 5/1994 | Brown et al. ................. 210/85 |
| 5,360,542 A | 11/1994 | Williamson, IV et al. .. 210/232 |
| 5,362,291 A | 11/1994 | Williamson, IV ............ 494/18 |
| 5,370,802 A | 12/1994 | Brown ....................... 210/782 |
| 5,441,636 A | 8/1995 | Chevallet et al. ........... 210/232 |
| 5,496,265 A | 3/1996 | Langley et al. ................ 604/5 |
| 5,514,069 A * | 5/1996 | Brown et al. ................. 494/18 |
| 5,906,570 A * | 5/1999 | Langley et al. ............... 494/45 |

OTHER PUBLICATIONS

"Haemonetics Mobile Collection System Owner's Operating and Maintenance Manual: Chapter 2–Equipment Description", Haemonetics Corporation, Braintree, Massachussetts, Dec. 1, 1991, Rev. B.

"Haemonetics Mobile Collection System Owner's Operating and Maintenance Manual: Chapter 3–Bowls", Haemonetics Corporation, Braintree, Massachussetts, Dec. 1, 1991, Rev. B.

"Haemonetics Mobile Collection System Owner's Operating and Maintenance Manual: Chapter 4–Disposables", Haemonetics Corporation, Braintree, Massachussetts, Dec. 1, 1991, Rev. B.

"Haemonetics Mobile Collection System Owner's Operating and Maintenance Manual: Chapter 5–Platelet Protocol", Haemonetics Corporation, Braintree, Massachussetts, Dec. 1, 1991, Rev. B.

"Haemonetics Mobile Collection System Owner's Operating and Maintenance Manual: Chapter 6–Platelet/Plasma (PLP) Protocol", Haemonetics Corporation, Braintree, Massachussetts, Dec. 1, 1991, Rev. B.

"CS–3000 Plus Parameter Changes—CS–3000 Plus Blood Cell Separator Operator's Manual: Chapter 1–Description", Baxter Healthcare Corporation, Deerfield, Illinois.

"CS–3000 Plus Parameter Changes—CS–3000 Plus Blood Cell Separator Operator's Manual: Chapter 8–Information for Use", Baxter Healthcare Corporation, Deerfield, Illinois.

"CS–3000 Plus Parameter Changes—CS–3000 Plus Blood Cell Separator Operator's Manual: Chapter 9–Run Procedures", Baxter Healthcare Corporation, Deerfield, Illinois.

"CS–3000 Plus Parameter Changes—CS–3000 Plus Blood Cell Separator Operator's Manual: Table–12–1. Auto Prime Troubleshooting Matrix—Table 12–2. Run and Reinfuse Troubleshooting Matrix", Baxter Healthcare Corporation, Deerfield, Illinois.

"Operating Instructions as 104 Blood Cell Separator", pp. 0–4 through 0–6, Fresenius AG, Medical Engineering Department.

"Operating Instructions as 104 Blood Cell Separator: Chapter 2–Brief Operating Instructions", Fresenius AG, Medical Engineering Department.

"Operating Instructions as 104 Blood Cell Separator: Chapter 3–Saffen & Alarm Circuits Operating Instructions", Fresenius AG, Medical Engineering Department.

"Cobe Spectra Apheresis System Operator's Manual: Table of Contents", Cobe BCT, Inc., Blood Component Technology, BCT Marketing Dept., Lakewood, Colorado.

"Cobe Spectra Apheresis System Operator's Manual: Section 1–Introduction", Cobe BCT, Inc., Blood Component Technology, BCT Marketing Dept., Lakewood, Colorado.

"Cobe Spectra Apheresis System Operator's Manual: Section 3A–ELP Dual–Needle Operation", pp. 3A–8 through 3A–11, Cobe BCT, Inc., Blood Component Technology, BCT Marketing Dept., Lakewood, Colorado.

"Cobe Spectra Apheresis System Operator's Manual: Section 4A–Platelet Dual–Needle Operation and Section 4B–Platelet Single–Needle Operation", Cobe BCT, Inc., Blood Component Technology, BCT Marketing Dept., Lakewood, Colorado.

* cited by examiner

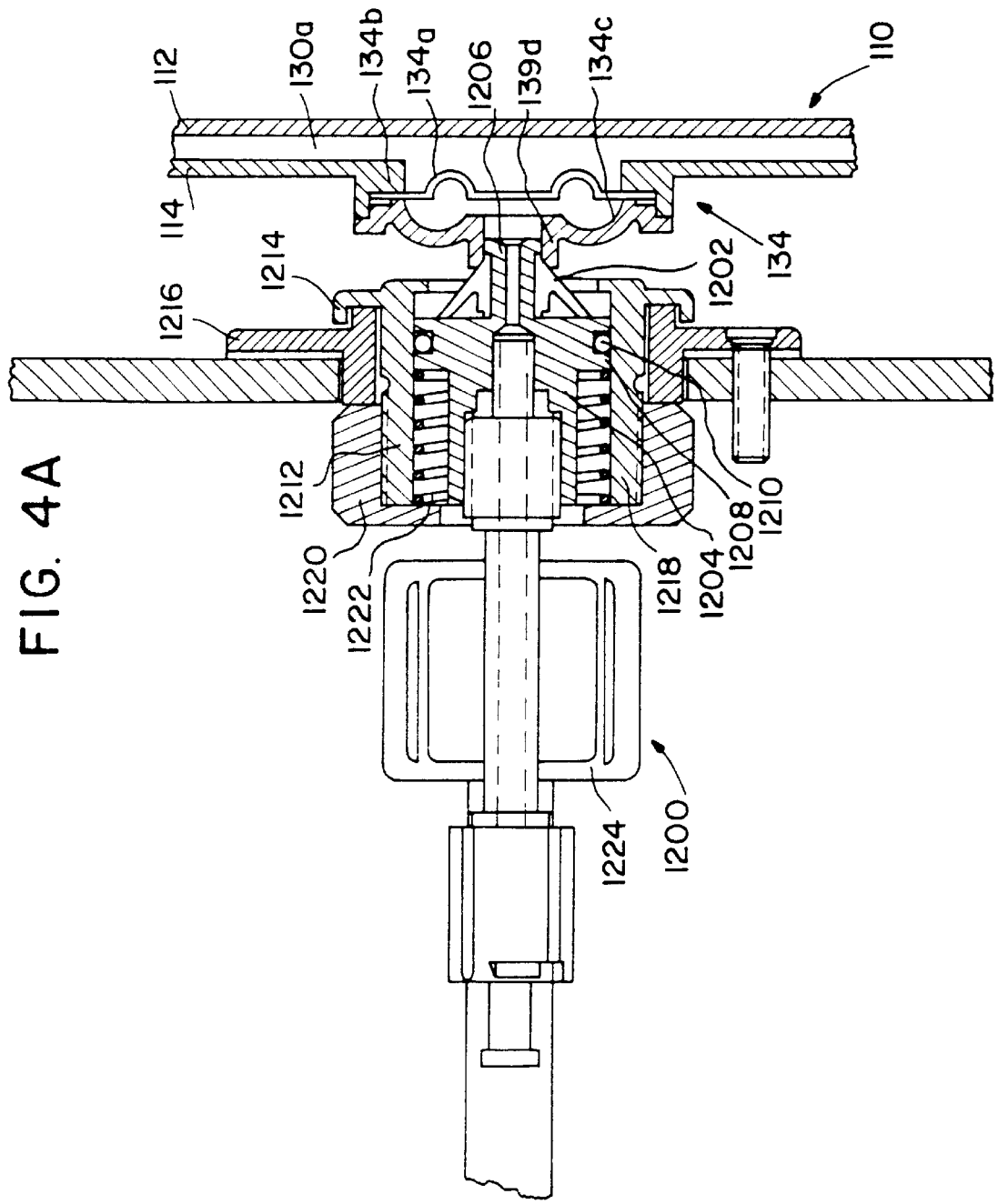

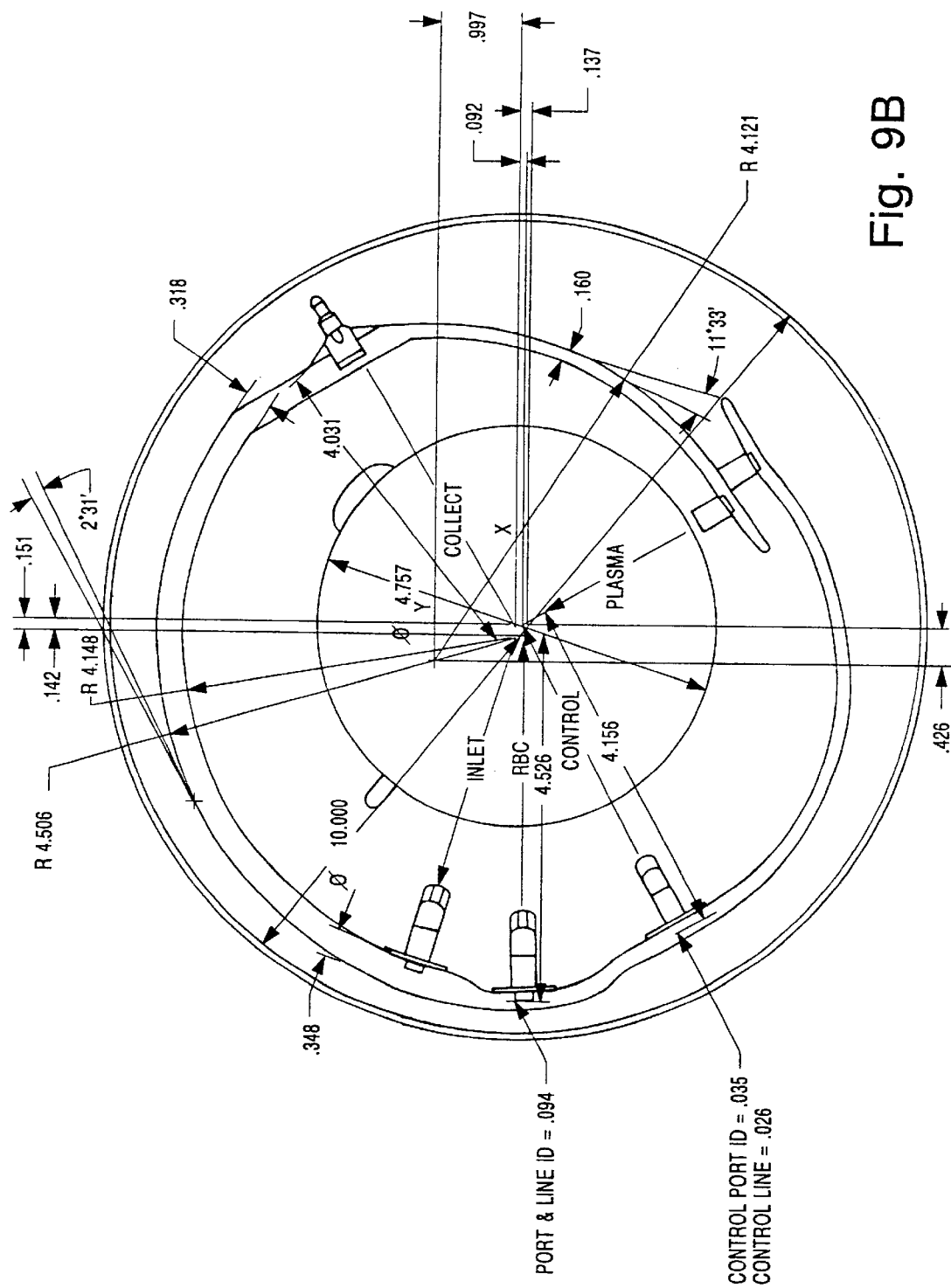

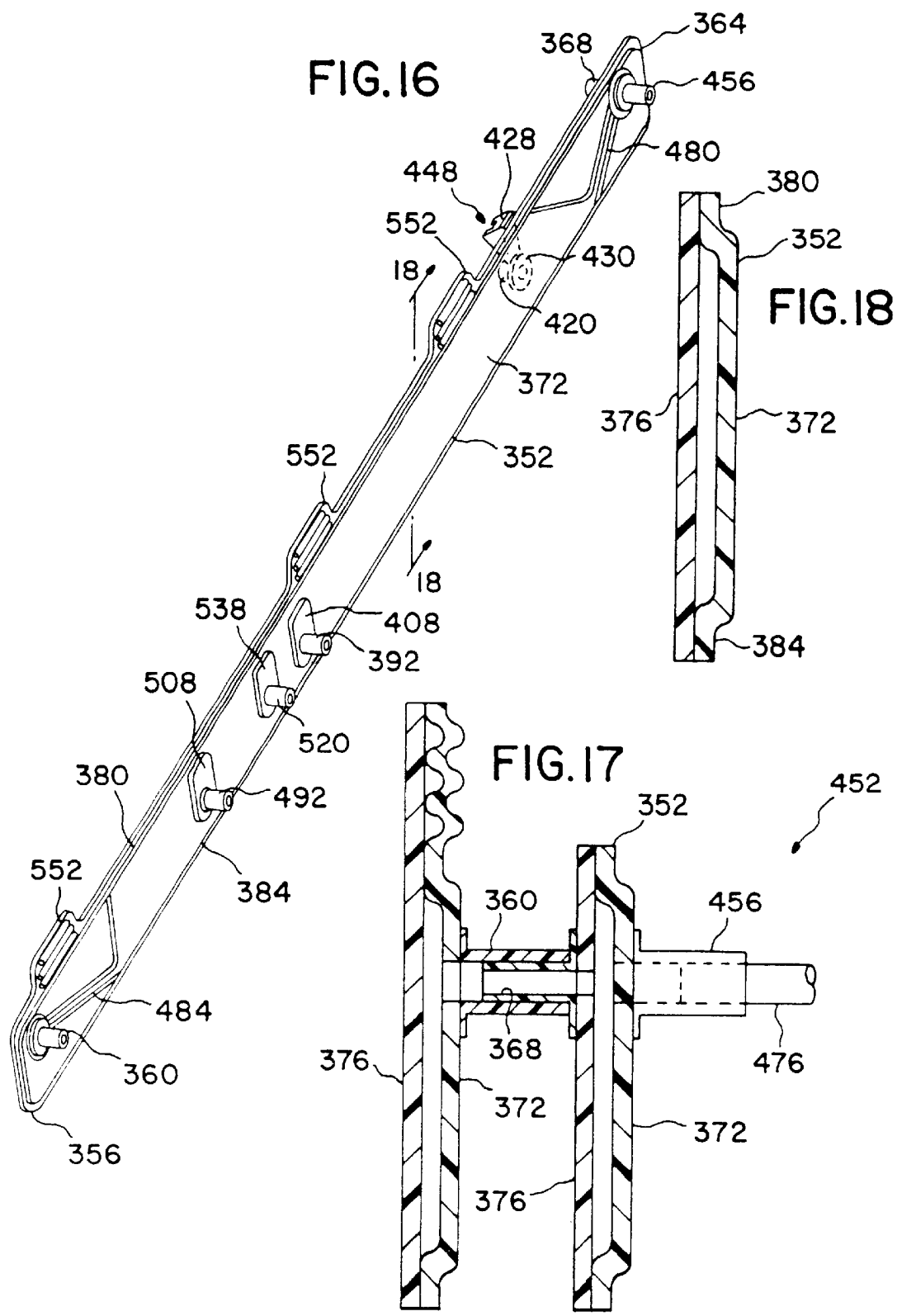

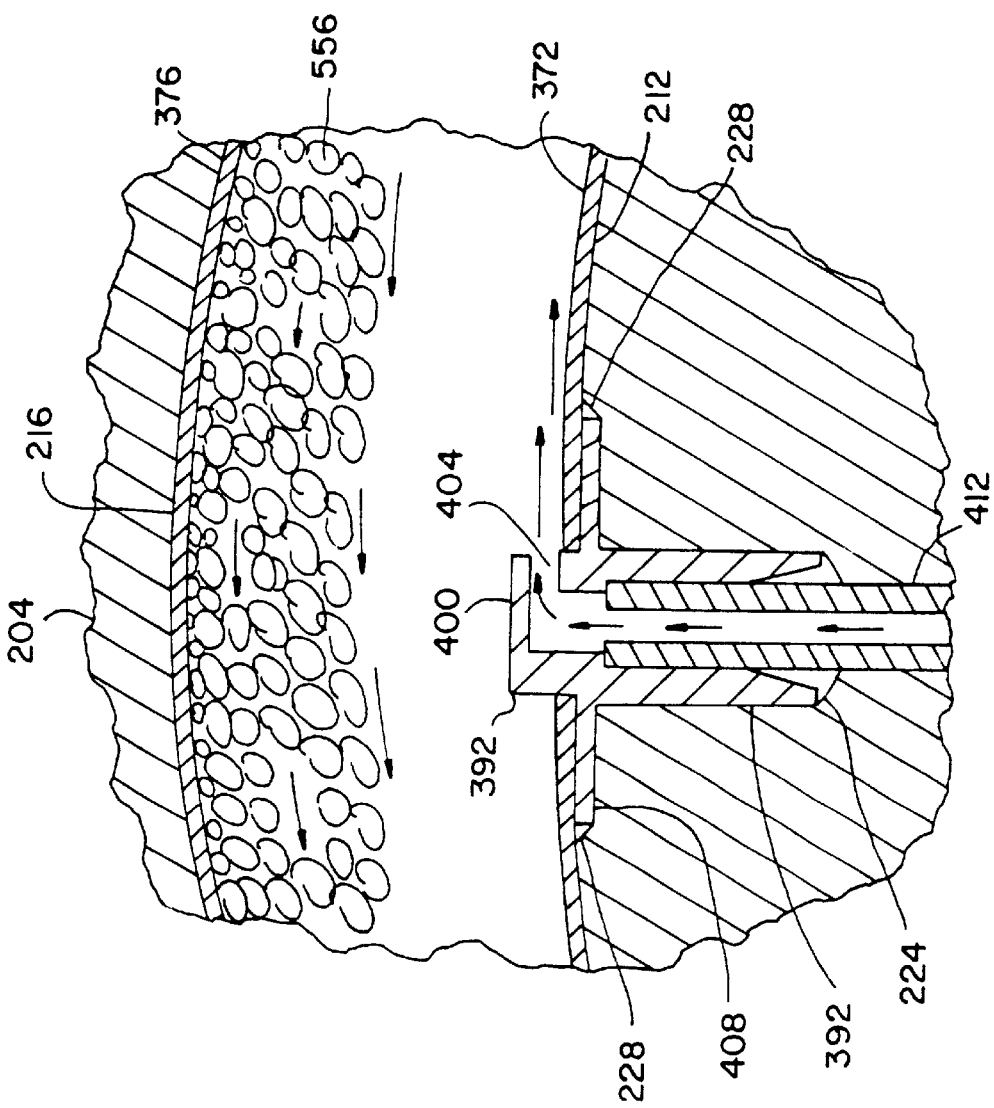

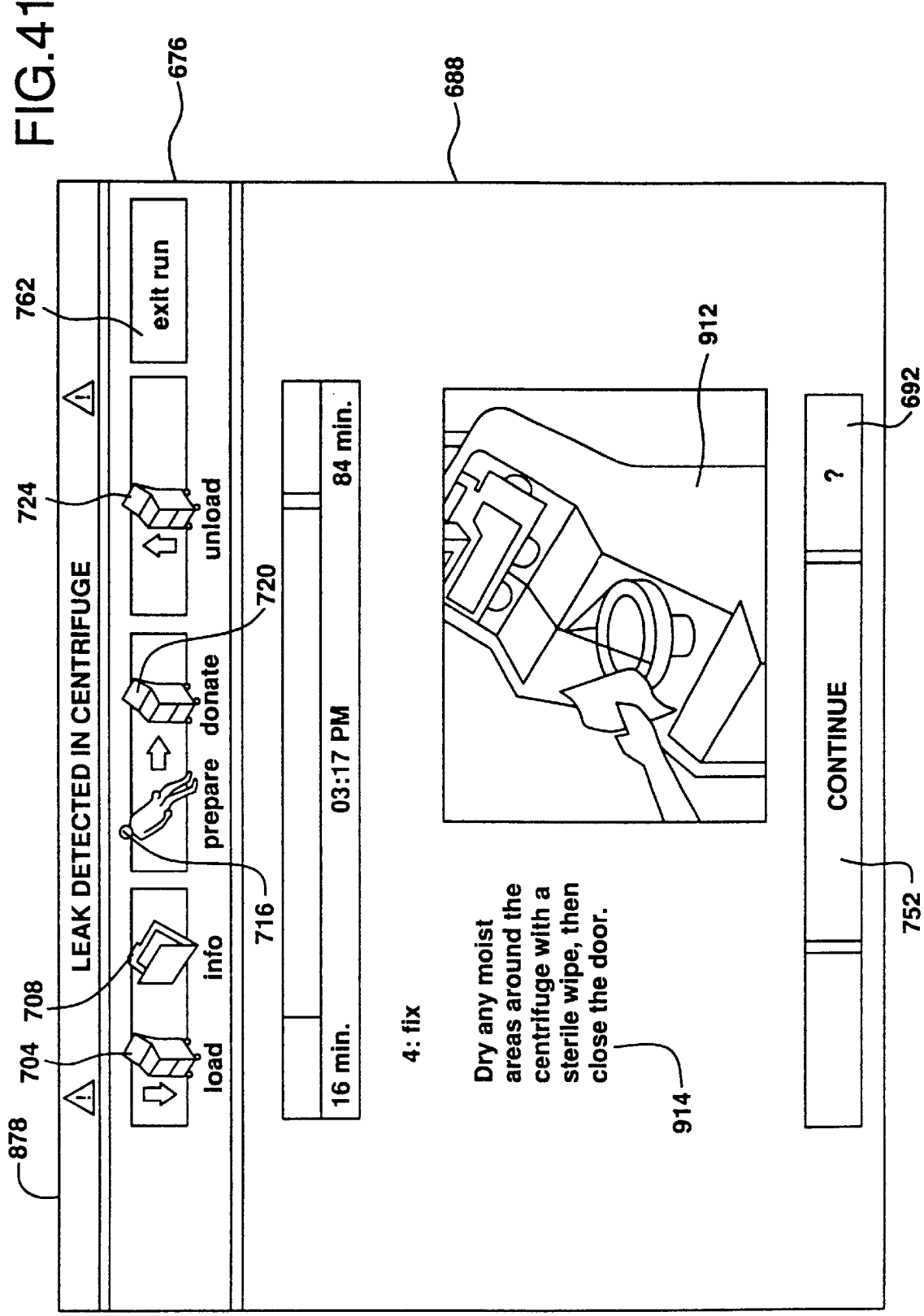

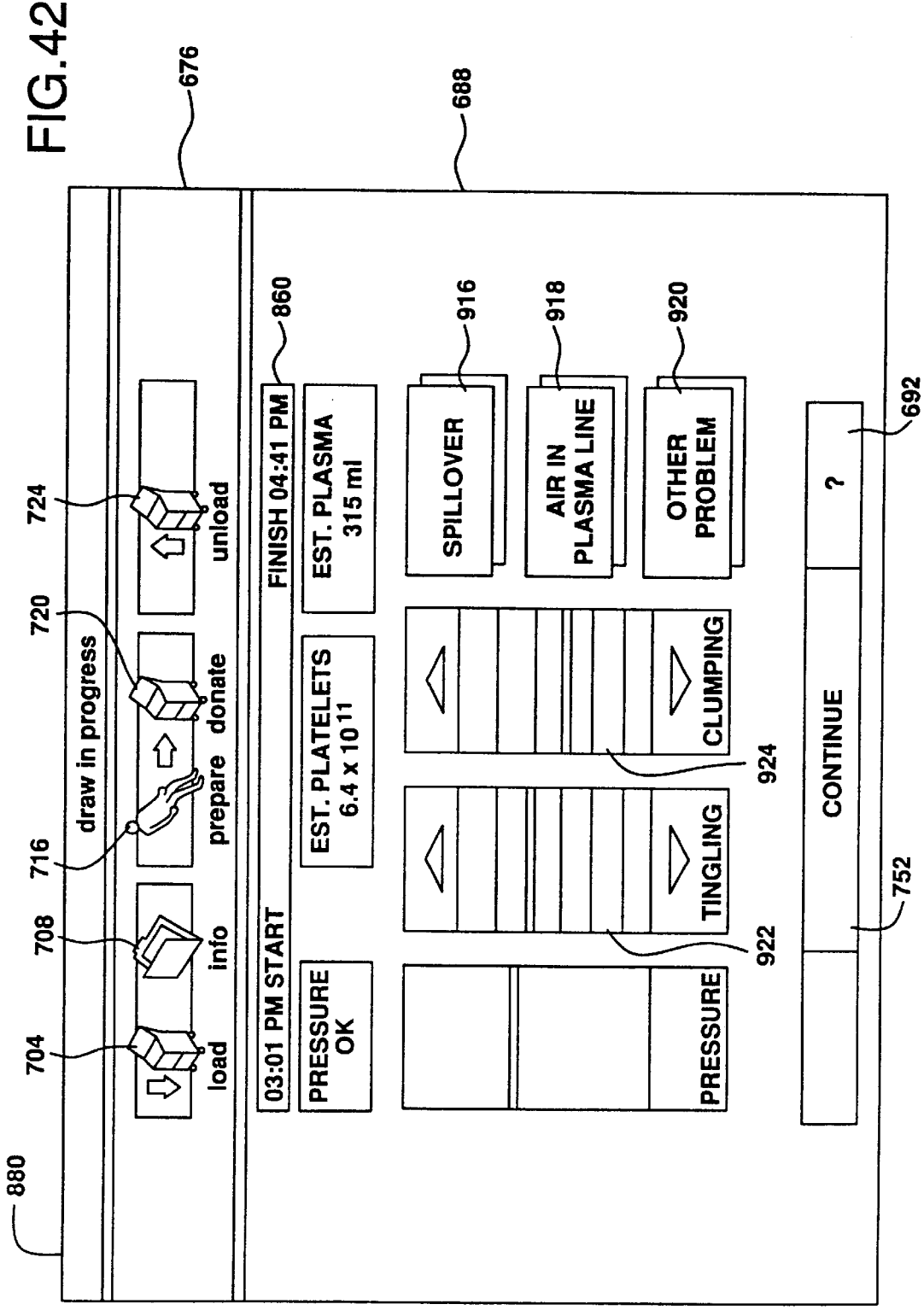

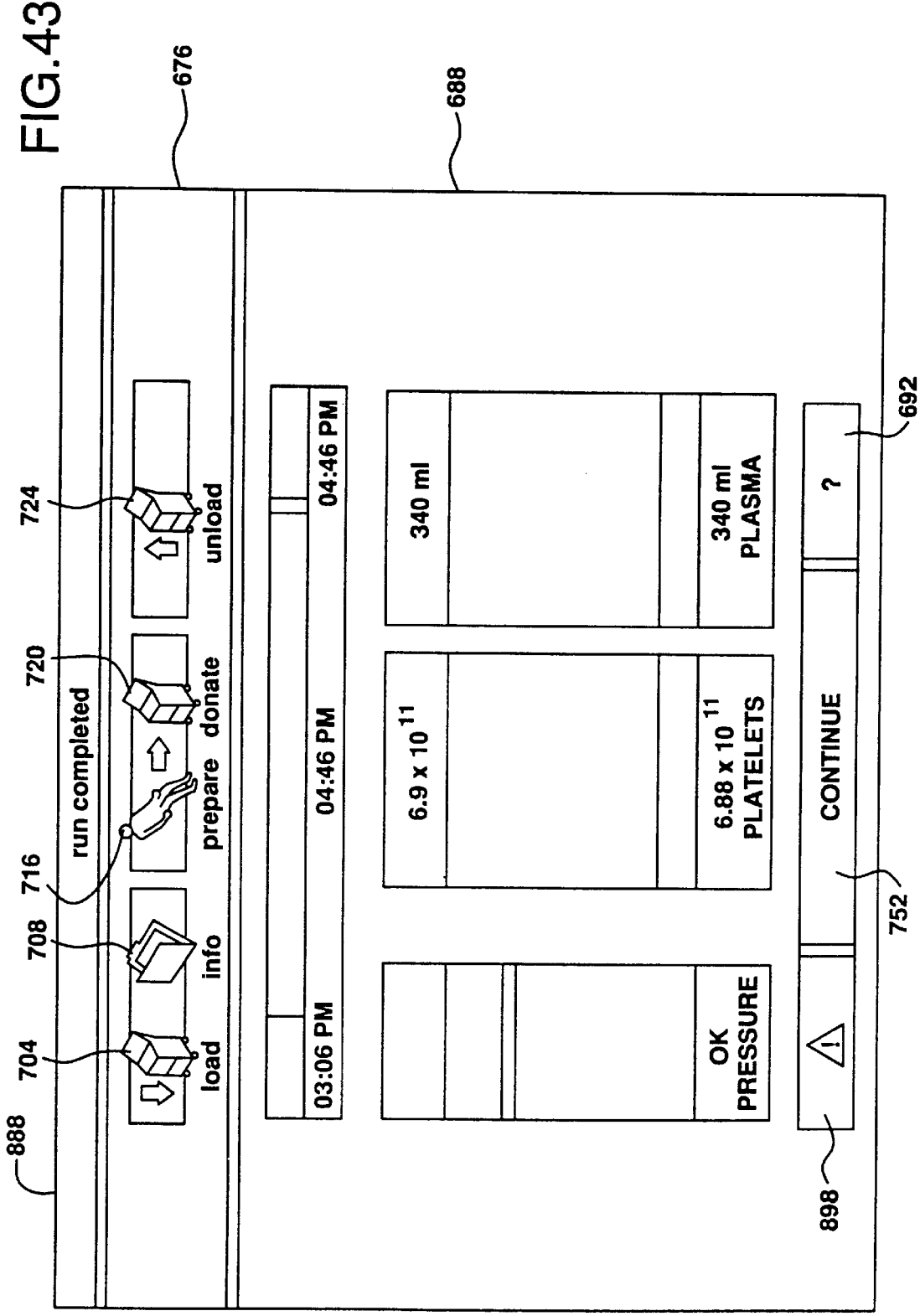

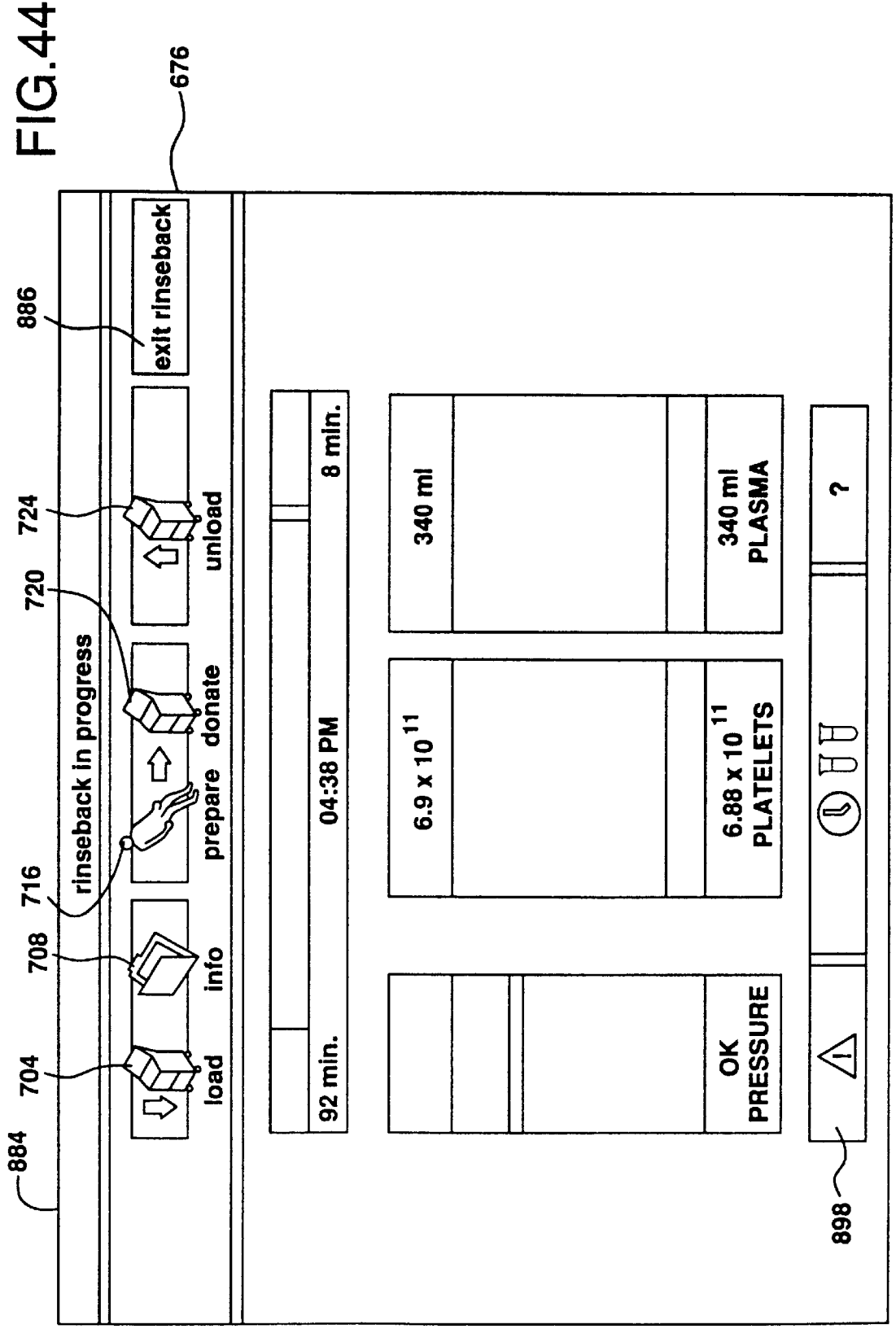

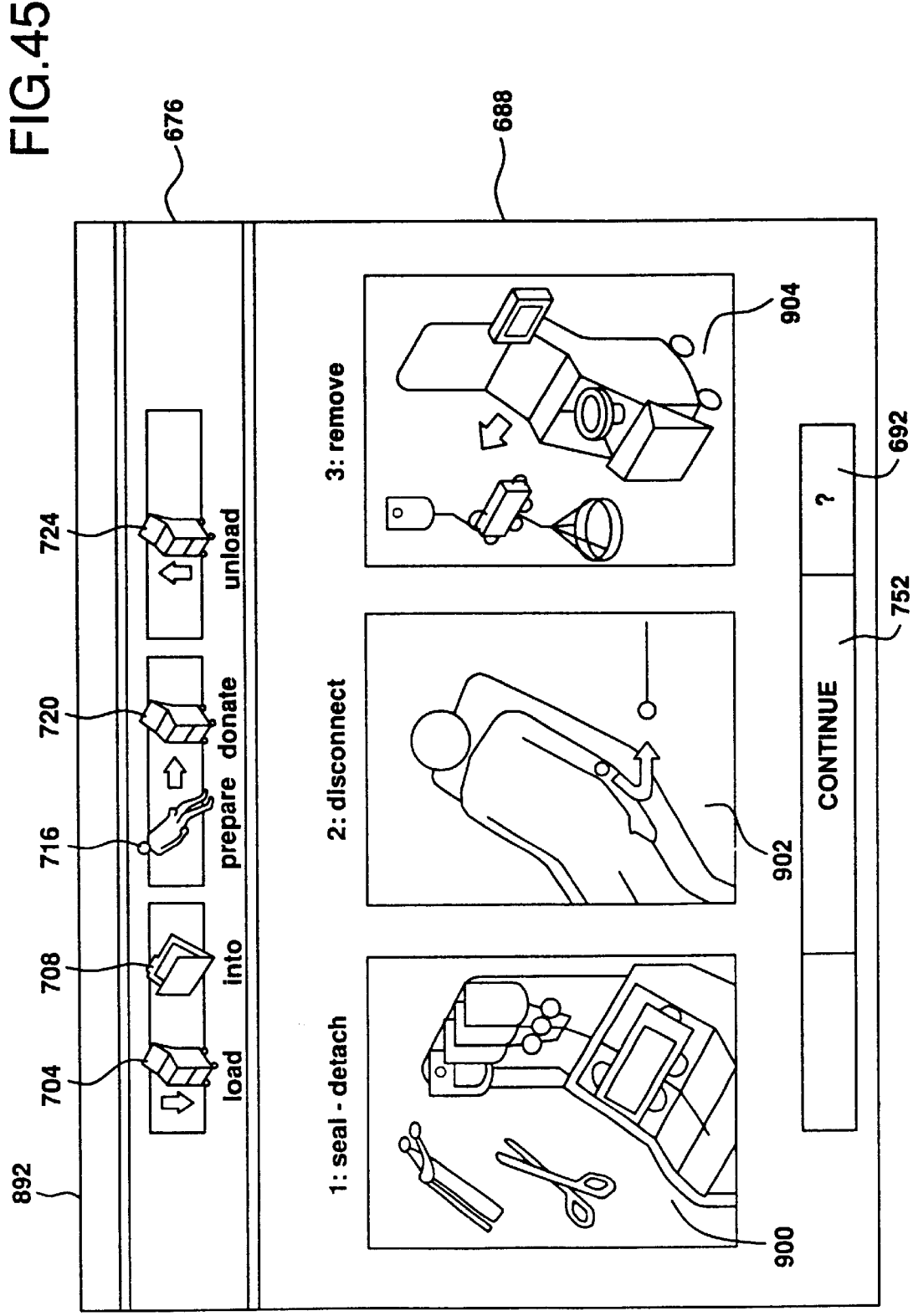

EXTRACORPOREAL BLOOD PROCESSING METHODS AND APPARATUS

This application is a divisional of U.S. patent application Ser. No. 08/486,217 filed on Jun. 7, 1995 now U.S. Pat. No. 5,795,317.

FIELD OF THE INVENTION

The present invention generally relates to the field of extracorporeal blood processing and, more particularly, to methods and apparatus which may be incorporated into an apheresis system (e.g., blood component collection, therapeutic).

BACKGROUND OF THE INVENTION

One type of extracorporeal blood processing is an apheresis procedure in which blood is removed from a donor or patient, directed to a blood component separation device (e.g., centrifuge), and separated into various blood component types (e.g., red blood cells, white blood cells, platelets, plasma) for collection or therapeutic purposes. One or more of these blood component types are collected (e.g., for therapeutic purposes), while the remainder are returned to the donor or patient.

A number of factors affect the commercial viability of an apheresis system. One factor relates to the operator of the system, specifically the time and/or expertise required of an individual to prepare and operate the apheresis system. For instance, reducing the time required by the operator to load and unload the disposables, as well as the complexity of these actions, can increase productivity and/or reduce the potential for operator error. Moreover, reducing the dependency of the system on the operator may lead to reductions in operator errors and/or to reductions in the credentials desired/required for the operators of these systems.

Donor-related factors may also impact the commercial viability of an apheresis system and include donor convenience and donor comfort. For instance, donors typically have only a certain amount of time which may be committed to visiting a blood component collection facility for a donation. Consequently, once at the collection facility the amount of the donor's time which is actually spent collecting blood components is another factor which should be considered. This also relates to donor comfort in that many view the actual collection procedure as being somewhat discomforting in that at least one and sometimes two access needles are in the donor throughout the procedure.

Performance-related factors continue to affect the commercial viability of an apheresis system. Performance may be judged in terms of the "collection efficiency" of the apheresis system, which may in turn reduce the amount of donation time and thus increase donor convenience. The "collection efficiency" of a system may of course be gauged in a variety of ways, such as by the amount of a particular blood component type which is collected in relation to the number of this blood component type which passes through the apheresis system. Performance may also be evaluated based upon the effect which the apheresis procedure has on the various blood component types. For instance, it is desirable to minimize the adverse effects on the blood component types as a result of the apheresis procedure (e.g., reduce platelet activation).

SUMMARY OF THE INVENTION

The present invention generally relates to extracorporeal blood processing. Since each of the various aspects of the present invention may be incorporated into an apheresis system (e.g., whether for blood component collection in which "healthy" cells are removed from the blood or for therapeutic purposes in which "unhealthy" cells are removed from the blood), the present invention will be described in relation to this particular application. However, at least certain of the aspects of the present invention may be suited for other extracorporeal blood processing applications and such are within the scope of the present invention.

An apheresis system which may embody one or more aspects of the present invention generally includes a blood component separation device (e.g., a membrane-based separation device, a rotatable centrifuge element, such as a rotor, which provides the forces required to separate blood into its various blood component types (e.g., red blood cells, white blood cells, platelets, and plasma)). In one embodiment, the separation device includes a channel which receives a blood processing vessel. Typically, a healthy human donor or a patient suffering from some type of illness (donor/patient) is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor/patient and directed to the blood component separation device such that at least one type of blood component may be separated and removed from the blood, either for collection or for therapy.

A first aspect of the present invention relates to enhancing the ease of loading a blood processing vessel into a channel which is associated with a centrifuge rotor. In one embodiment of this first aspect, the centrifuge rotor includes a blood processing vessel loading aperture in its sidewall which extends only part of the way through the centrifuge rotor and then extends upwardly through the top of the centrifuge rotor. The centrifuge rotor thereby provides an opposing surface to the portion of the loading aperture which may be characterized as laterally extending. The loading aperture within the centrifuge rotor may then be properly characterized as being substantially L-shaped. When the disposable blood processing vessel is inserted into this opening, it is deflected upwardly through the centrifuge rotor. The operator may then grasp the blood processing vessel and load it into the channel.

Another embodiment of this first aspect relates to a drive assembly for a centrifuge rotor assembly. The rotor assembly includes a rotor housing, a channel mounting having a channel associated therewith, and a single gear which rotatably interconnects the rotor housing and channel mounting. Through use of this single gear and by having this single gear be radially offset in relation to the above-described loading aperture in the centrifuge rotor, the access to the loading aperture is not substantially affected by the drive assembly for the centrifuge rotor. For instance, by radially offsetting the single drive gear in relation to a plane which bisects the loading aperture, any counterweights which are used to establish rotational balance of the centrifuge rotor will be disposed so as to not adversely affect access to the loading aperture.

A second aspect of the present invention relates to the cross-sectional configuration of at least a portion of a channel associated with a channel housing which is interconnectable with a blood component separation device. Generally, the channel itself is configured so as to retain the blood processing vessel therein during the apheresis procedure. This is particularly desirable in the case of the blood component collection device being a centrifuge which is operated at high rotational speeds, such as greater than 2,500 RPM and even up to about 3,000 RPM. In one embodiment, for at least a portion of the length of the channel a lip extends partially across an upper portion of the channel.

The lip in this second aspect may be provided by configuring at least one of the inner and outer channel walls with a generally C-shaped cross-sectional configuration. In this case, both the upper and lower portions of the channel having the noted lip would have reduced widths in comparison with the middle portion of the channel. These reduced width upper and lower portions of the channel may receive portions of a blood processing vessel which are sealed together. The channel configuration would then also serve to reduce the stresses experienced by these seals when the blood processing vessel is pressurized during the apheresis procedure.

A third aspect of the present invention relates to a blood processing vessel, and more specifically to a blood processing vessel which may be effectively loaded within a channel. In one embodiment of this third aspect, the blood processing vessel provides a continuous flow path by overlapping and radially off-setting first and second ends and utilizing first and second connectors. The first and second connectors are each positioned between the two ends of the blood processing vessel, communicate with the interior of the blood processing vessel, and when engaged facilitate the loading the blood processing vessel into the channel in the correct position. One of the connectors may be a stub-like structure which extends outwardly from the inner sidewall of the blood processing vessel, while the other connector may be a stub-like structure which extends outwardly from the outer sidewall of the blood processing vessel.

Another embodiment of this third aspect is a blood processing vessel which is particularly useful for the channel described in the second aspect above. In this regard, the blood processing vessel is sufficiently rigid so as to not only be free-standing, but to be loaded into the channel of the second aspect as well. However, the blood processing vessel is still sufficiently flexible so as to be able to substantially conform to the shape of the channel during an apheresis procedure. This is particularly desirable when the channel is shaped to provide one or more desired functions regarding the apheresis procedure.

Once the blood processing vessel is loaded into the channel, at least the blood processing vessel must be primed. In this regard, a fourth aspect of the present invention relates to priming, preferably with blood. A channel associated with a channel housing, which is rotatably interconnected with a centrifuge rotor, includes a first cell separation stage. The first cell separation stage is sized such that a ratio of a volume of the channel which does not have RBCs to a volume of the channel which does have RBCs is no greater than one-half of one less than the ratio of the hematocrit of blood entering the channel to the hematocrit of red blood cells exiting the channel. With this configuration, blood may be used to prime the blood processing vessel when disposed within the channel, and thus the channel may be properly characterized as "blood-primable."

In one embodiment of this fourth aspect, the channel extends generally curvilinearly about a rotational axis of the channel housing in a first direction. The channel includes, progressing in the first direction, the first cell separation stage, a red blood cell dam, a platelet collection area, a plasma collection area, and an interface control region for controlling a radial position of at least one interface between red blood cells and an adjacent blood component type(s) (e.g., a buffy coat of WBCs, lymphocytes, and platelets). Blood introduced into the channel is separated into layers of red blood cells, white blood cells, platelets, and plasma in the first cell separation stage. Preferably, throughout the apheresis procedure and including the priming of the blood processing vessel, only separated platelets and plasma flow beyond the red blood cell dam where the platelets may be removed from the channel in the platelet collection area. This is provided by an interface control mechanism which is disposed in the interface control region of the channel and which maintains the position of the interface between separated red blood cells and the buffy coat such that this condition is maintained.

Although the term "blood prime" is subject to a variety of characterizations, in each case blood is the first fluid introduced into the blood Processing vessel. One characterization of the blood prime is that separated plasma is provided to the interface control region before any separated red blood cells flow beyond the red blood cell dam into the platelet collection area. Another characterization is that blood and/or blood component types occupy the entire fluid-containing volume of the blood processing vessel before any separated red blood cells flow beyond the red blood cell dam into the platelet collection area.

One configuration of the channel which allows for a blood priming of the blood processing vessel when loaded within the channel is one in which the volume of that portion of the channel which principally contains plasma during the apheresis procedure is small in comparison to the volume of that portion of the channel which principally contains red blood cells during the apheresis procedure. This allows plasma to be provided to the interface control region of the channel before red blood cells flow beyond the red blood cell dam into the platelet collection stage to provide the red blood cell-buffy coat interface control function. That degree of "small" of the noted channel portion volume which allows for blood priming may be specifically defined in relation to a reference circle which has its origin on the rotational axis of the centrifuge housing and which intersects the channel at a predetermined location on the red blood cell dam. The volume of the channel which principally contains separated plasma in the apheresis procedure is disposed inside of this reference circle (e.g., $V_{PL}$) and the volume of the channel which principally contains separated red blood cells in the apheresis procedure is disposed outside of this reference circle (e.g., $V_{RBC}$). In one embodiment the ratio of $V_{PL}/V_{RBC}$ is no greater than about 0.3, and preferably no greater than about 0.25. This desired ratio may be achieved by having the width of the channel between the platelet collection area and the plasma collection area be less than the width of the channel throughout the first cell separation stage. By utilizing this reduced width, the configuration of the channel between the platelet collection area and the plasma collection area may utilize substantially vertically extending and planar inner and outer channel walls.

A fifth aspect of the present invention relates to priming a blood processing vessel disposed in a channel of a channel housing. Blood is used in the prime and the invention also accommodates for the removal of air from the blood processing vessel during this prime. A donor/patient blood transfer assembly fluidly interconnects the blood processing vessel and a donor/patient, and may include an air receptacle for receiving air which is displaced from the blood processing vessel by the blood priming. The various features associated with the channel of the above-noted fourth aspect of the invention may be utilized in this fifth aspect as well.

A sixth aspect of the present invention relates to blood priming an apheresis system which includes a channel housing having a blood processing channel associated therewith, a blood processing vessel disposed in the channel and which has a blood inlet port, red blood cell outlet port, and an interface control port. The interface control port is used to control the radial position of at least one interface between separated red blood cells and a blood component type(s) disposed adjacent the separated red blood cells.

A method of this sixth aspect includes the steps of rotating the channel housing with the blood processing vessel positioned in its channel, introducing blood into the blood processing vessel to prime the same, and separating the blood into at least red blood cells, platelets, and plasma. The red blood cells are restricted from flowing beyond the red blood cell dam throughout the procedure, including in the priming of the blood processing vessel. In this regard, a flow of plasma is provided to the interface control port before any of the red blood cells are able to flow beyond the red blood cell dam. Once this plasma reaches the interface control port, control is established of the radial position of the interface between the separated red blood cells and the adjacent blood component type(s) such that the potential for red blood cells flowing beyond the red blood cell dam is reduced. One or more of the various features discussed above with regard to the fourth and fifth aspects noted above may be incorporated into this sixth aspect as well.

A seventh aspect of the present invention is a method which may be utilized to prime a blood processing vessel disposed in a channel of a channel housing with blood. In this method, the blood processing vessel is disposed in the channel on the channel housing and a donor/patient blood transfer assembly fluidly interconnects a donor/patient with this blood processing vessel. The method generally includes the steps of initiating the flow of blood from the donor/patient to the donor/patient blood transfer assembly while rotating the channel housing at a first rotational velocity. Once the flow of blood reaches the blood processing vessel, the rotational velocity of the channel housing is increased to a second rotational velocity. Once the entirety of the blood processing vessel contains either blood and/or one or more blood component types, the rotational velocity of the channel housing is once again increased to a third rotational velocity. In one embodiment, the first rotational velocity ranges from about 180 RPM to about 220 RPM, and is preferably about 200 RPM, the second rotational velocity ranges from about 1,800 RPM to about 2,200 RPM and is preferably about 2,000 RPM, and the third rotational velocity ranges from about 2,700 RPM to about 3,300 RPM, and is preferably about 3,000 RPM. Although a three-step approach may be utilized in the practice of the method of this seventh aspect, the centrifuge speed need not stay at a fixed velocity during each of the three "stages" (e.g., the first stage being priming the extracorporeal circuit from the donor/patient to the blood processing vessel, the second stage being priming the blood processing vessel, and the third stage being the remainder of the apheresis procedure). One or more of the various features discussed above with regard to the fourth, fifth and sixth aspects noted above may be incorporated into this seventh aspect as well.

An eighth aspect of the invention relates to priming the apheresis system with blood. The apheresis system includes a channel housing having a channel associated therewith, a blood processing vessel disposed in the channel, a donor/patient blood transfer assembly which fluidly interconnects a donor/patient with the blood processing vessel and which includes a blood reservoir. A method in accordance with this eighth aspect includes performing first and second drawing steps. The first drawing step includes drawing blood from the donor/patient through a first portion of the donor/patient blood transfer assembly and into the blood reservoir. After this first drawing step is terminated, the blood processing vessel is primed with the donor/patient's blood by performing the second drawing step. The second drawing step includes drawing blood from the donor/patient, through a second portion of the donor/patient blood transfer assembly, through the blood processing vessel, and back into the blood reservoir. One or more of the various features discussed above with regard to the fourth, fifth, sixth, and seventh aspects noted above may be incorporated into this eighth aspect as well.

A ninth aspect of the present invention relates to the introduction of blood into the blood processing vessel such that the blood may be separated into at least two blood component types and further such that at least one of these blood component types may be removed from the blood processing vessel via a blood component outlet port. The blood processing vessel includes two interconnected sidewalls (e.g, substantially planar surfaces which define the main body of the fluid-containing volume of the blood processing vessel) and the blood inlet port extends through one of these sidewalls. Generally, the blood exits the blood inlet port within the interior of the blood processing vessel in a direction which is at least partially in the direction of the primary flow of blood through the channel. This introduction of blood into the blood processing vessel is subject to a number of characterizations. For instance, the introduction may be characterized as the blood exiting the blood inlet port into the interior of the blood processing vessel at an angle of less than 90° relative to a reference line extending perpendicularly to the channel wall which interfaces with the blood inlet port. The introduction may be further characterized as exiting the blood inlet port in a direction which is substantially parallel with a direction of flow adjacent the blood inlet port. In one embodiment, red blood cells may actually flow along the outer wall of the blood processing vessel past the blood inlet port such that the noted introduction of blood into the blood processing vessel may be further characterized as reducing the potential for disturbing this flow of red blood cells and/or as reducing an effect on flow characteristics in the area of the blood processing vessel in which blood is introduced. The introduction may be further characterized as exiting the blood inlet port in a direction which is substantially parallel with the sidewall of the blood processing vessel which interfaces with the blood inlet port.

A tenth aspect of the present invention relates to the removal of platelets from the blood processing vessel. This tenth aspect is based upon the blood processing vessel and part of the adjacent channel wall of the channel collectively defining a generally funnel-shaped blood component collect well which collects at least one blood component type flowing thereby (e.g., platelets). In one embodiment, the blood processing vessel includes a blood inlet port and a first blood component outlet port. A support is disposed proximate the blood component outlet port and exteriorly relative to the fluid-containing volume of the blood processing vessel. This support is contoured to direct the desired blood component type(s)toward the blood component outlet port and is in an overlapping relation with the exterior surface of the blood processing vessel. The support may be separable from the blood processing vessel such that it may be positioned between the blood processing vessel and the associated channel wall after the vessel is loaded into the channel. The support may also be fixedly interconnected with the blood processing vessel in some manner. For instance, the support may be pivotally or hingedly interconnected with the exterior of the blood processing vessel to facilitate loading of the blood processing vessel and/or to allow the support to move into a predetermined position upon pressurization of the blood processing vessel during an apheresis procedure to perform the desired function. Moreover, the support may be integrally formed with the associated blood component outlet port.

In another embodiment relating to this tenth aspect, the channel includes inner and outer channel walls and part of a generally funnel-shaped blood component collect well is formed in at least one of these channel walls. That is, the remainder of the funnel-shaped blood component collect well is defined by the blood processing vessel, such as described above in relation to the first embodiment of this tenth aspect. In order to allow the above-described blood processing vessel to be effectively loaded into the blood processing channel, specifically one of its blood component outlet ports, a blood component outlet port recess extends radially beyond the portion of the blood component collect well defined by the channel wall (e.g., if the well is on the outer wall of the channel, this would be further radially outwardly, whereas, if the well is on the inner wall of the channel, this would be further radially inwardly). This recess may also be configured so as to allow the above-noted contoured support, which interfaces with the exterior of the blood processing vessel, to move into a predetermined position upon pressurization of the blood processing vessel to direct the desired blood component type(s) into the blood component collect port.

In another embodiment of this tenth aspect, a method for processing blood in an apheresis system includes the steps of loading a blood processing vessel in a channel on a channel housing. A contoured support is disposed between the channel and the blood processing channel. When blood is introduced into the blood processing vessel and the channel housing is rotated to separate the blood into various blood component types, a generally funnel-shaped platelet collect well is defined by conforming one part of the blood processing vessel to the channel and by further conforming another part of the blood processing vessel to the shape of the support interfacing with the blood processing vessel. In order to further define this generally funnel-shaped platelet collect well, pressurization of the blood processing vessel may move the support into a predetermined position. For instance, this may then allow the support to direct the platelets toward a platelet collect port on the blood processing vessel.

An eleventh aspect of the present invention relates to a control port which assists in automatically controlling (i.e., without operator action) the location of an interface between red blood cells and a buffy coat relative to a red blood cell dam. The red blood cell dam restricts the flow of separated red blood cells to a platelet collect port. The control port extends through the blood processing vessel and removes plasma and red blood cells as required in order to reduce the potential for red blood cells flowing "over" the red blood cell dam to the platelet collect port. The "selective" removal of red blood cells from the blood processing vessel through the control port function is based at least in part upon its position within the channel. That is, the automatic control provided at least in part by the control port is predicated upon the control port assuming a predetermined radial position within the channel. In order to facilitate achieving this predetermined radial position within the channel, the disposition of the control port is provided independently of the thickness of the blood processing vessel. Specifically, the position of the control port is not dependent upon the thickness of the materials which form the blood processing vessel.

The desired objective for the control of this eleventh aspect of the present invention may be affected by interconnecting a support or shield-like structure with the control port and disposing this support over an exterior surface of the blood processing vessel. This support may then be positioned against an interior surface of the channel, preferably within a recess which is specifically designed to receive the support. This support may also be more rigid than the blood processing vessel itself which reduces the potential for any significant change in the radial position of the control port when the blood processing vessel is pressurized (e.g., any radial movement within a slot which receives the control port and which allows the control port to extend within the channel). These support or shield-like members may also be used for other blood inlet/outlet ports on the blood processing vessel to similarly maintain the associated port in a predetermined position and/or to reduce the discontinuity along the part of the channel with which the port interfaces.

A twelfth aspect of the present invention relates to a packing factor associated with the separated blood component types in a separation stage(s) of the blood processing vessel. The packing factor is a number which reflects the degree with which the blood component types are "packed together" in the separation stage(s) and is dependent at least upon the rotational speed of the channel housing and the flow rate into the blood processing vessel. The packing factor may be characterized as a dimensionless "density" of sorts of the blood component types in the separation stage (s).

One embodiment of this twelfth aspect is a method which includes the steps of rotating the channel housing, providing a flow to the blood processing (e.g., the flow includes blood and typically anticoagulant as well), separating the blood into a plurality of blood component types, and adjusting the rotational speed of the channel housing based upon a certain change in the flow rate. Since the packing factor is dependent upon the rotational speed of the channel housing and the flow rate into the blood processing vessel, the methodology of this eleventh aspect may be used to maintain a substantially constant and predetermined packing factor. In this regard, preferably the packing factor is maintained between about 11 and about 15, and preferably about 13.

Another embodiment of this twelfth aspect is a method for processing blood in an apheresis system in which a blood processing vessel is disposed in a channel of a channel housing. The method includes the steps of rotating the channel housing, providing a flow of blood (typically anticoagulated) to the blood processing vessel at a rate ranging from about 40 milliliters per minute to about 70 milliliters per minute, separating the blood into a plurality of blood component types in a first stage of the channel, and removing at least one of the blood component types from the blood processing vessel. Throughout the separating step, a packing factor of at least about 10, and more preferably at least about 10.2, is maintained in the first stage. For flow rates up to about 50 milliliters per minute, the packing factor is more preferably maintained at about 13 which may be achieved by rotating the channel housing at speeds greater than 2,500 RPM and typically closer to about 3,000 RPM.

Another embodiment of this twelfth aspect of the present invention relates to the configuration of a channel associated with a channel housing which is rotatably interconnected with a centrifuge rotor. The channel includes a first cell separation stage and a first blood component collection stage which are separated by a cell dam. At least one type of blood component is separated from remaining portions of the blood in the first cell separation stage and flows beyond the cell dam into the first blood component collection stage, while at least one other type of blood component is preferably precluded from flowing beyond the cell dam into the first blood component collection stage. The width or sedimentation distance of the channel on the end of the first cell separation stage disposed closest to the cell dam is less than the width or sedimentation distance of the channel on the opposite end of the first cell separation stage. In one embodiment, the width/sedimentation distance of the channel in the first cell separation stage is progressively reduced approaching the cell dam. When the above-identified types of packing factors are utilized, this channel configuration may be used to reduce the volume of a buffy coat (white blood cells, lymphocytes, and platelets) between separated red blood cells and platelets in the first stage, and thus reduces the number of platelets that are retained within the first cell separation stage.

A thirteenth aspect of the present invention relates to the rinseback operation at the end of the apheresis procedure in which attempts are made to remove the remaining contents of the blood processing vessel and provide the same back to the donor/patient. In one embodiment, one or more ports of the blood processing vessel, which interface with the sidewall of the blood processing vessel, are configured in a manner which reduces the potential for any closure of the port(s) during the rinseback procedure due to interconnecting one or more pumps with these ports. The port(s) is configured so as to have an orifice displaced from the radially outwardmost end of the port. This may be provided by configuring the end of the port to have the orifice positioned between two protrusions such that the orifice is recessed inwardly of the protrusions. Consequently, if the opposing portion of the blood processing vessel engages the protrusions during rinseback, the orifice is retained away from the blood processing vessel so as to not block the flow to the orifice.

In another embodiment relating to this thirteenth aspect, at least one narrowed portion within the blood processing vessel extends downwardly from at least one of the blood component outlet ports interfacing with the sidewall of the blood processing vessel toward a lower portion of the blood processing vessel. As such, during rinseback a drawing-like action, for instance achieved by pumping from the blood processing vessel out the blood component outlet port(s), is initiated in a lower portion of the blood processing vessel where the contents of the blood processing vessel will be if rotation of the channel housing is terminated during rinseback as preferred. A second narrowed portion may extend downwardly from the noted blood component outlet port such that one passageway extend away from the port in opposing directions and such that the drawing-like action is initiated in two displaced locations.

A fourteenth aspect of the present invention relates to facilitating insertion/loading and removal of a blood processing vessel to and from, respectively, a channel associated with a channel housing upon completion of an apheresis procedure. Generally, the blood processing vessel may be removed from and loaded into the channel by engaging structure which does not have any flow therethrough during the apheresis procedure. This may be achieved by interconnecting at least one and preferably a plurality of tabs or the like with the blood processing vessel. These tabs extend beyond the fluid-containing volume of the blood processing vessel and preferably extend beyond the channel when the vessel is loaded within the channel. As such, the tab(s) may be grasped by the operator of the apheresis system to load and unload the blood processing vessel to/from the channel. These tabs or the like may be particularly useful when there is some resistance to insertion/removal of the blood processing vessel from the channel, such as when a lip is formed on the upper portion of the channel as discussed in relation to the second aspect.

A fifteenth aspect of the present invention relates to providing a graphical operator interface for the procedure. This graphical operator interface pictorially displays to the operator at least a portion of the steps for the apheresis procedure, at least one of which requires some type of operator action. These steps may be pictorially displayed in the order in which they are to be performed. In order to further enhance operator recognition of the ordering of the pictorially displayed apheresis steps, the pictorials may also be numbered. Although the pictorials may alone convey to the operator the desired/required action, short textual descriptions may also be used in combination with the pictorials.

The pictorials may also be utilized to indicate the status of the apheresis procedure to the operator, such as by color or shade differentiation. For instance, three-way color or "shade" differentiation (e.g., in the case of colors using three different colors, and in the case of shade using the same general color but different levels of "darkness") may be utilized to indicate to the operator one of three conditions pertains to the step(s) associated with a particular pictorial. One color or shade may be utilized to indicate that the step(s) associated with the pictorial are untimely (e.g., not yet ready for execution), while another color or shade may be utilized to indicate that the step(s) associated with the pictorial are timely (e.g., ready for execution and/or are currently being executed), while yet another color or shade may be utilized to indicate that the step(s) associated with the pictorial have been executed. The status may also be conveyed by providing further indicia that the step(s) associated with a given pictorial have been completed.

The pictorials may further function as an operator input device. For instance, touch screen principles may be utilized such that the operator will touch one of the pictorials on the display when the operator is ready to execute the step(s) associated with the pictorial. This touch screen activation may generate one or more additional pictorials which graphically convey to the operator one or more steps or substeps which need to be undertaken at that particular time in the apheresis procedure.

A sixteenth aspect of the present invention also relates to an interface between the apheresis system and the operator. One embodiment of this sixteenth aspect is a method which includes the steps of instructing the apheresis system to address a first condition associated with the apheresis system by performing a first protocol. Typically, this "first condition" will be some type of problem associated with the apheresis system which may be resolved in a multiplicity of ways (e.g., at least two), such as by performing the first protocol or by performing a second protocol. That is, the methodology relates to "programming" the apheresis system to address or "correct" the first condition in one out of a plurality of ways and which does not allow/require the operator to make any decisions regarding how to address or "correct" the first condition.

In this embodiment of the sixteenth aspect, the methodology includes the steps of introducing blood into a blood separation device, separating the blood into a plurality of blood component types, and removing at least one of the blood component types from the device. The methodology also includes the step of identifying the existence of the first condition relating to the apheresis system and thereafter having the apheresis system perform the first protocol. This "identification" of the first condition may be based upon the operator observing the first condition and inputting information relating to the existence of the first condition to the apheresis system. This methodology may be effectively integrated into and/or utilize the graphical interface discussed above in relation to the fifteenth aspect of the invention.

Another embodiment relating to this sixteenth aspect relates to the apheresis system utilizing the operator to address potential problems associated with the apheresis procedure. A method of this sixteenth aspect includes the steps of introducing blood to the blood separation device, separating the blood into a plurality of blood component types, and removing at least one of these blood component types from the blood separation device. The method further includes the step of detecting the potential existence of a "first condition" associated with the apheresis procedure. This "first condition" is typically some potential problem and may be detected by the system itself (e.g., through appropriate detectors/sensors/monitors), the operator, and/or the donor/patient. Once this first condition is detected, the operator is prompted by the apheresis system (e.g., via a computer interface) to perform an investigation of the system or a particular portion thereof. The operator is also prompted to specify the result of this investigation to the system. Based upon the operator's response to the investigation, the system may prompt the operator to take further action (e.g., to address the first condition in a particular manner). Once again, this methodology may be effectively integrated into and/or utilize the graphical interface discussed above in relation to the fifteenth aspect of the invention.

A seventeenth aspect of the present invention relates to a disposable assembly for extracorporeal blood processing that utilizes a single pressure sensing device to monitor positive and negative pressure changes in both the blood removal line and blood return line interconnectable with a donor/patient. In one embodiment, a pressure sensitive diaphragm member contacts blood on one side within a module of a molded cassette member, which cassette member may also include an integrally defined internal passageway fluidly interconnecting the module with both the blood removal and blood return lines. The use of a single pressure sensor reduces component costs and complexity, and yields significant accuracy advantages.

An eighteenth aspect of the present invention further pertains to a disposable assembly for extracorporeal blood processing having a single needle for removal/return of whole blood/uncollected blood components, a reservoir fluidly interconnected to the single needle for accumulating blood components, and a gas holding means fluidly interconnected to the reservoir for receiving gas from the reservoir and returning the gas to the reservoir as the reservoir cyclically accumulates and disposes uncollected blood components during a blood processing operation. In one embodiment, the reservoir is integrally defined within a molded cassette member. The provision of a gas holding means avoids a high internal pressure buildup as the reservoir is filled with returned blood components, thereby reducing gas entrainment at the liquid/gas interface and lowering the seal requirements for the reservoir and interconnected components.

A nineteenth aspect of the present invention relates to an extracorporeal blood processing device which includes a cassette member having a reservoir for accumulating uncollected blood components, and upper and lower ultrasonic sensors positionable adjacent to the reservoir and being responsive to the presence or absence, respectively, of fluid adjacent thereto within the reservoir to trigger the start and stop of blood return cycles. In a related aspect, each of the upper and lower ultrasonic sensors may advantageously comprise a contact surface for direct, dry-docking with the reservoir, thereby avoiding the need for the use of a docking gel or other like coupling medium.

A twentieth aspect of the present invention relates to an extracorporeal blood processing device that comprises a cassette member having a reservoir, at least first and second flexible tubing lines adjacently interconnected to the cassette member in predetermined spaced relation, a collection means interconnected to one of the flexible tubing lines, and an interfacing valve assembly having a moveable member selectively positionable to occlude one of the tubings lines, such that in a first mode of operation a separated blood component will be collected in the collection means, and in a second mode of operation the separated blood component will be diverted into the reservoir. In one embodiment, multiple sets of corresponding first and second tubing lines/collection means/ and valve assemblies are provided, with each of the sets providing for selective diversion of a blood component into a separate collection means or common reservoir. Utilization of this arrangement yields a compact disposable that can be readily mounted relative to the divert valve assemblies in a reliable manner.

A twenty-first aspect of the present invention relates to loading of a disposable cassette member having a plurality of tubing loops extending therefrom relative to a plurality of flow control devices and at least one sensing device for extracorporeal blood processing. A mounting means is employed for selectively, securably and supportably receiving the cassette member in a substantially fixed position relative thereto, and the mounting means is selectively moveable between first and second locations wherein upon moving the mounting means from the first to second location, the tubing loops move into an operative position with corresponding ones of the flow control devices and the cassette member moves into a proper position for operation of the sensing means. In one embodiment, the sensing means includes at least one pressure sensor for monitoring the fluid pressure within a blood removal passageway of the cassette member, and further includes ultrasonic sensors for monitoring the fluid level of accumulated, uncollected blood components within a reservoir of the cassette.

BRIEF DESCRIPTION OF THE DRAWINGS

FIGS. 4A–4B are cross-sectional side views of first and second pressure sensing modules of the extracorporeal tubing circuit of FIGS. 2A–2B coupled with corresponding pressure sensors of the pump/valve/sensor assembly of FIG. 1;

FIGS. 9–9B is a top view of the channel housing from the channel assembly of FIG. 8 illustrating various dimensions;

FIG. 16 is a perspective view of the blood processing vessel of the channel assembly of FIG. 8 in a disassembled state;

FIG. 17 is a cross-sectional view of the blood processing vessel at the interconnection;

FIG. 8 is cross-sectional view of the blood processing vessel taken along lines 18—18 in FIG. 16;

FIG. 19G is a cross-sectional view, looking downwardly, of blood being introduced into the blood processing vessel and channel of FIG. 8 during an apheresis procedure;

FIG. 41 is a "supplemental alarm screen" for the alarm screen of FIG. 40;

FIG. 42 is one embodiment of a "trouble shooting screen" for the computer graphics interface of the apheresis system of FIG. 1;

FIG. 43 is a "final run data display screen" for the computer graphics interface of the apheresis system of FIG. 1;

FIG. 44 is a "rinseback screen" for the computer graphics interface of the apheresis system of FIG. 1;

FIG. 45 is an "unload screen" for the computer graphics interface of the apheresis system of FIG. 1;

DETAILED DESCRIPTION

The present invention will be described in relation to the accompanying drawings which assist in illustrating the pertinent features thereof. Generally, all aspects of the present invention relate to improvements in a blood apheresis system, both procedural and structural. However, certain of these improvements may be applicable to other extracorporeal blood processing applications and such are within the scope of the present invention as well.

Figure 1:
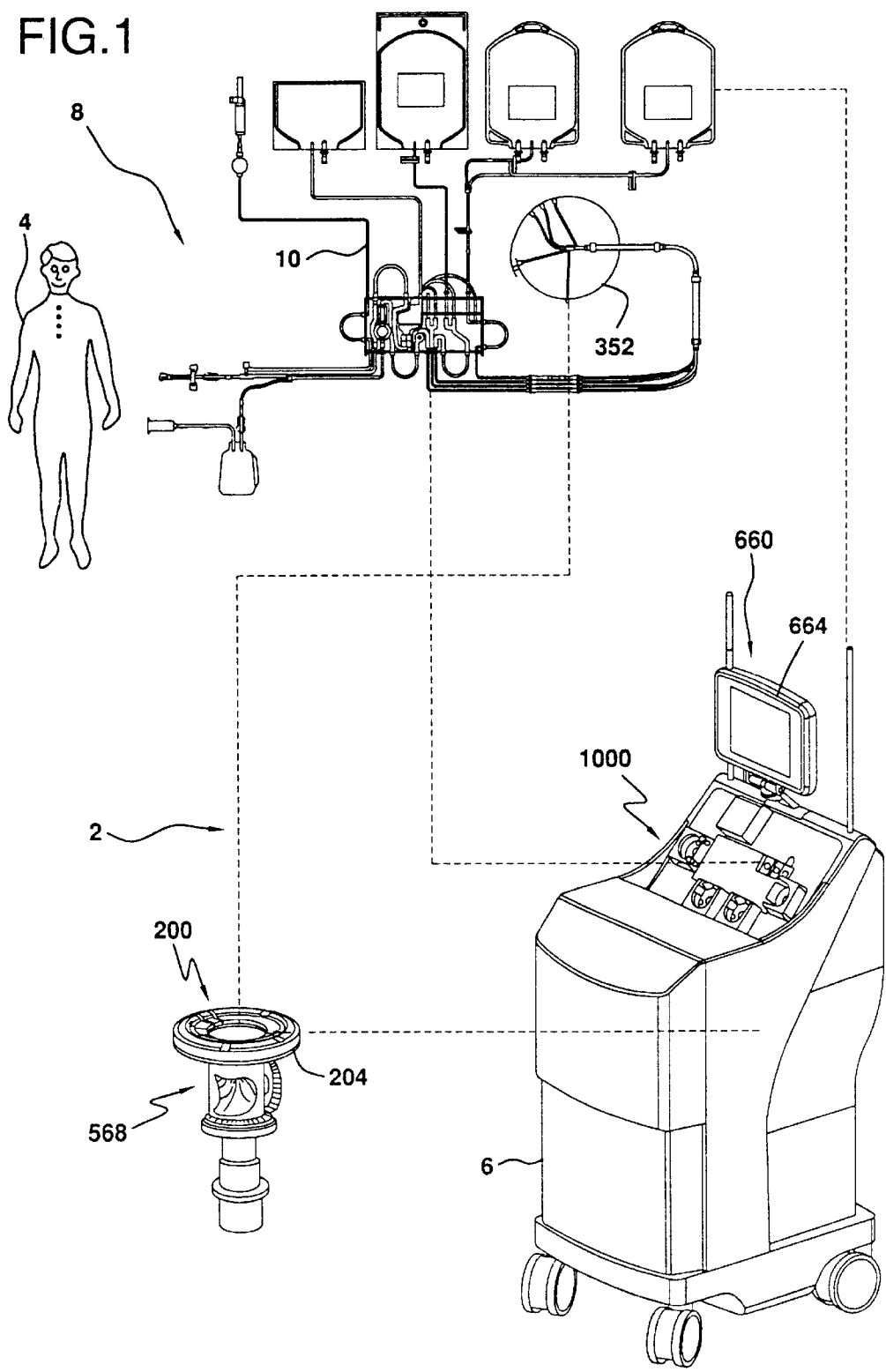
FIG. 1 is a perspective view of one embodiment of an apheresis system.

A blood apheresis system 2 is illustrated in FIG. 1 and allows for a continuous blood component separation process. Generally, whole blood is withdrawn from a donor/patient 4 and is provided to a blood component separation device 6 where the blood is separated into the various component types and at least one of these blood component types is removed from the device 6. These blood components may then be provided for subsequent use by another or may undergo a therapeutic treatment and be returned to the donor/patient 4.

In the blood apheresis system 2, blood is withdrawn from the donor/patient 4 and directed through a disposable set 8 which includes an extracorporeal tubing circuit 10 and a blood processing vessel 352 and which defines a completely closed and sterile system. The disposable set 8 is mounted on the blood component separation device 6 which includes a pump/valve/sensor assembly 1000 for interfacing with the extracorporeal tubing circuit 10, and a channel assembly 200 for interfacing with the disposable blood processing vessel 352.

The channel assembly 200 includes a channel housing 204 which is rotatably interconnected with a rotatable centrifuge rotor assembly 568 which provides the centrifugal forces required to separate blood into its various blood component types by centrifugation. The blood processing vessel 352 is interfitted with the channel housing 204. Blood thus flows from the donor/patient 4, through the extracorporeal tubing circuit 10, and into the rotating blood processing vessel 352. The blood within the blood processing vessel 352 is separated into various blood component types and at least one of these blood component types (e.g., platelets, plasma, red blood cells) is continually removed from the blood processing vessel 352. Blood components which are not being retained for collection or for therapeutic treatment (e.g., red blood cells, white blood cells, plasma) are also removed from the blood processing vessel 352 and returned to the donor/patient 4 via the extracorporeal tubing circuit 10.

Operation of the blood component separation device 6 is preferably controlled by one or more processors included therein, and may advantageously comprise a plurality of embedded personal computers to accommodate interface with ever-increasing PC user facilities (e.g., CD ROM, modem, audio, networking and other capabilities). Relatedly, in order to assist the operator of the apheresis system 2 with various aspects of its operation, the blood component separation device 6 includes a graphical interface 660.

Disposable Set: Extracorporeal Tubing Circuit

Figure 2A:
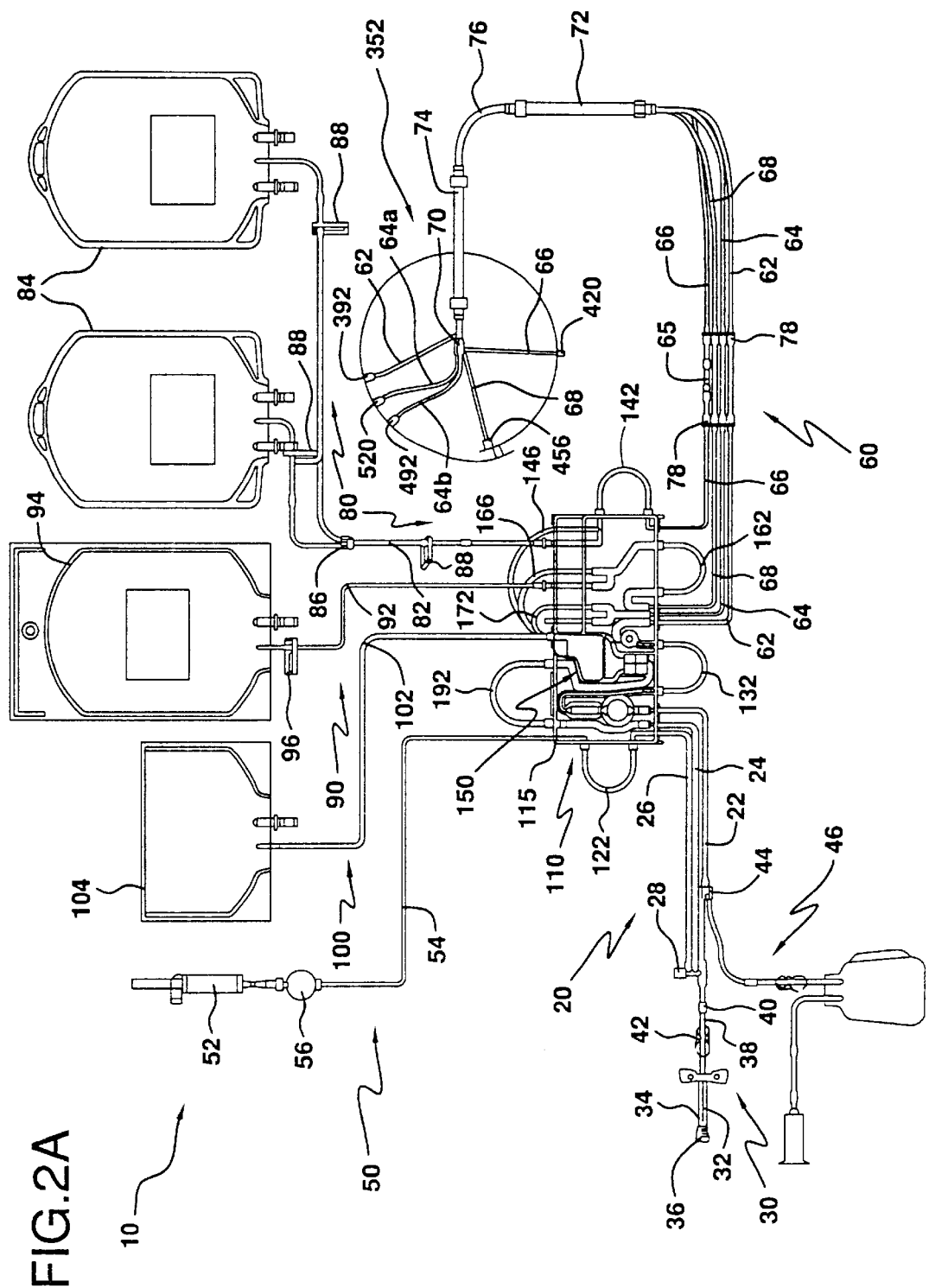
FIGS. 2A–2B illustrate an extracorporeal tubing circuit and cassette assembly thereof for the system of FIG. 1.
Figure 2B:
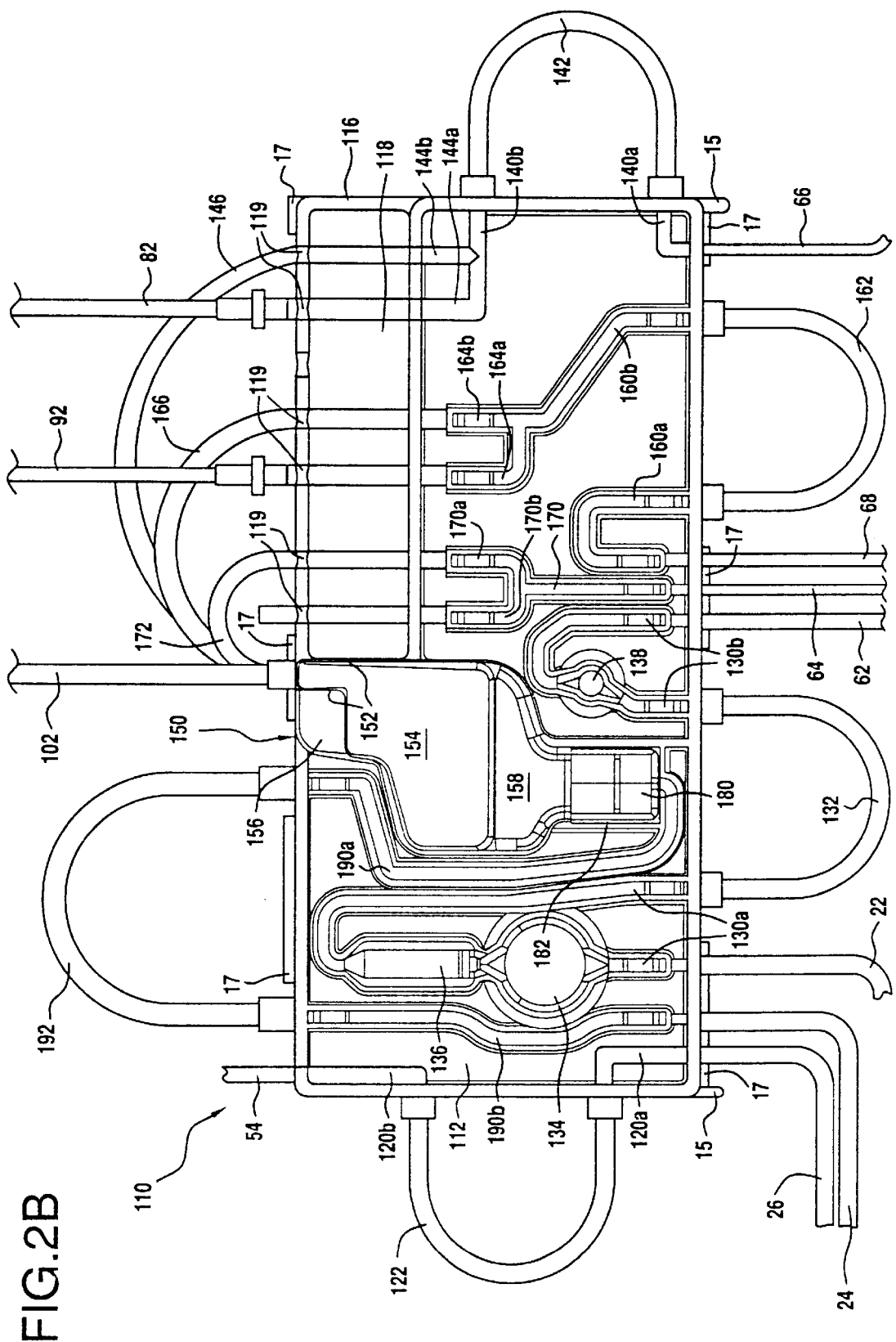

As illustrated in FIGS. 2A–2B, blood-primable extracorporeal tubing circuit 10 comprises a cassette assembly 110 and a number of tubing assemblies 20, 50, 60, 80, 90, 100 interconnected therewith. Generally, blood removal/return tubing assembly 20 provides a single needle interface between a donor/patient 4 and cassette assembly 110, and blood inlet/blood component tubing subassembly 60 provides the interface between cassette assembly 110 and blood processing vessel 352. An anticoagulant tubing assembly 50, platelet collection tubing assembly 80, plasma collection tubing assembly 90, and vent bag tubing subassembly 100 are also interconnected with cassette assembly 110. As will be appreciated, the extracorporeal tubing circuit 10 and blood processing vessel 352 are interconnected to combinatively yield a closed disposable for a single use.

The blood removal/return tubing assembly 20 includes a needle subassembly 30 interconnected with blood removal tubing 22, blood return tubing 24 and anticoagulant tubing 26 via a common manifold 28. The needle subassembly 30 includes a needle 32 having a protective needle sleeve 34 and needle cap 36, and interconnect tubing 38 between needle 32 and manifold 28. Needle subassembly 30 further includes a D sleeve 40 and tubing clamp 42 positioned about the interconnect tubing 38. Blood removal tubing 22 may be provided with a Y-connector 44 interconnected with a blood sampling subassembly 46.

Cassette assembly 110 includes front and back molded plastic plates 112 and 114 (see FIGS. 4A, 4B and 5) that are hot-welded together to define a rectangular cassette member 115 having integral fluid passageways. The cassette assembly 110 further includes a number of outwardly extending tubing loops interconnecting various integral passageways. The integral passageways are also interconnected to the various tubing assemblies.

Specifically, cassette assembly 110 includes a first integral anticoagulant passageway 120a interconnected with the anticoagulant tubing 26 of the blood removal/return tubing assembly 20. The cassette assembly 110 further includes a second integral anticoagulant passageway 120b and a pump-engaging, anticoagulant tubing loop 122 between the first and second integral anticoagulant passageways 120a, 120b. The second integral anticoagulant passageway 120b is interconnected with anticoagulant tubing assembly 50. The anticoagulant tubing assembly 50 includes a spike drip chamber 52 connectable to an anticoagulant source, anticoagulant feed tubing 54 and a sterilizing filter 56. During use, the anticoagulant tubing assembly 50 supplies anticoagulant to the blood removed from a donor/patient 4 to reduce or prevent any clotting in the extracorporeal tubing circuit 10.

Cassette assembly 110 also includes a first integral blood inlet passageway 130a interconnected with blood removal tubing 22 of the blood removal/return tubing assembly 20. The cassette assembly 110 further includes a second integral blood inlet passageway 130b and a pump-engaging, blood inlet tubing loop 132 between the first and second integral blood inlet passageways 130a, 130b. The first integral blood inlet passageway 130a includes a first pressure-sensing module 134 and inlet filter 136, and the second integral blood inlet passageway 130b includes a second pressure-sensing module 138. The second integral blood inlet passageway 130b is interconnected with blood inlet tubing 62 of the blood inlet/blood component tubing assembly 60.

Blood inlet tubing 62 is also interconnected with input port 392 of blood processing vessel 352 to provide whole blood thereto for processing, as will be described. To return separated blood components to cassette assembly 110, the blood inlet/blood component tubing assembly 60 further includes red blood cell(RBC)/plasma outlet tubing 64, platelet outlet tubing 66 and plasma outlet tubing 68 interconnected with corresponding outlet ports 492 and 520, 456, and 420 of blood processing vessel 352. The RBC/plasma outlet tubing 64 includes a Y-connector 70 to interconnect tubing spurs 64a and 64b. The blood inlet tubing 62, RBC/plasma outlet tubing 64, plasma outlet tubing 68 and platelet outlet tubing 66 all pass through first and second strain relief members 72 and 74 and a braided bearing member 76 therebetween. This advantageously allows for a sealless interconnection, as taught in U.S. Pat. No. 4,425,112. As shown, multi-lumen connectors 78 can be employed in the various tubing lines.

Platelet outlet tubing 66 of the blood input/blood component tubing assembly 60 includes a cuvette 65 for use in the detection of red blood cells (via an interfacing RBC spillover detector provided on blood component separation device 6) and interconnects with a first integral platelet passageway 140a of cassette assembly 110. As will be appreciated, a transparent member could alternatively be integrated into cassette assembly 110 in fluid communication with first integral platelet passageway 140a to interface with an RBC spillover detector.

The cassette assembly 110 further includes a pump-engaging, platelet tubing loop 142 interconnecting the first integral platelet passageway 140a and a second integral platelet passageway 140b. The second integral platelet passageway 140b includes first and second spurs 144a and 144b, respectively. The first spur 144a is interconnected with platelet collection tubing assembly 80.

The platelet collection tubing assembly 80 can receive separated platelets during operation and includes platelet collector tubing 82 and platelet collection bags 84 interconnected thereto via a Y-connector 86. Slide clamps 88 are provided on platelet collector tubing 82.

The second spur 144b of the second integral platelet passageway 140b is interconnected with platelet return tubing loop 146 of the cassette assembly 110 to return separated platelets to a donor/patient 4 (e.g., upon detection of RBC spillover during platelet collection). For such purpose, platelet return tubing loop 146 is interconnected to the top of a blood return reservoir 150 integrally formed by the molded front and back plates 112, 114 of cassette member 115. As will be further described, one or more types of uncollected blood components, collectively referred to as return blood, will cyclically accumulate in and be removed from reservoir 150 during use. Back plate 114 of the cassette member 115 also includes an integral frame corner 116 defining a window 118 through a corner of cassette member 115. The frame corner 116 includes keyhole recesses 119 for receiving and orienting the platelet collector tubing 82 and platelet return tubing loop 146 in a predetermined spaced relationship within window 118.

The plasma outlet tubing 68 of blood inlet/blood component tubing assembly 60 interconnects with a first integral plasma passageway 160a of cassette assembly 110. Cassette assembly 110 further includes a pump-engaging, plasma tubing loop 162 interconnecting the first integral plasma passageway 160a and a second integral plasma passageway 160b. The second integral plasma passageway 160b includes first and second spurs 164a and 164b. The first spur 164a is interconnected to the plasma collection tubing assembly 90.

The plasma collection tubing assembly 90 may be employed to collect plasma during use and includes plasma collector tubing 92 and plasma collection bag 94. A slide clamp 96 is provided on plasma collector tubing 92.

The second spur 164b of the second integral plasma passageway 160b is interconnected to a plasma return tubing loop 166 to return plasma to donor/patient 4. For such purpose, the plasma return tubing loop 166 is interconnected to the top of the blood return reservoir 150 of the cassette assembly 110. Again, keyhole recesses 119 in the frame 116 of cassette assembly 110 are utilized to maintain the plasma collector tubing 92 and plasma return tubing loop 166 in a predetermined spaced relationship within window 118.

The RBC/plasma outlet tubing 64 of the blood inlet/blood component tubing assembly 60 is interconnected with integral RBC/plasma passageway 170 of cassette assembly 110. The integral RBC/plasma passageway 170 includes first and second spurs 170a and 170b, respectively. The first spur 170a is interconnected with RBC/plasma return tubing loop 172 to return separated RBC/plasma to a donor/patient 4. For such purpose, the RBC/plasma return tubing loop 172 is interconnected to the top of blood return reservoir 150 of the cassette assembly 110. The second spur 170b may be closed off as shown, or may be connected with an RBC/plasma collection tubing assembly (not shown) for collecting RBC/plasma during use. The RBC/plasma return tubing loop 172 (and RBC/plasma collector tubing if provided) is maintained in a desired orientation within window 118 by keyhole recesses 119 of the frame 116.

Vent bag tubing assembly 100 is also interconnected to the top of blood return reservoir 150 of cassette assembly 110. The vent bag tubing assembly 100 includes vent tubing 102 and a vent bag 104. During use, sterile air present since packaging within cassette assembly 110, and particularly within blood return reservoir 150, cyclically passes into and back out of vent tubing 102 and vent bag 104, as will be further described.

Vent bag 104 may be provided with a sterile, gas pressure-relief valve at a top end (not shown). Further, it should be noted that, as opposed to vent bag tubing assembly 100, additional integral passageways, integrated chambers and tubing loops could be included in cassette assembly 110 to perform the same functions as the vent bag tubing assembly 100.

Figure 5:
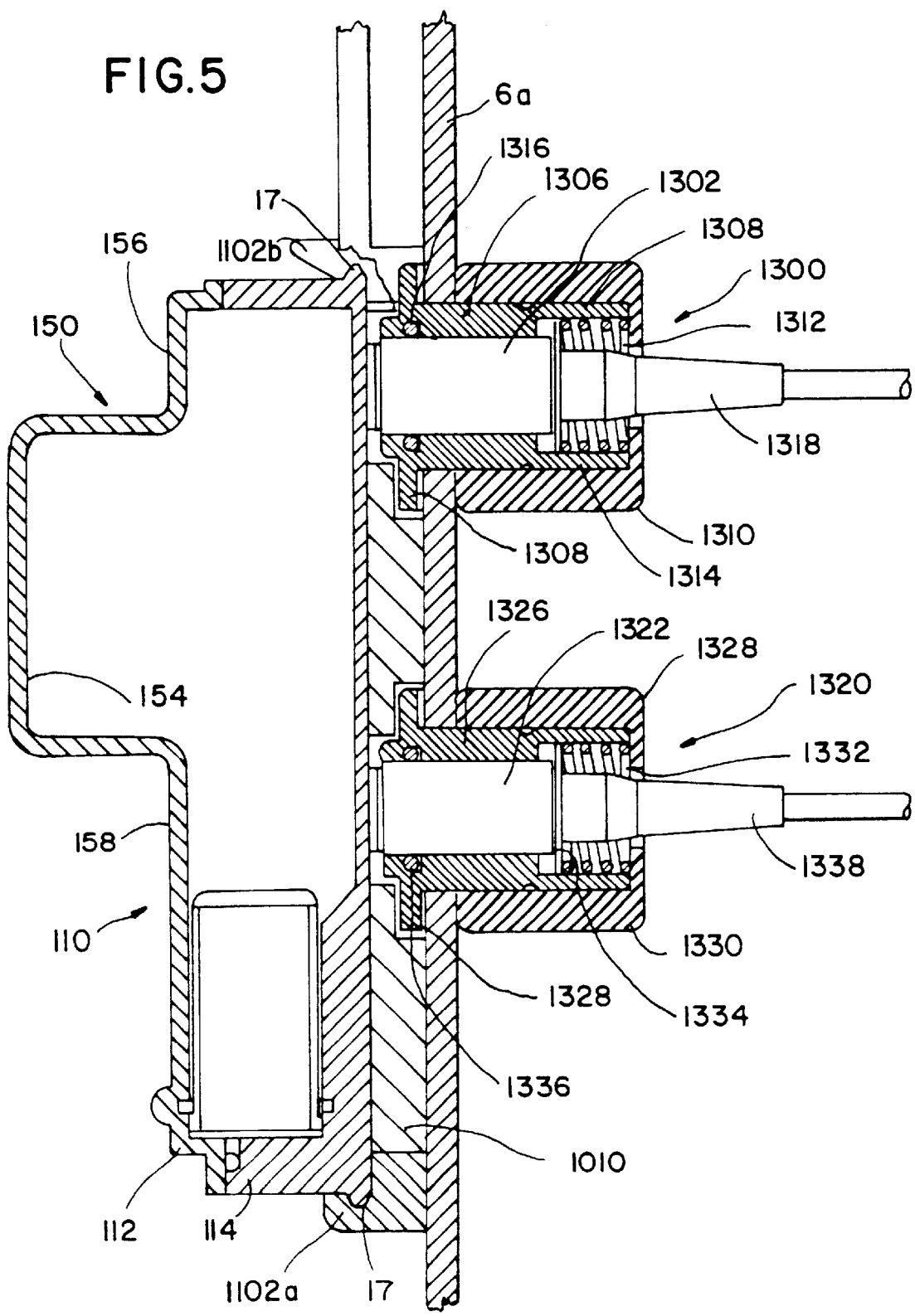
FIG. 5 is a cross-sectional side view of the upper and lower ultrasound sensors of the pump/valve/sensor assembly of FIG. 3 coupled with a reservoir of the cassette assembly of the extracorporeal tubing circuit of FIGS. 2A–2B.

The platelet return tubing loop 146, plasma return tubing loop 166 and RBC/plasma return tubing loop 172 are interconnected in a row to the top of blood return reservoir 150 immediately adjacent to forwardly projecting sidewalls 152 thereof so that the blood components returned thereby will flow down the inner walls of the blood return reservoir 150 The blood return reservoir 150 includes an enlarged, forwardly projecting mid-section 154, a reduced top section 156 and reduced bottom section 158 (see also FIG. 5). A filter 180 is disposed in a bottom cylindrical outlet 182 of the blood return reservoir 150.

A first integral blood return passageway 190a is interconnected to the outlet 182 of blood return reservoir 150, and is further interconnected to a second integral blood return passageway 190b via a pump-engaging, blood return tubing loop 192. The second integral blood return passageway 190b is interconnected with the blood return tubing 24 of the blood removal/return tubing assembly 20 to return blood to the donor/patient 4 via needle assembly 30.

As illustrated in FIGS. 2A–2B, pump-engaging tubing loops 122, 132, 142, 162 and 192 extend from cassette member 115 to yield an asymmetric arrangement thereby facilitating proper mounting of cassette assembly 110 on blood component separation device 6 for use. Relatedly, to further facilitate loading of cassette assembly 110, it is noted that the back plate 114 of cassette member 115 is preferably molded to present a shallow pan-shaped back having a rim extending around the entire periphery and around window 118, the edge of the rim being substantially coplanar with the back surface of the top, mid and bottom sections 154, 156, 158 of reservoir 150 and further defining a recessed region within which first and second pressure sensing modules 134 and 138 project.

Tubing assemblies 20, 50, 60, 80, 90 and 100 and cassette assembly 110 preferably comprise PVC tubing and plastic components that permit visual observation and monitoring of blood/blood components therewithin during use. Further, it should be noted that thin-walled PVC tubing (e.g., less than about 0.023 inch) may be advantageously employed for approved, sterile docking (i.e., the direct connection of two pieces of tubing) for platelet collector tubing 82 and plasma collector tubing 92 and RBC/plasma collector tubing, if provided. Thicker-walled PVC tubing (e.g., about 0.037 inch or more) is preferably utilized for pump-engaging tubing loops 132, 142, 162 and 192.

Pump/Valve/Sensor Assembly

Figure 3:
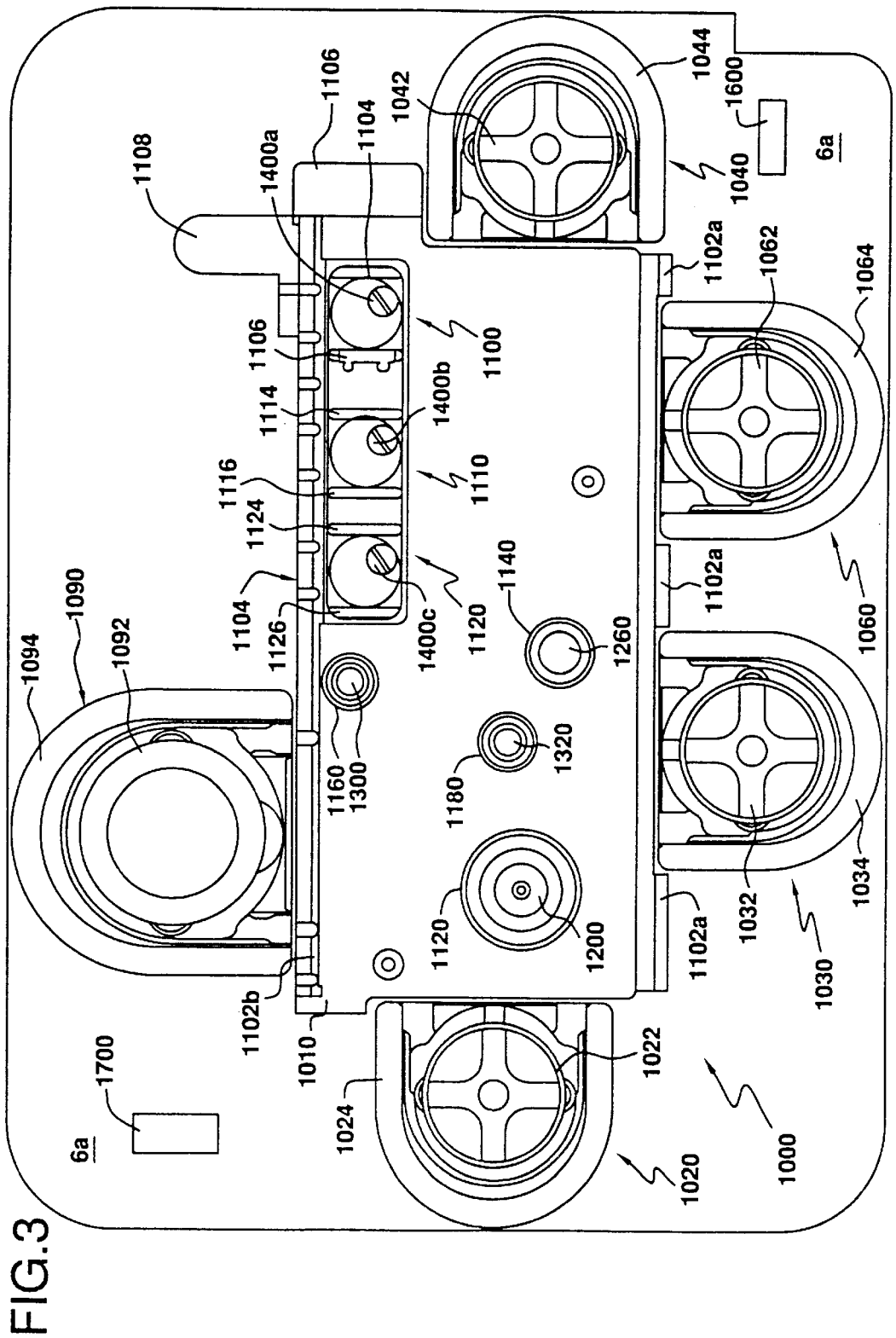
FIG. 3 is a front view of a pump/valve/sensor assembly for the system of FIG. 1.

As noted, cassette assembly 110 is mounted upon and operatively interfaces with the pump/valve/sensor assembly 1000 of blood component separation device 6 during use. The pump/valve/sensor assembly 1000 is angled upward at about 45° (see FIG. 1) and as illustrated in FIG. 3 includes a cassette mounting plate 1010, and a number of peristaltic pump assemblies, flow divert valve assemblies, pressure sensors and ultrasonic level sensors interconnected to face plate 6a of blood collection device 6 for pumping, controlling and monitoring the flow of blood/blood components through extracorporeal tubing circuit 10 during use.

More particularly, anticoagulant pump assembly 1020 is provided to receive anticoagulant tubing loop 122, blood inlet pump assembly 1030 is provided to receive blood inlet tubing loop 132, platelet pump assembly 1040 is provided to receive platelet tubing loop 142, plasma pump assembly 1060 is provided to receive plasma tubing loop 162, and blood return pump assembly 1090 is provided to receive blood return tubing loop 192. Each of the peristaltic pump assemblies 1020, 1030, 1040, 1060, and 1090 includes a rotor 1022, 1032, 1042, 1062 and 1092, and raceway 1024, 1034, 1044, 1064, and 1094 between which the corresponding tubing loop is positioned to control the passage and flow rate of the corresponding fluid.

Platelet divert valve assembly 1100 is provided to receive platelet collector tubing 82 and platelet return tubing loop 146, plasma divert valve assembly 1110 is provided to receive plasma collector tubing 92 and plasma return tubing loop 166, and RBC/plasma divert valve assembly 1120 is provided to receive RBC/plasma return tubing loop 172 and RBC/plasma collector tubing if provided. As noted above, each pair of tubing for collection or return of separated blood components is disposed in a predetermined spaced relationship within window 118 of cassette assembly 110, thereby facilitating loading relative to the corresponding divert value assemblies. As will be further described, platelet divert valve assembly 1100, plasma divert valve assembly 1110 and RBC/plasma divert valve assembly 1120 each include a rotary occluding member 1400a, 1400b and 1400c that is selectively positionable between stationary occluding walls 1104 and 1106, 1114 and 1116, and 1124 and 1126, respectively, for diverting fluid flow through one tubing of the corresponding pairs of tubings.

Pressure sensors 1200 and 1260 (See also FIGS. 4A and 4B) are provided within pump/valve/sensor assembly 1000 to operatively engage the first and second pressure-sensing modules 134 and 138 of cassette assembly 110 through openings 1120 and 1140 of cassette mounting plate 1100. Similarly, ultrasonic level sensors 1300 and 1320 (see also FIG. 5) are provided to operatively engage the blood return reservoir 150 cassette assembly 110 through openings 1160 and 1180 of cassette mounting plate 1100.

Figure 4B:
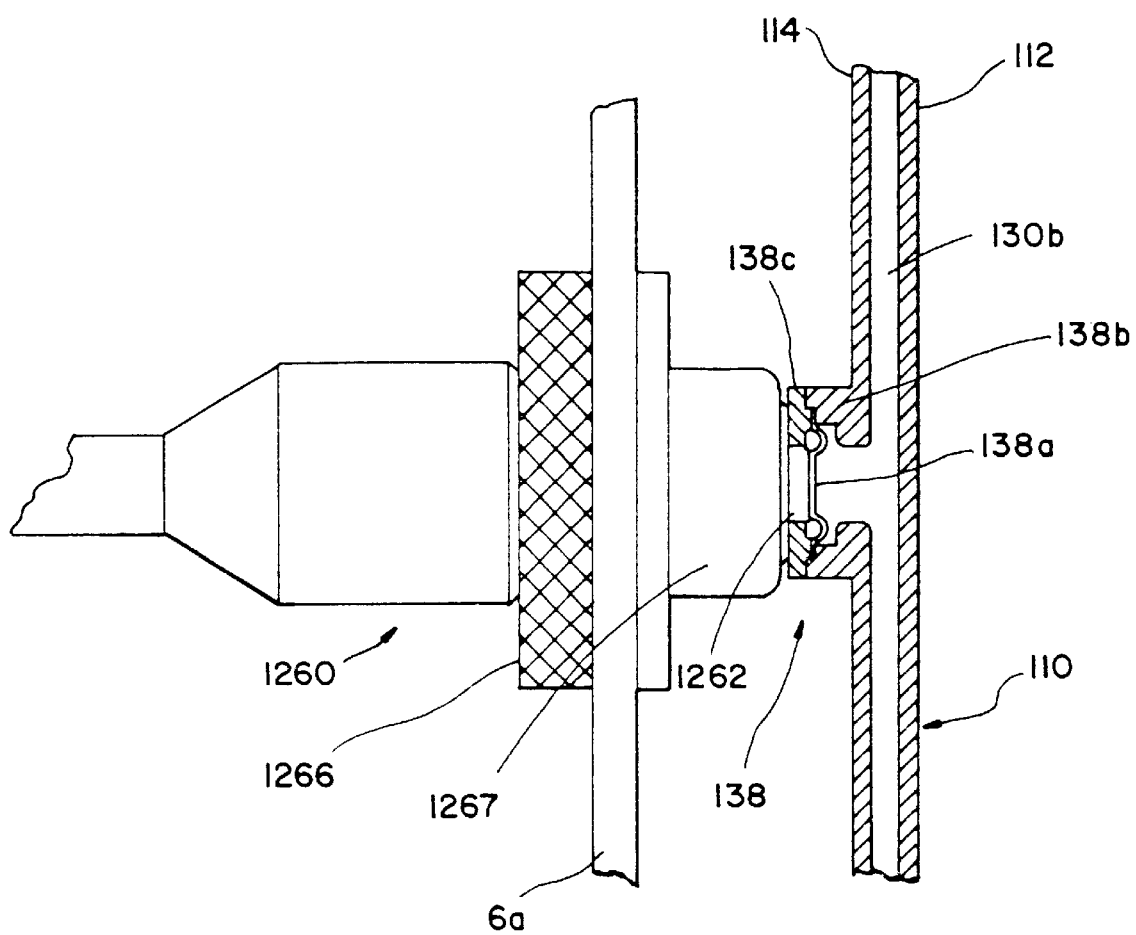

As shown in FIGS. 4A and 4B, the first and second pressure sensing modules 134, 138 of cassette assembly 110 each comprise a circular diaphragm 134a, 138a positioned on a raised cylindrical seat 134b, 138b formed into the back plate 114 of cassette assembly 110 with a ring-shaped, plastic diaphragm retainer 134c, 138c hot-welded to the raised cylindrical seats 134b, 138b to establish a seal therebetween. This arrangement allows the diaphragms 134a, 138b to be directly responsive to the fluid pressures within the first and second integral blood inlet passageways 130a, 130b, respectively, and pressure sensors 1200, 1260 to directly access the diaphragms 134a, 138a through the ring-shaped retainers 134c, 138c. By monitoring the diaphragms 134a, 138a, the pressure sensors 1200, 1260 can monitor the fluid pressure within the first and second integral blood inlet passageways 130a, 130b. In this regard, it should also be noted that since first integral blood inlet passageway 130a is in direct fluid communication with blood removal tubing 22, and since blood removal tubing 22 and blood return tubing 24 are fluidly interconnected via the common manifold 28, the first pressure sensing module 134 will be responsive to and first pressure sensor 1200 will actually sense the substantially common pressure in both the blood removal tubing 22 and blood return tubing 24 during operation.

With further regard to the first pressure sensing module 134 and first pressure sensor 1200, FIG. 4A illustrates an air coupling arrangement that allows for the sensing of positive and negative pressure changes (i.e., causing outward and inward flexure of diaphragm 134a). To achieve an air seal between the first pressure sensor 1200 and first pressure sensing module 134, the sensor 1200 includes a resilient (e.g., rubber), cone-shaped engaging member 1202. The engaging member 1202 is attached to an air channel member 1204 having a nipple-end 1206 that is received by beveled cylindrical extension 134d of retainer 134c. Air channel member 1204 further includes an outer, annular projecting channel portion 1208 that contains an O-ring 1210 for sealed sliding engagement of the air channel member 1204 within housing 1212. As illustrated, housing 1212 includes ears 1214 which interface with a floating positioning member 1216 secured to the face plate 6a of blood component separation device 6. As shown, a slight clearance is provided in such interface so as to permit slight lateral movement of the engaging member 1202 and air channel member 1204 during loading of the cassette assembly 110. A threaded end 1218 of housing 1212 extends through the face plate 6a of blood component separation device 6 and receives nut 1220 thereupon, while leaving a slight clearance between the nut 1220 and face plate 6a. A spring 1222 is positioned within the housing 1212 and acts upon the annular channel portion 1208 of the air channel member 1204 to provide a spring-loaded interface between the first pressure sensor 1200 and first pressure sensing module 134. Pressure sensing transducer 1224 engages air channel member 1204 to sense positive and negative pressure changes within sensing module 134 and provide an output signal in response thereto during use. As will be further described, the output signal of pressure transducer 1224 can be employed to control the operation of blood inlet pump 1030 and blood return pump 1090 during operation.

With regard to the second pressure sensing module 138 and the second pressure sensor 1260, FIG. 4B illustrates a direct contact coupling approach that allows for sensing of positive pressure changes (i.e., causing outward flexure of diaphragm 138a). Such contact coupling facilitates loading since the precise position of the diaphragm 138a relative to the second pressure sensor 1260 is not critical. As shown, second pressure sensor 1260 includes a projecting end portion 1262 that is received by the ring retainer 138c of sensing module 138 to directly contact diaphragm 138a. Pressure transducer 1264 is mounted relative to the face plate 6a of the blood component separation device 6 via a ring 1266 that threadingly engages a portion of pressure transducer 1264 extending through the face plate 6a. Pressure transducer 1264 provides an output signal responsive to positive pressure changes acting upon diaphragm 138a.

As shown in FIG. 5, when cassette assembly 110 is mounted on pump/valve/sensor assembly 1000, the ultrasonic level sensors 1300 and 1320 will be positioned to monitor the fluid level in the blood return reservoir 150. More particularly, upper ultrasonic level sensor 1300 will be positioned in contact with the reduced top section 156 of blood return reservoir 150 and lower ultrasonic level sensor 1320 will be positioned in contact with the reduced bottom section 158 of blood return reservoir 150.

Ultrasonic sensors 1300, 1320 each comprise pulse/echo transducers 1302, 1322 having a contact surface (e.g., urethane) 1304, 1324 that facilitates divert dry coupling (i.e., without a gel or other like coupling medium) with the blood return reservoir 150. By way of example, ultrasonic sensors may comprise model Z-11405 transducers offered by Zevex Inc. of 5175 Greenpine Drive, Salt Lake City, Utah. Pulse/echo transducers 1302, 1322 are disposed within housings 1306, 1326 for interconnection with face plate 6a of the blood component separation device 6. Housings 1306, 1326 include a flange 1308, 1328 for engaging the front of face plate 6a, and further include a threaded end 1308, 1328 that extends through the face plate 6a to receive corresponding retaining nuts 1310, 1330. A slight clearance is provided for between flanges 1308, 1328 and face plate 6a. Springs 1312, 1332 are positioned within housings 1306, 1326 to act upon the corresponding pulse/echo transducers 1302, 1332 via E-clips 1314, 1334 disposed therebetween. Such spring loading of pulse/echo transducers 1302, 1332 yields a predetermined desired loading pressure for pulse/echo transducers 1302, 1332 relative to reservoir 150 during operation (e.g., at least about 5 lbs.). O-rings 1316, 1336 are provided intermediate pulse/echo transducers 1302, 1322 and housings 1306, 1326 to provide a sliding seal therebetween. Cables 1318, 1338 are interconnected to transducers 1302, 1322 to provide pulsing signals and return detected echo signals.

By gauging the presence and timing of return ultrasonic echo pulses each of sensors 1300 and 1320 can be employed to monitor the presence or absence of fluid within their corresponding echo regions within the blood return reservoir 150, and permit blood component separation device 6 to provide pump control signals in response thereto. More particularly, when return blood accumulates up into the echo region of upper level sensor 1300 during blood processing, ultrasonic pulses emitted by upper level sensor 1300 will readily pass through the return blood and reflect off of the opposing reservoir outside sidewall/air interface to yield echo pulses having a predetermined minimum strength that are detected by upper sensor 1300 within a predetermined time period after transmission. When such echo pulses are received, upper sensor 1300 provides a signal that is used by blood component separation device 6 to initiate operation of blood return pump 1090 so as to remove accumulated return blood from the blood return reservoir 150 and transfer the same to the donor/patient 4.

When blood return pump 1090 has removed return blood from the reservoir 150 down into the lower echo region, ultrasonic pulses emitted by lower level sensor 1320 will not be reflected at the opposing reservoir outside sidewall/air interface to yield echo pulses having a predetermined minimum strength for detection by lower level sensor 1320 within a predetermined time period after transmission. When this occurs, lower level sensor 1320 will fail to provide corresponding signals to blood component separation device 6, and blood component separation device 6 will automatically stop blood return pump 1090 to stop further removal of return blood from the blood return reservoir 150, and return blood will again begin accumulating in reservoir 150. Thus, in the blood processing mode, blood component separation device 6 will not initiate operation of blood return pump 1090 unless and until it receives signals from upper ultrasonic sensor 1300 (the provisions of such signals indicating the presence of return blood in the upper echo region), and will thereafter automatically stop operation of blood return pump 1090 if it fails to receive signals from ultrasonic sensor 1320 (the failure to receive such signals indicating the absence of return blood in the lower echo region).

In an initial blood prime mode, whole blood is introduced to reservoir 150 from a donor/patient 4 through blood return tubing 24, integral passageways 190a, 190b, and tubing loop 192 via reverse operation of blood return pump 1090. When such whole blood accumulates up into the echo region of lower level sensor 1320, ultrasonic pulses emitted by lower level sensor 1320 will pass through the blood and reflect off of the opposing reservoir outside sidewall/air interface to yield echo pulses having a predetermined minimum strength that are detected by lower level sensor 1320 within a predetermined time period after transmission. When such echo pulses are received in the blood prime mode, lower level sensor 1320 provides a signal that is used by blood component separation device 6 to turn off blood return pump 1090 and end the blood prime mode. Blood component separation device 6 then initiates the blood processing mode.

It is contemplated that ultrasonic sensors 1300, 1320 can be utilized for indicating and/or confirming the desired mounting relationship of cassette member 15 on cassette mounting plate 1010 for blood processing operations. For such purposes, if the desired mounting has been achieved, the sensors 1300, 1320 should be coupled to reservoir 150 so that ultrasonic pulses reflect off the interface between the inside surface of the back sidewall of reservoir 150 (i.e., the sidewall contacted by the sensors 1300, 1320) and contained air within reservoir 150, and be received with a predetermined minimum strength within a predetermined time period after transmission. If such echo pulses are received with respect to both ultrasonic sensors 1300, 1320, the desired loading relationship will be indicated and/or confirmed. Further, it is noted that ultrasonic sensors 1300, 1320 may be employable to sense echo pulses from the interfaces between fluid contained within the reservoir 150 and the inside surface of the outer sidewall of reservoir 150 in the upper and lower echo regions of the reservoir during operation. If such echo pulses are detectable within corresponding, predetermined time windows, corresponding signals provided by ultrasonic sensors 1300, 1320 can provide a further input for blood component separation device 6 to control operation of blood return pump 1090.

It should be noted that in the illustrated arrangement, the upper and lower ultrasonic sensors 1300 and 1320 advantageously operate via coupling with reduced cross-sectional portions 156 and 158 of reservoir 150. The reduced upper and lower reservoir portions 154, 158,accommodate reliable detection of echo pulses when fluid is present in the upper and lower echo regions, and the enlarged mid-portion 158 provides satisfactory return blood holding capabilities.

Figure 6:
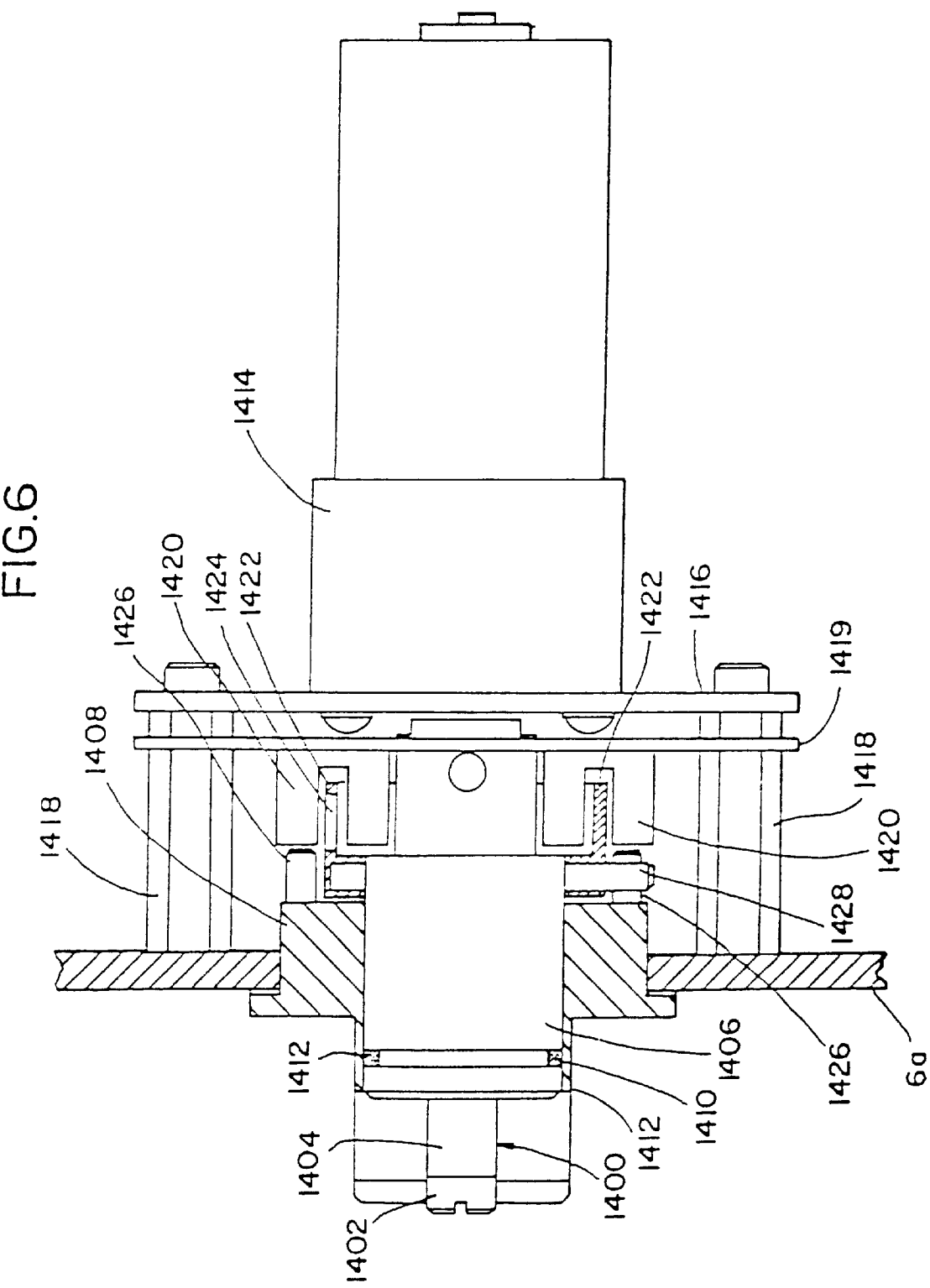
FIG. 6 is a cross-sectional side view of a platelet divert valve subassembly of the pump/valve/sensor assembly of FIG. 3.

FIG. 6 shows the components of each of the platelet divert valve subassembly 1100, plasma divert valve subassembly 1100 and RBC/plasma divert valve subassembly 1120. Each subassembly includes a rotary occluder member 1400 having a headed shaft member 1402 and barrel sleeve 1404 positioned thereupon and rotatable relative thereto. The subassembly further comprises a main valve shaft 1406 positioned within a valve body 1408 that is secured to face plate 6a of blood component separation device 6. An O-ring 1410 is provided in a recess on the main valve shaft 1406 to provide a sliding seal between main valve shaft 1406 and extensions 1412 of main valve body 1408. The main valve shaft 1406 is driven by a motor 1414 mounted on mount plate 1416 that in turn is mounted to and set off from face plate 6a by standoff legs 1418.

For positioning rotary occluder member 1400 for occlusion relative to one of the co-acting walls (e.g. 1104 or 1106 of the plasma divert valve subassembly 1100) or for loading/removal of the cassette assembly 110 on the blood component separation device 6, each divert valve subassembly comprises three optical through-beam sensors 1420 (two shown) interconnected to standoff legs 1418 via support layer 1419, and an optical interrupter member 1422 interconnected to the main valve shaft 1406. Each through-beam sensor 1420 is of a U-shape configuration with a radiation source and radiation receiver disposed on opposing legs. The optical interrupter member 1422 has an inverted cup configuration with its sidewalls interposed and rotatable between the opposing legs of sensors 1420. The optical interrupter member 1422 includes a single window 1424 therethrough. As will be appreciated, the position of the rotary occluder member 1400 relative to the window 1424 of the optical interrupter 1422 is known, such that when the optical window 1424 passes between the opposing radiation source/receiver for a given optical sensor 1420, the optical sensor 1420 will provide a signal in response to the through-beam (indicating the position of the rotary occluder member 1400), and the signal is employed to control the operation of motor 1414 to dispose rotary occluder member 1400 in the desired position. To provide/route such signals, the support layer 1419 may advantageously comprise a printed circuit board. Optical sensors 1420 are preferably positioned slightly "upstream" of predetermined stop regions for occlusion or cassette loading so that motor 1414 will be able to dynamically slow down and position rotary occluder member 1400 within such regions as desired. To insure the desired positioning for occlusion, however, stops 1426 are provided on main valve shaft 1406 to co-act with cross-pin 1428 interconnected to main valve shaft 1406 to insure stop positioning of rotary occluder member 1400 relative to the desired occluding wall.

Each of the occluding walls 1104 and 1106, 1114 and 1116, and 1124 and 1126, are provided with arcuate recesses (not shown) for receiving the rotatable barrel sleeve on 1404 of rotary occluder members 1400a, 1400b and 1400c. By way of example, such arcuate recesses may have an arc length of 20° and provide a tolerance range for positioning the rotary occluder members 1400a, 1400b, 1400c to achieve the desired tubing occlusion. As illustrated in FIG. 3, occluding wall 1106 may be provided with a resilient pad to best accommodate the use of approved, sterile-docking tubing for platelet collector tubing 82. Further, and as noted above, sterile-docking tubing may be advantageously employed for plasma collector tubing 92 and, if provided, RBC/plasma collector tubing (not shown), and corresponding resilient pads (not shown) may be provided on occluding walls 1114 and 1124. In this regard, given the thinness and relatively high-spring rate of sterile-docking tubing, the use of resilient pads in connection therewith increases the wearability of the sterile docking tubing.

In order to establish an initial predetermined set position of the cassette assembly 110 relative to the pump/valve/sensor assembly 1000, the cassette assembly 110 includes downwardly extending corner positioning tabs 15 and top and bottom edge lips 17 that engage corresponding lower channel projections 1102a on cassette mounting plate 1010 and upper channel projections 1102b on a pivotable spring-loaded interlock member 1104 that extends across the top edge of cassette mounting plate 1010. The interlock member 1104 is spring-loaded to positively engage cassette assembly 110 upon loading via a spring positioned within housing 1106, and is provided with a tab 1108 for pivotable movement during cassette loading against the spring loading pressure. Preferably, interlock member 1104 is disposed relative to the raceway 1094 of return pump assembly 1090, such that when cassette assembly 110 is fully loaded for operation on blood component separation device 6, raceway 1094 will physically restrict interlock member 1104 from being pivoted, thereby advantageously restricting removal and/or movement of cassette assembly 110 during use.

Figure 7:
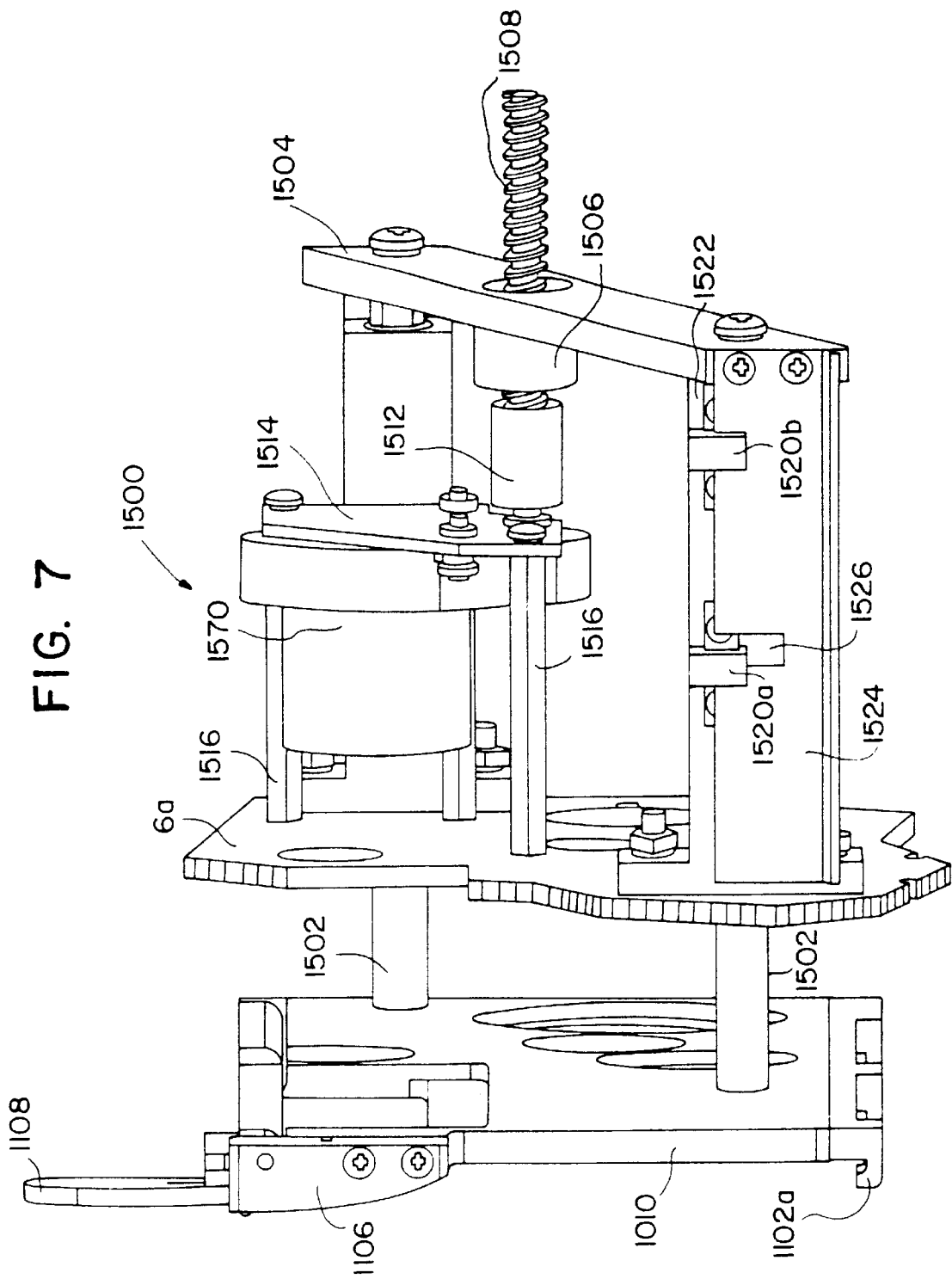
FIG. 7 is illustrates a loading assembly for a cassette mounting plate of the pump/valve/sensor assembly of FIG. 3.

After cassette assembly 110 has been secured on the cassette mounting plate 1010, a loading assembly 1500 retracts the cassette mounting plate 1010 towards face plate 6aof the blood component separation device 6 to establish the above-noted, fully-loaded pump, valve and sensor relationships. As illustrated in FIG. 7, loading assembly 1500 includes two posts 1502 upon which cassette mounting plate 1010 is supportably interconnected. The posts 1502 extend through the face plate 6a of blood collection device 6aand are interconnected to a cross-connect member 1504. A drive nut 1506 is secured to cross-connect member 1504 and engages a drive screw 1508. The drive screw 1508 is in turn rotatably interconnected to a drive motor 1510 via coupling 1512, the drive motor 1510 being mounted on a platform 1514 which is supportively interconnected to face plate 6a via standoff legs 1516. The drive motor 1510 operates to turn drive screw 1508 so as to cause cross-connect member 1504 and posts 1502 to selectively move cassette mounting plate 1010 perpendicularly towards face plate 6a during loading procedures and perpendicularly away from face plate 6a for unloading of the cassette assembly 110.

To establish the desired position of cassette mounting plate 1010, U-shaped optical through-beam sensors 1520a and 1520bare mounted on post bearing holders 1522 and an optical occluder member 1524 having a window 1526 is interconnected to the cross-connect member 1504. Each of the U-shaped optical sensors 1520a, 1520b includes a radiation source and radiation receiver positioned on opposing extending legs, and the optical occluder member 1524 extends between such legs. Since the relative positions between cassette mounting plate 1010 and optical sensors 1520a, 1520b are known, by detecting the passage of radiation through window 1526 using optical sensors 1520, and providing a signal responsive thereto,the position of cassette mounting plate 1010 for loading and unloading can be automatically established. For example, when a through-beam is received by optical sensor 1520b, a signal will be provided to stop motor 1510 in a position wherein cassette assembly 110 will be fully loaded on the pump/valve/sensor assembly 1000 for operation.

To confirm such loaded condition, first and second pressure sensors 1200 and 1260 and upper and lower ultrasonic sensors 1300 and 1320 may be employed. For example, predetermined minimum pressure values can be established and actual pressures measured for each of the first and second pressure sensors 1200 and 1260 to confirm the desired loading of cassette assembly 110. Further, and of particular interest, ultrasonic sensors 1300 and 1320 can be advantageously employed to confirm the desired loading, since upon proper coupling to reservoir 150 echo pulses should be reflected off of the internal sidewall/air interface with a predetermined minimum strength within a predetermined time period as noted above.

It should be noted that drive motor 1510 preferably includes a number of reduction gears with the last gear being operatively associated with a slip clutch plate to limit the maximum amount of force hat may be applied by cassette mounting plate 1010 (e.g., to an object between cassette mounting plate 1010 and face plate 6a). Relatedly, it is preferable to include control capabilities wherein during a load cycle if the window 1526 of optical occluder 1524 has not moved from its position within the first optical pass through sensor 1520a to a position within the second optical pass through sensor 1520b within a predetermined time period, drive motor 1510 will automatically either stop or reverse operations.

To summarize the loading process, loading assembly 1500 initially disposes cassette mounting plate 1010 in an extended position. With the cassette mounting plate 1010 in such extended position, interlock member 1104 is pivoted away from cassette mounting plate 1010 and cassette assembly 110 is positioned on cassette mounting plate 1010 with bottom edge lips 17 of cassette assembly 110 being received by lower channel projections 1102a of cassette mounting plate 1010 and, upon return pivotal movement of interlock member 1104, top edge lips 17 of cassette assembly 110 being engaged by upper channel projections 1102b on interlock member 1104. Loading assembly 1500 is then operated to retract cassette mounting plate 1010 from its extended position to a retracted position, wherein tubing loops 122, 132, 162, 142, 192 of cassette assembly 110 are automatically positioned within the corresponding peristaltic pump assemblies 1020, 1030, 1060, 1040 and 1090. For such purposes, the rotors of each of the peristaltic pump assemblies are also operated to achieve loaded positioning of the corresponding tubing loops. Further, it should be noted that for loading purposes, the rotary occluder members 1400a, 1400b and 1400c of the divert valve assemblies 1100, 1110 and 1120 are each positioned in an intermediate position so as to permit the corresponding sets of tubing to be positioned on each side thereof.

Upon retraction of the cassette mounting plate 1010, spring-loaded, ultrasonic sensors 1300 and 1320 will automatically be coupled to reservoir 150 and first and second pressure sensors 1200 and 1260 will automatically couple to first and second pressure sensing modules 134 and 138 of cassette assembly 110. In this fully-loaded, retracted position, the cassette assembly 110 will be restricted from movement or removal by the above-noted physical restriction to pivotal movement of interlock member 1104 provided by raceway 1094 of return pump assembly 1090.

It is also noted that during loading of cassette assembly 110 on the blood component separation device 6, cuvette 65 is positioned within an RBC spillover detector 1600 (e.g., an optical sensor for detecting the presence of any red blood cells in the separated platelet fluid stream and providing a signal response thereto) provided on the face plate 6a. Similarly, a portion of anticoagulant tubing 54 is positioned within an AC sensor 1700 (e.g., an ultrasonic sensor for confirming the presence of anticoagulant and providing a signal in the absence thereof) also provided in face plate 6a.

To unload cassette assembly 110 after use, the occluding members 1400a, 1400b and 1400c of each divert value assembly are again positioned in an intermediate position between the corresponding occluding walls and loading assembly 1500 is operated to move cassette mounting plate 1010 from its retracted position to its extended position. Contemporaneously, the rotors of the various peristaltic pump assemblies are operated to permit the corresponding tubing loops to exit the same. In the extended position, the interlock member 1104 is pivoted out of engagement with cassette assembly 110 and cassette assembly 110 is removed and disposed of.

Operation of Extracorporeal Tubing Circuit and Pump/Valve/Sensor Assembly

In an initial blood prime mode of operation, blood return pump 1090 is operated in reverse to transfer whole blood through blood removal/return tubing assembly 20, integral blood return passageway 190, blood return tubing loop 192 and into reservoir 150. Contemporaneously and/or prior to the reverse operation of blood return pump 1090, anticoagulant peristaltic pump 1020 is operated to prime and otherwise provide anticoagulant from anticoagulant tubing assembly 50, through anticoagulant integral passageway 120, and into blood removal tubing 22 and blood return tubing 24 via manifold 28. When lower level ultrasonic sensor 1320 senses the presence of the whole blood in reservoir 150 a signal is provided and blood component separation device 6 stops blood return peristaltic pump 1090. As will be further discussed, during the blood prime mode blood inlet pump 1030 is also operated to transfer blood into blood inlet integral passageway 130, through blood inlet tubing loop 132 and into blood inlet/blood component tubing assembly 60 to prime the blood processing vessel 352.

During the blood prime mode, vent bag assembly 100 receives air from reservoir 150. Relatedly, the occluding members 1400a, 1400b, 1400c of divert assemblies 1100, 1110, 1120 are each preferably positioned to divert flow to the reservoir 150. It should also be noted that to facilitate blood priming, the cassette assembly 110 is angled upward at about 45° in its loaded position, and the integral passageways of cassette member 115 are disposed so that all blood and blood component inlet paths provide for a bottom-to-top plug flow.

In the blood processing mode, the blood inlet peristaltic pump 1030, platelet peristaltic pump 1040 and plasma peristaltic pump 1060 are operated continuously, and the occluding members 1400*a*, 1400*b*, 1400*c* are positioned for collection or return of corresponding blood components, as desired. During a blood removal submode, blood return peristaltic pump 1090 is not operated so that whole blood will pass into blood removal/return tubing assembly 20 and transferred to processing vessel 352 via the cassette assembly 110 and blood inlet/blood component tubing assembly 60. In the blood removal submode, uncollected blood components are transferred from the processing vessel 352 to cassette assembly 110, and uncollected components are passed into and accumulate in reservoir 150 up to a predetermined level at which upper level ultrasonic sensor 1300 provides signals used by blood component separation device 6 to end the blood removal submode and initiate a blood return submode. More particularly, blood return submode is initiated by forward operation of blood return peristaltic pump 1090. In this regard, it should be appreciated that in the blood return submode the volume transfer rate of return blood through blood return tubing loop 192 utilizing blood return peristaltic pump 1090 is established by blood component separation device 6, according to a predetermined protocol, to be greater than the volume transfer rate through blood inlet tubing loop 132 utilizing blood inlet peristaltic pump 1030. As such, the accumulated blood in reservoir 150 is transferred into the blood return tubing of blood removal/return tubing assembly 20 and back into the donor/patient 4. During the blood processing mode, when the accumulated return blood in reservoir 150 is removed down to a predetermined level, lower level ultrasonic sensor 1320 will fail to provide signals to blood component separation device 6, whereupon blood component separation device 6 will automatically stop blood return peristaltic pump 1090 to end the blood return submode. This automatically serves to reinitiated the blood removal submode since blood inlet peristaltic pump 1030 continuously operates.

During the blood processing mode, pressure sensor 1200 senses negative/positive pressure changes within the blood removal tubing 22 blood return tubing 26, via first integral blood inlet passageway 130*a*. Such monitored pressure changes are communicated to blood component separation device 6 which in turn controls blood inlet pump 1030 and return pump 1090 so as to maintain fluid pressures within predetermined ranges during the blood removal and the blood return submodes. Specifically during the blood removal submode, if a negative pressure is sensed that exceeds (i.e., is less than) a predetermined negative limit value, then blood component separation device 6 will slow down operation of blood inlet pump 1030 until the sensed negative pressure is back within an acceptable range. During the blood return submode, if a positive pressure is sensed that exceeds (i.e., is greater than) a predetermined positive limit value, then blood component separation device 6 will slow down operation of blood return pump 1090 until the sensed positive pressure is back within an acceptable range.

Pressure sensor 1260 monitors the positive pressure within the second integral blood inlet passageway 130*b* and blood inlet tubing 62. If such sensed positive pressure exceeds a predetermined maximum value, blood component separation device 6 will initiate appropriate responsive action, including, for example, slowing or stoppage of the centrifuge and peristaltic pumps.

During the blood processing mode, blood component separation device 6 controls the operation of anticoagulant pump 1020 according to a predetermined protocol and responsive to signals provided by AC sensor 1700 (e.g., indicating a depleted anticoagulant source). Also, blood component separation device 6 also controls the operation of divert assemblies 1100, 1110, 1120 according to predetermined instructions and further pursuant to any detect signals provided by RBC spillover detector 1600. In the latter regard, if an RBC spillover in the separated platelet stream is detected, blood component separation device 6 will automatically cause occluder member 1400*a* to divert the separated platelet stream to the return reservoir 150 until the RBC spillover has cleared, thereby keeping red blood cells from undesirably passing into platelet collector tubing assembly 80.

In normal operation, whole blood will pass through needle assembly 30, blood removal tubing 22, cassette assembly 110 and blood inlet tubing 62 to processing vessel 352. As will be further described in detail, the whole blood will then be separated in vessel 352. A platelet stream will pass out of port 420 of the vessel, through platelet tubing 66, back through cassette assembly 110, and will then be either collected in collector assembly 80 or diverted to reservoir 150. Similarly, separated plasma will exist vessel 352 through port 456 to plasma tubing 68 back through cassette assembly 110, and will then either be collected in platelet tubing assembly 90 or diverted to reservoir 150. Further, red blood cells and plasma (and potentially white blood cells) will pass through ports 492 and 520 of vessel 352 through RBC/plasma tubing 64, through cassette assembly 110 and into reservoir 150. In this regard, it is contemplated that second spur 170*b* of integral passageway 170 may be connected to a separate RBC/plasma collector tubing assembly (not shown) and RBC/plasma divert valve assembly 1120 could be operated for the collection of RBC/plasma.

As noted above, when uncollected platelets, plasma, and RBC/plasma (and potentially white blood cells) have accumulated in reservoir 150 up to upper ultrasonic level sensor 1300, operation of return peristaltic pump 1090 will be initiated to remove the noted components from reservoir 150 and transfer the same back to the donor/patient 4 via the return tubing 24 and needle assembly 20. When the fluid level in the reservoir 150 drops down to the level of the lower ultrasonic level sensor 1320, the return peristaltic pump 1090 will automatically turn off reinitiating the blood removal submode. The cycle between blood removal and blood return submodes will then continue until a predetermined amount of platelets or other collected blood components have been harvested.

In one embodiment, reservoir 150 and upper and lower ultrasonic sensors 1300 and 1320 are provided so that, during the blood processing mode, approximately 50 milliliters of return blood will be removed from reservoir 150 during each blood return submode and accumulated during each blood removal submode. Relatedly, in such embodiment, lower and upper level triggering by ultrasonic sensors 1300 and 1320 occurs at fluid volumes of about 15 milliliters and 65 milliliters, respectively, within reservoir 150. For such embodiment, it is also believed desirable to provide for a volume transfer operating rate range of about 30 to 300 milliliters/minute through blood return tubing loop 192 utilizing return pump 1090, and a volume transfer operating rate range of about 20 to 140 milliliters/minute through blood inlet tubing loop 132 utilizing inlet pump 1030. Additionally, for such embodiment a negative pressure limit of about −250 mmHg and positive pressure limit of about 350 mmHg is believed appropriate for controlling the speed of inlet pump 1030 and return pump 1090, respectively, in response to the pressures sensed in first pressure sensing module 134. A positive pressure limit of about 1350 mmHg within second sensing module 138 is believed appropriate for triggering slow-down or stoppage of the centrifuge and pumps.

Channel Housing

The channel assembly 200 is illustrated in FIGS. 8–23B and includes a channel housing 204 which is disposed on the rotatable centrifuge rotor assembly 568 (FIGS. 1 and 24) and which receives a disposable blood processing vessel 352. Referring more specifically to FIGS. 8–15, the channel housing 204 has a generally cylindrically-shaped perimeter 206 with a diameter of preferably no more than about 10 inches to achieve a desired size for the blood component separation device 6 (e.g., to enhance its portability). An opening 328 extends longitudinally through the channel housing 204 and contains an axis 324 about which the channel housing 204 rotates. The channel housing 204 may be formed from materials such as delrin, polycarbonate, or cast aluminum and may include various cut-outs or additions to achieve weight reductions and/or rotational balance.

Figure 15:
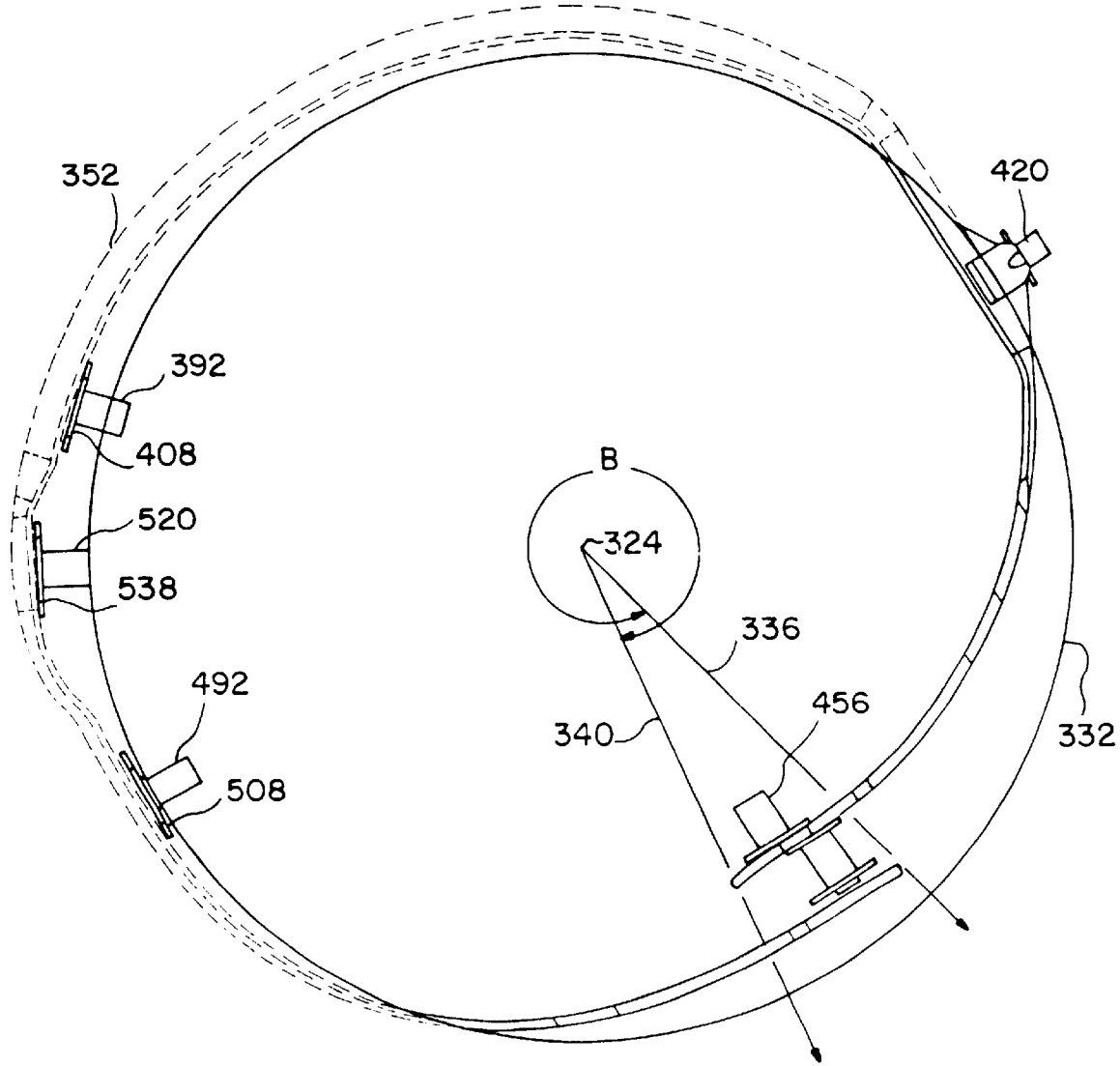
FIG. 15 is a top view of the channel of FIG. 8 illustrating the ratio of the plasma volume to the red blood cell volume.

The primary function of the channel housing 204 is to provide a mounting for the blood processing vessel 352 such that the blood may be separated into the blood component types in a desired manner. In this regard, the channel housing 204 includes a generally concave channel 208 in which the blood processing vessel 352 is positioned. The channel 208 is principally defined by an inner channel wall 212, an outer channel wall 216 which is radially spaced from the inner channel wall 212, and a channel base 220 which is positioned therebetween. The channel 208 also extends from a first end 284 generally curvilinearly about a rotational axis 324 of the channel housing 204 to a second end 288 which overlaps with the first end 284 such that a continuous flow path is provided about the rotational axis 324. That is, the angular disposition between the first end 284 of the channel 208 and the second end 288 of the channel 208 is greater than 360° and up to about 390°, and in the illustrated embodiment is about 380°. Referring to FIG. 15, this angular disposition is measured by the angle β, along a constant radius arc, between a first reference ray 336 which extends from the rotational axis 324 to the first end 284, and a second reference ray 340 which extends from the rotational axis 324 to the second end 288 of the channel 208.

The blood processing channel vessel 352 is disposed within the channel 208. Generally, the channel 208 desirably allows blood to be provided to the blood processing vessel 352 during rotation of the channel housing 204, to be separated into its various blood component types by centrifugation, and to have various blood component types removed from the blood processing vessel 352 during rotation of the channel housing 204. For instance, the channel 208 is configured to allow for the use of high packing factors (e.g., generally a value reflective of how "tightly packed" the red blood cells and other blood component types are during centrifugation and as will be discussed in more detail below). Moreover, the channel 208 also desirably interacts with the blood processing vessel 352 during centrifugation (e.g., by retaining the blood processing vessel 352 in the channel 208 and by maintaining a desired contour of the blood processing vessel 352). In addition, the channel 208 allows for a blood priming of the blood processing vessel 352 (i.e., using blood as the first liquid which is provided to the blood processing vessel 352 in an apheresis procedure).

The above-identified attributes of the channel 208 are provided primarily by its configuration. In this regard, the channel housing 204 includes a blood inlet slot 224 which is generally concave and which intersects the channel 208 at its inner channel wall 212 in substantially perpendicular fashion (e.g., the blood inlet slot 224 interfaces with the inner channel wall 212). A blood inlet port assembly 388 to the interior of the blood processing vessel 352 is disposed in this blood inlet slot 224 such that blood from the donor/patient 4 may be provided to the blood processing vessel 352 when in the channel 208. In order to retain a substantially continuous surface along the inner channel wall 212 during an apheresis procedure and with the blood processing vessel 352 being pressurized, namely by reducing the potential for the blood inlet port assembly 388 deflecting radially inwardly within the blood inlet slot 224, a recess 228 is disposed on the inner channel wall 212 and contains the end of the blood inlet slot 224 (e.g., FIG. 14A). This recess 228 receives a shield 408 which is disposed about the blood inlet port assembly 388 on the exterior surface of the blood processing vessel 352 as will be discussed in more detail below.

Figure 8:
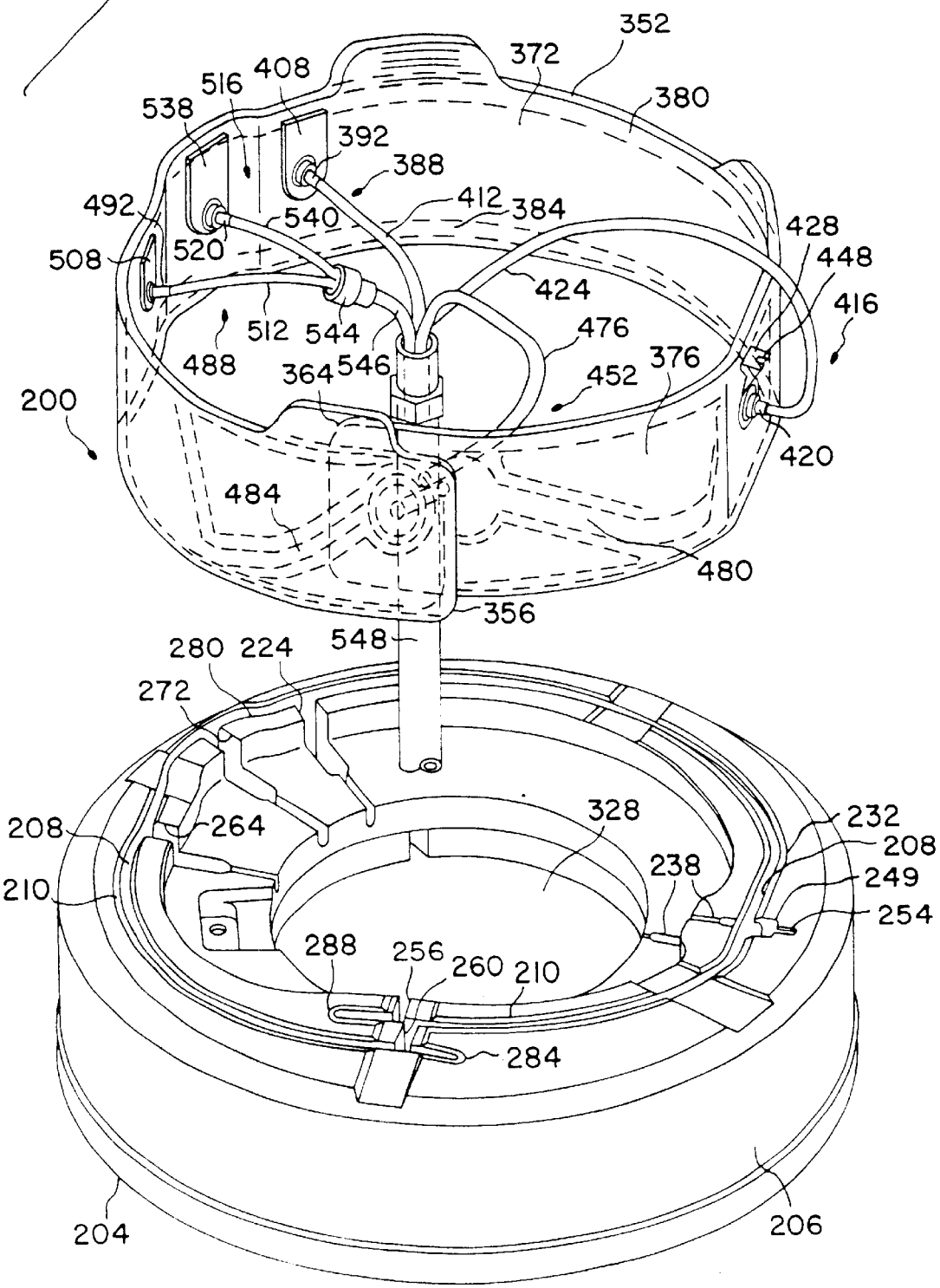
FIG. 8 is an exploded, perspective view of the channel assembly from the system of FIG. 1.
Figure 9:
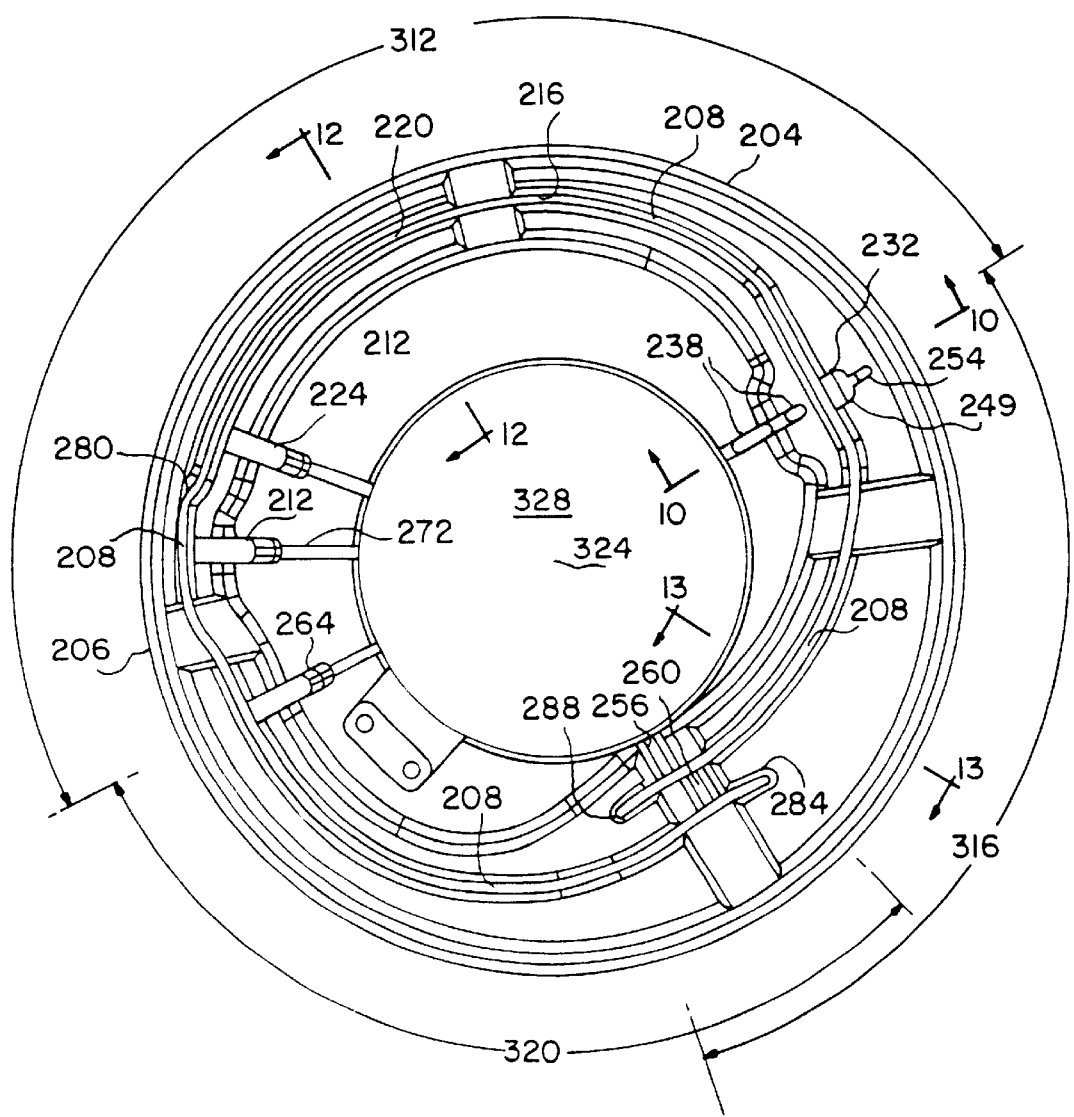
Figure 10:
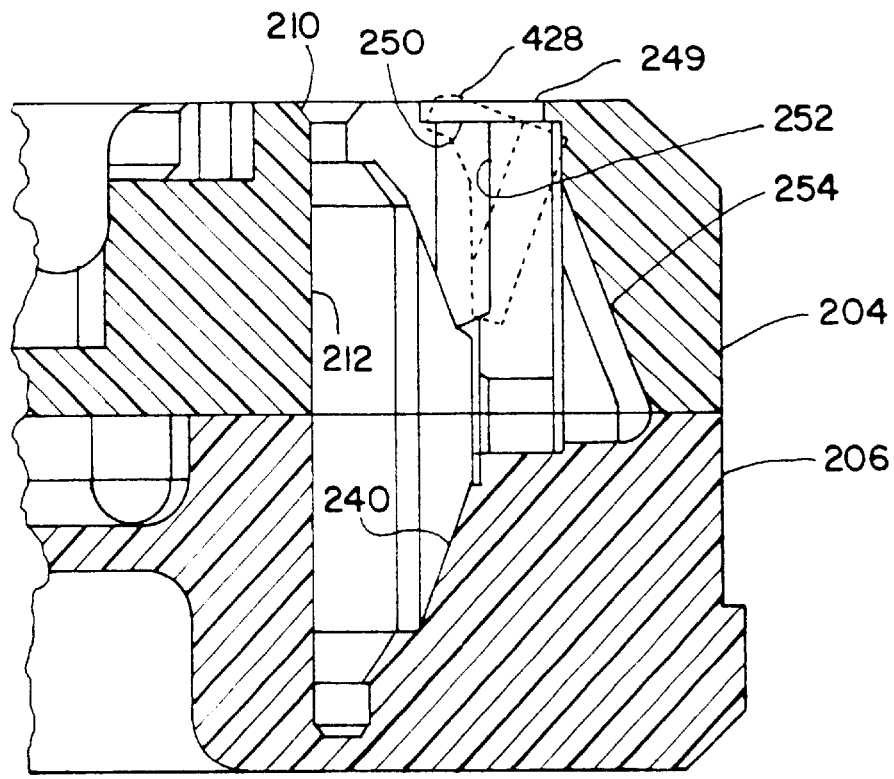
FIG. 10 is a cross-sectional view taken along line 10—10 of FIG. 9.
Figure 11A:
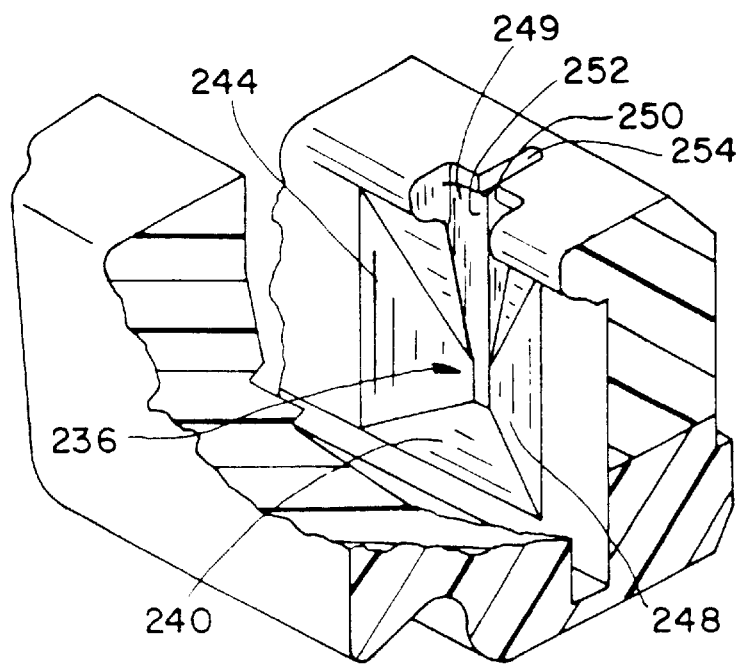
FIG. 11A is a cutaway, perspective view of the platelet collect well region of the channel housing of FIG. 8.
Figure 11B:
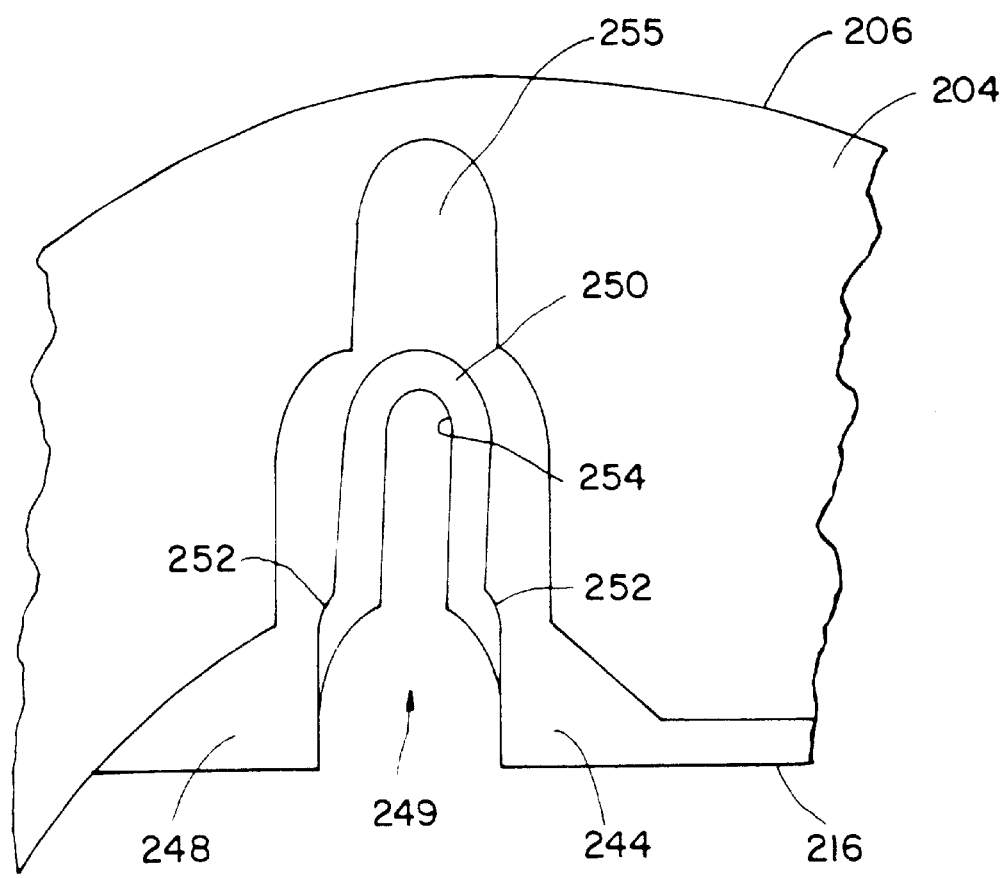
FIG. 11B is a lateral cutaway view, looking upwardly of the platelet collect well region of the channel housing of FIG. 8.

As illustrated in FIGS. 8–9, an RBC dam 232 of the channel 208 is disposed in a clockwise direction from the blood inlet slot 224 and whose function is to preclude RBCs and other large cells such as WBCs from flowing in a clockwise direction beyond the RBC dam 232. Generally, the surface of the RBC dam 232 which interfaces with the fluid containing volume of the blood processing vessel 352 may be defined as a substantially planar surface or as an edge adjacent the collect well 236. At least in that portion of the channel 208 between the blood inlet port 224 and the RBC dam 232, blood is separated into a plurality of layers of blood component types including, from the radially outermost layer to the radially innermost layer, red blood cells ("RBCs"), white blood cells ("WBCs"), platelets, and plasma. The majority of the separated RBCs are removed from the channel 208 through an RBC outlet port assembly 516 which is disposed in an RBC outlet slot 272 associated with the channel 208, although at least some RBCs may be removed from the channel 208 through a control port assembly 488 which is disposed in a control port slot 264 associated with the channel 208.

The RBC outlet port slot 272 is disposed in a counterclockwise direction from the blood inlet slot 224, is generally concave, and intersects the channel 208 at its inner channel wall 212 in substantially perpendicular fashion (e.g., the RBC outlet slot 272 interfaces with the inner channel wall 212). An RBC outlet port assembly 516 to the interior of the blood processing vessel 352 is disposed in this RBC outlet slot 272 such that separated RBCs from the apheresis procedure may be continually removed from the blood processing vessel 352 when in the channel 208 (e.g., during rotation of the channel housing 204). In order to retain a substantially continuous surface along the inner channel wall 212 during an apheresis procedure and with the blood processing vessel 352 being pressurized, namely by reducing the potential for the RBC outlet port assembly 516 deflecting radially inwardly within the RBC outlet slot 272, a recess 276 is disposed on the inner channel wall 212 and contains the end of the RBC outlet slot 272 (e.g., FIGS. 14A, 14B). This recess 276 receives a shield 538 which is disposed about the RBC outlet port assembly 516 on the exterior surface of the blood processing vessel 352 as will be discussed in more detail below.

The control port slot 264 is disposed in a counterclockwise direction from the RBC outlet slot 272, is generally concave, and intersects the channel 208 at its inner channel wall 212 in substantially perpendicular fashion (e.g., the control port slot 264 interfaces with the inner channel wall 212). A control port assembly 488 to the interior of the blood processing vessel 352 is disposed in the control port slot 264 (e.g., FIGS. 14A and C). In order to retain a substantially continuous surface along the inner channel wall 212 during an apheresis procedure and with the blood processing vessel 352 being pressurized, namely by reducing the potential for the control port assembly 488 deflecting radially inwardly within the control port slot 264, a recess 268 is disposed on the inner channel wall 212 and contains the end of the control port slot 264. This recess 268 receives a shield 508 which is disposed about the control port assembly 488 on the exterior surface of the blood processing vessel 352 as will be discussed in more detail below.

The portion of the channel 208 extending between the control port slot 264 and the RBC dam 232 may be characterized as the first stage 312 of the channel 208. The first stage 312 is configured to remove primarily RBCs from the channel 208 by utilizing a reverse flow in relation to the flow of platelet-rich plasma through the channel 208 which is in a clockwise direction. In this regard, the outer channel wall 216 extends along a curvilinear path from the RBC dam 232 to the blood inlet slot 224 generally progressing outwardly away from the rotational axis 324 of the channel housing 204. That is, the radial disposition of the outer channel wall 216 at the RBC dam 232 is less than the radial disposition of the outer channel wall 216 at the blood inlet slot 224. The portion of the RBC outlet slot 272 interfacing with the channel 208 is also disposed more radially outwardly than the portion of the blood inlet slot 224 which interfaces with the channel 208.

In the first stage 312, blood is again separated into a plurality of layers of blood component types including, from the radially outermost layer to the radially innermost layer, red blood cells ("RBCs"), white blood cells ("WBCs"), platelets, and plasma. As such, the RBCs sediment against the outer channel wall 216 in the first stage 312. By configuring the RBC dam 232 such that it is a section of the channel 210 which extends further inwardly toward the rotational axis 324 of the channel housing 204, this allows the RBC dam 232 to retain separated RBCs and other large cells as noted within the first stage 312. That is, the RBC dam 232 functions to preclude RBCs from flowing in a clockwise direction beyond the RBC dam 232.

Separated RBCs and other large cells as noted are removed from the first stage 312 utilizing the above-noted configuration of the outer channel wall 216 which induces the RBCs and other large cells as noted to flow in a counterclockwise direction (e.g., generally opposite to the flow of blood through the first stage 312). Specifically, separated RBCs and other large cells as noted flow through the first stage 312 along the outer channel wall 216, past the blood inlet slot 224 and the corresponding blood inlet port assembly 388 on the blood processing vessel 352, and to an RBC outlet slot 272. In order to reduce the potential for counterclockwise flows other than separated RBCs being provided to the control port assembly 488 disposed in the control port slot 264 (e.g., such that there is a sharp demarcation or interface between RBCs and plasma proximate the control port slot 264 as will be discussed in more detail below), a control port dam 280 of the channel 208 is disposed between the blood inlet slot 224 and the RBC outlet slot 272. That is, preferably no WBCs nor any portion of a buffy coat, disposed radially adjacent to the separated RBCs, is allowed to flow beyond the control port dam 280 and to the control port slot 264. The "buffy coat" includes primarily WBCs, lymphocytes, and the radially outwardmost portion of the platelet layer. As such, substantially only the separated RBCs and plasma are removed from the channel 208 via the RBC control slot 264 to maintain interface control as noted.

The flow of RBCs to the control port assembly 488 is typically relatively small. Nonetheless, the ability for this flow is highly desired in that the control port assembly 488 functions in combination with the RBC outlet port assembly 516 to automatically control the radial position of an interface between separated RBCs and the "buffy coat" in relation to the RBC dam 232 by controlling the radial position of an interface between separated RBCs and plasma in relation to the control port assembly 488. The control port assembly 488 and RBC outlet port assembly 516 automatically function to maintain the location of the interface between the separated RBCs and the buffy coat at a desired radial location within the channel 208 which is typically adjacent the RBC dam 232 such that there is no spillover of RBCs or the buffy coat beyond the RBC dam 232. This function is provided by removing separated RBCs from the channel 208 at a rate which reduces the potential for RBCs and the other large cells as noted flowing beyond the RBC dam 232 and contaminating the platelet collection.

Separated platelets, which are disposed radially inwardly of the RBC layer and more specifically radially inwardly of the buffy coat, flow beyond the RBC dam 232 with the plasma (e.g., via platelet-rich plasma) in a clockwise direction. A generally funnel-shaped platelet collect well 236 is disposed in a clockwise direction from the RBC dam 232 and is used to remove platelets from the channel 208 in the platelet-rich plasma. The configuration of the platelet collect well 236 is defined by only part of the outer channel wall 216. The portion of the platelet collect well 236 defined by the configuration of the outer channel wall 216 includes a lower face 240, a left side face 244, and a right side face 248. These faces 240, 244, 248 are each substantially planar surfaces and taper generally outwardly relative to the rotational axis 324 and inwardly toward a central region of the platelet collect well 236.

The remainder of the platelet collect well 236 is defined by the blood processing vessel 352 when loaded in the channel 208, namely a generally triangularly-shaped 428 which is disposed above the platelet outlet port assembly 416 to the interior of the blood processing vessel 352 and discussed in more detail below. A platelet support recess 249 extends further radially outwardly from those portions of the platelet collect well 236 defined by the configuration of the outer channel wall 216 and primarily receives the support 428 associated with the platelet collect port assembly 416. Generally, the upper portion of the support 428 is disposed below and engages an upper lip 252 of the platelet support recess 249, while portions of the fourth face 444 of the support 428 are seated against the two displaced shoulders 252. This positions the support 428 when the blood processing vessel 352 is pressurized to direct platelets toward the platelet collect port assembly 416.

The outer channel wall 216 is further configured to receive the platelet collect tube 424. An upper platelet collect tube recess 254 and a lower platelet collect tube recess 255 are disposed yet further radially outwardly from the platelet support recess 249 to provide this function. As such, the platelet collect tube 424 may extend radially outwardly from the outer sidewall 376 of the blood processing vessel 352, extend upwardly through the lower platelet collect tube recess 255 and the upper platelet collect tube recess 254 behind or radially outwardly from the support 428, and extend above the channel housing 204.

Platelet-poor plasma continues to flow in a clockwise direction through the channel 208 after the platelet collect well 236 and may be removed from the channel 208. In this regard, the channel 208 further includes a generally concave plasma outlet slot 256 which is disposed proximate the second end 288 of the channel 208 and intersects the channel 208 at its inner channel wall 212 in substantially perpendicular fashion (e.g., the plasma outlet slot 256 interfaces with the inner channel wall 212). A plasma outlet port assembly 452 to the interior of the blood processing vessel 352 is disposed in this plasma outlet slot 256 such that plasma may be continually removed from the blood processing vessel 352 during an apheresis procedure (e.g., during continued rotation of the channel housing 204). This plasma may be collected and/or returned to the donor/patient 4. In order to increase the number of platelets that are separated and removed from the vessel 352 in a given apheresis procedure, the configuration of the channel 208 between the platelet collect well 236 and the plasma outlet slot 256 may be such that platelets which separate from plasma in this portion of the channel 208 actually flow in a counterclockwise direction back towards the platelet collect well 236 for removal from the channel 208. This may be provided by configuring the outer channel wall 216 such that it extends generally curvilinearly about the rotational axis 324 from the platelet collect well 236 to the plasma outlet slot 256 progressing generally inwardly toward the rotational axis 324 of the channel housing 204. Consequently, the portion of the channel 208 including the platelet collect well 236 and extending from the platelet collect well 236 to the second end 288 may be referred to as a second stage 316 of the channel 208.

The channel 208 is also configured to provide platelet-poor plasma to the control port slot 264 and thus to the control port assembly 488 in order to assist in automatically controlling the interface between the RBCs and the buffy coat in relation to the RBC dam 232. In this regard, the first end 284 of the channel 208 is interconnected with the second end 288 of the channel 208 by a connector slot 260. With the first connector 360 and second connector 368 of the blood processing vessel 352 being joined, they may be collectively disposed in this connector slot 260. As such, a continuous flowpath is provided within the blood processing vessel 352 and, for purposes of the automatic interface control feature, RBCs may flow to the control port slot 264 in a counterclockwise direction and plasma may flow to the control port slot 264 in a clockwise direction. The portion of the channel 208 extending from the first end 284 to the control port slot 264 may be referred to as a third stage 320 of the channel 208.

As noted above, the configuration of the channel 208 is desirable/important in a number of respects. As such, the dimensions of one embodiment of the channel 208 are provided herein and which may contribute to the functions of the channel 208 discussed below. The dimensions for one embodiment of the channel 208 are identified on FIG. 9B. All radius and thicknesses, etc., are expressed in inches.

One of the desired attributes of the channel 208 is that it facilitates the loading the of blood processing vessel 352 therein. This is provided by configuring the channel 208 to include a chamfer 210 on both sides of the channel 208 along the entire extent thereof. Generally, the chamfer 210 extends downwardly and inwardly toward a central portion of the channel 208 as illustrated, for instance, in FIGS. 12–13. In embodiment, the angle of this chamfer 210 ranges from about 30° to about 60° relative to horizontal, and preferably is about 45°. Moreover, the configuration of the channel 208 retains the blood processing vessel 352 within the channel 208 throughout the apheresis procedure. This is particularly relevant in that the channel housing 254 is preferably rotated a relatively high rotational velocities, such as about 3,000 RPM.

Another desirable attribute of the channel 208 is that it provides a self-retaining function for the blood processing vessel 352. The configuration of the channel 208 in at least the first stage 312, and preferably in the region of the platelet collect well 236 and in the region of the RBC dam 232 as well, is configured such that the upper portion of the channel 208 includes a restriction (e.g., such that the upper part of the channel 208 in this region has a reduced width in relation to a lower portion thereof). Although this configuration could also be utilized in the portion of the second stage 316 disposed between the platelet collect well 236 and the plasma outlet slot 256, in the illustrated embodiment the width or sedimentation distance of the channel 208 in this region is less than the width or sedimentation distance of the channel 208 throughout the entire first stage 312. This use of a "reduced width" can itself sufficiently retain the blood processing vessel 352 in the channel 208 in the "reduced-width" portion of the second stage 316 such that the inner channel wall 212 and outer channel wall 216 in this portion of the second stage 316 may be generally planar and vertically extending surfaces.

Figure 12:
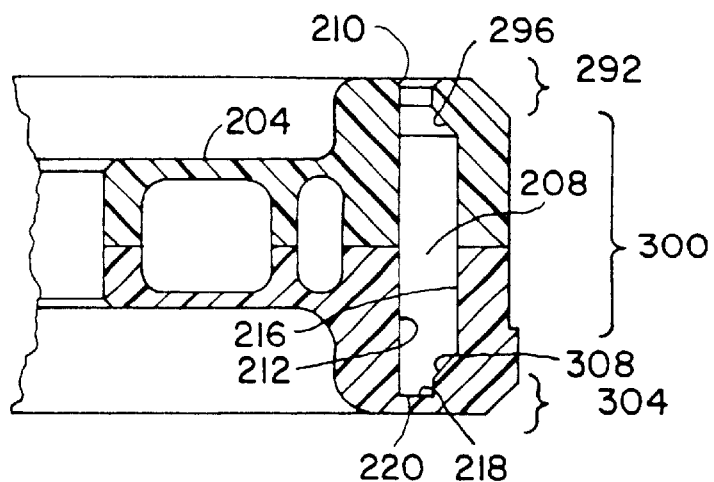
FIG. 12 is a cross-sectional view of the channel housing taken along line 12—12 in FIG. 9.
Figure 13:
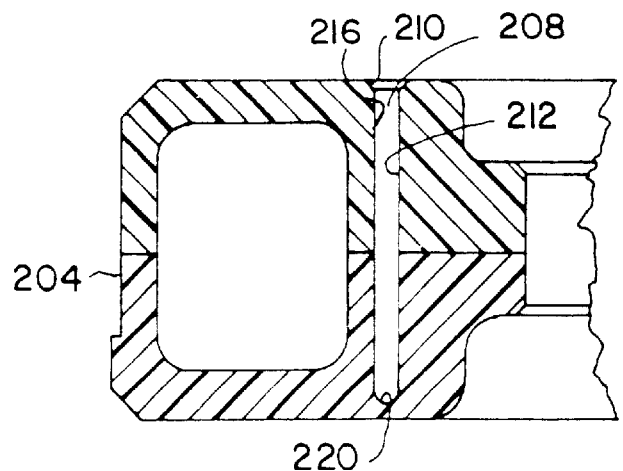
FIG. 13 is a cross-sectional view of the channel housing taken along line 13—13 in FIG. 9.
Figure 14C:
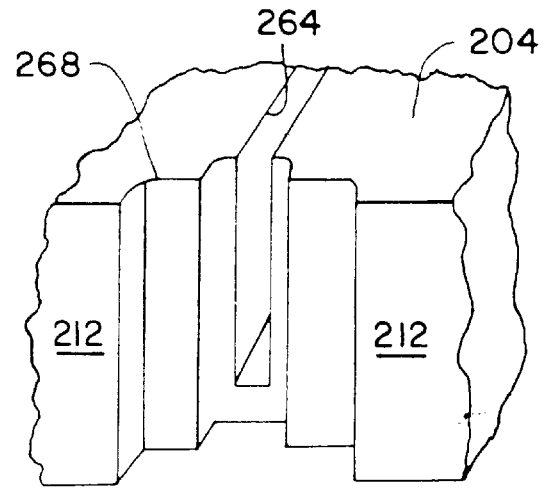
FIG. 14C is a cutaway, perspective view of the control port slot region of the channel housing of FIG. 8.
Figure 14A:
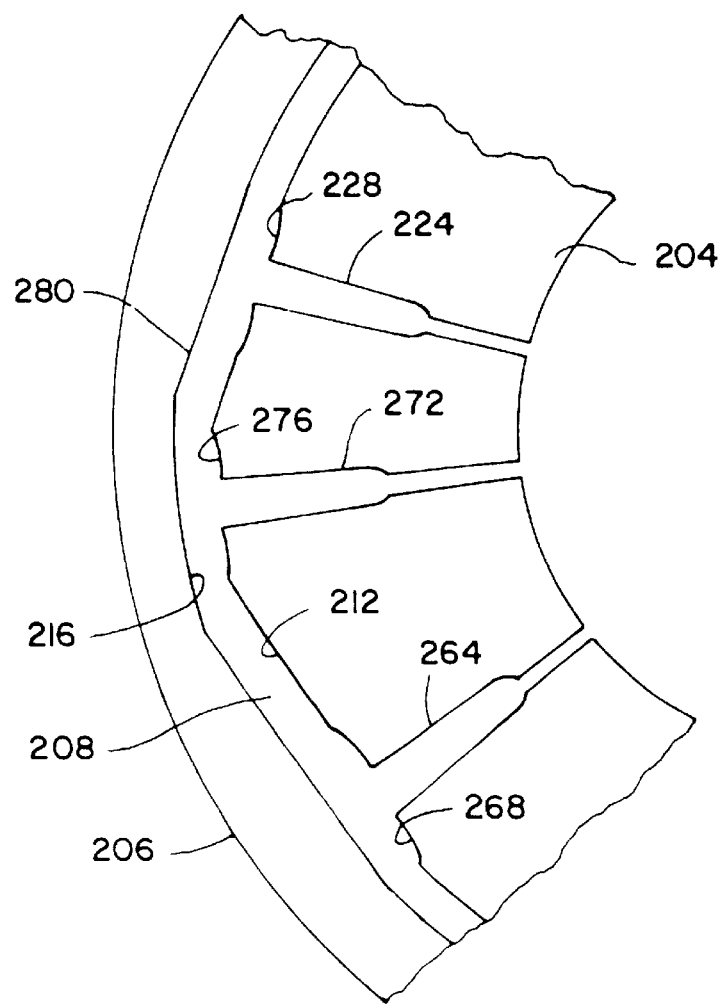
FIG. 14A is a top view of the blood inlet port slot, the RBC outlet slot, and the control port slot on the channel housing of FIG. 8.
Figure 14B:
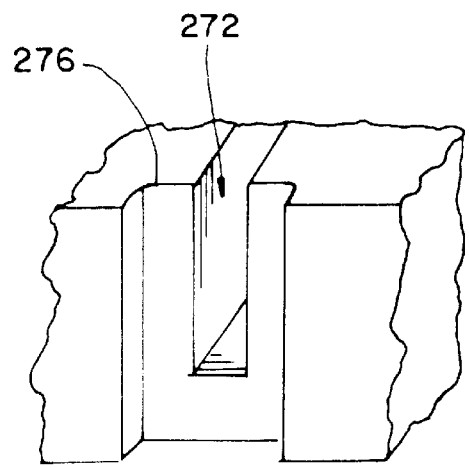
FIG. 14B is a cutaway, perspective view of the whole blood inlet port slot region of the channel housing of FIG. 8.

In the illustrated embodiment and as best illustrated in FIG. 12, the noted "restriction" in the channel 208 is provided by configuring the outer channel wall 216 with a generally C-shaped profile. In this portion of the channel 208, the channel 208 includes an upper channel section 292 having a first width, a mid-channel section 300 having a second width greater than the first width, and a lower channel section 304 having a width less than that of the mid-channel section 300 and which is typically equal to that of the upper channel section 292. This profile is provided by an upper lip 296 which extends radially inwardly from the outer channel wall 216 toward, but displaced from, the inner channel wall 212, and by a lower lip 308 which extends radially inwardly from the outer channel wall 216 toward, but displaced from, the inner channel wall 212. This lower lip 308 actually defines a portion of the channel base 220 but does extend entirely from the outer channel wall 216 to the inner channel wall 212 such that it defines a notch 218.

When the blood processing vessel 352 is loaded into the channel 208, the fluid-containing volume of the coinciding portion of the blood processing vessel 352 is disposed below the upper channel section 292 and is principally contained within the mid-channel section 300. That is, the upper lip 296 "hangs over" the fluid-containing volume of the blood processing vessel 352 over at least a portion of its length. The upper lip 296 thereby functions to retain the blood processing vessel 352 within the channel 208 during rotation of the channel housing 204. Moreover, the upper lip 296 reduces the potential for creep by supporting the vessel 352 proximate the upper seal 380. The upper channel section 292 and the lower channel section 304 are multi-functional in that they also serve to receive and support an upper seal 380 and lower seal 384 of the blood processing vessel 352 to a degree such that the stresses induced on these portions of the blood processing vessel 352 during an apheresis procedure are reduced as will be discussed in more detail below. As can be appreciated, a similarly configured upper lip and lower lip could extend outwardly from the inner channel wall 212 toward, but displaced from, the outer channel wall 216, alone or in combination with the upper lip 296 and lower lip 308, and still retain this same general profile for the channel 208 to provide the noted functions.

Another desirable attribute of the channel 208 is that it allows for the use of blood as the liquid which primes the blood processing vessel 352 versus, for instance, saline solutions. Priming with blood allows for the actual collection of blood components to begin immediately (i.e., blood used in the prime is separated into blood component types, at least one of which may be collected). Blood priming is subject to a number of characterizations in relation to the apheresis system 2 and is based upon the configuration of the channel 208. For instance, the configuration of the channel 208 allows for blood to be the first liquid introduced into the blood processing vessel 352 which is loaded in the channel 208. Moreover, the configuration of the channel 208 allows separated plasma to flow in a clockwise direction through the channel 208 and to reach the control port slot 264 (and thus the control port assembly 488 of the blood processing vessel 352) before any separated RBCs or any of the other noted large cells flow in the same clockwise direction beyond the RBC dam 232 and thus into the second stage 316 (i.e., a spillover condition). That is, blood priming may be utilized since control of the interface between the separated RBCs and the buffy coat is established before any RBCs or WBCs spill over into the second stage 316. Blood priming may also be characterized as providing blood and/or blood components to the entire volume of the blood processing vessel 352 prior to any RBCs or any of the other noted large cells flowing beyond the RBC dam 232 and into the second stage 316.

In order to achieve this desired objective of priming the blood processing vessel 352 with blood, generally the volume of the channel 208 which does not have RBCs to the volume of the channel 208 which does have RBCs must be less than one-half of one less than the ratio of the hematocrit of the RBCs leaving the channel 208 through the RBC outlet port assembly 516 to the hematocrit of the blood being introduced into the channel 208 through the blood inlet port assembly 388. This may be mathematically expressed as follows:

$$V_2/V_1 < (H_{RP}H_{IN}-1)/2,$$

where:

$V_2$=the volume of the channel 208 containing only plasma or platelet-rich plasma;

$V_1$=the volume of the channel 208 containing RBCs of the first stage 312 and third stage 320;

$H_{RP}$=the hematocrit of the packed RBCs leaving the channel 208 through the RBC outlet port assembly 516; and $H_{IN}$=the hematocrit of the blood entering the channel 208 through the blood inlet port assembly 388.

This equation assumes that the hematocrit in the RBC volume and is calculated as $(H_{in}+H_{RP})/2$. In the case where the $H_{IN}$ is equal to 0.47 and $H_{RP}$ is equal to 0.75, this requires that the ratio of $V_1/V_2$ be less than 0.30 in order for a blood prime to be possible.

The noted ratio may be further characterized as the ratio of that portion of the channel 208 which may be characterized as containing primarily plasma (e.g., $V_{PL}$) to the volume of that portion of the channel 208 which may be characterized as containing primarily RBCs (e.g., $V_{RBC}$). Referring to FIG. 15, these respective volumes may be defined by a reference circle 332 which originates at the rotational axis 324 and which intersects the RBC dam 232 at the illustrated location which would be at the border of a spillover condition. Portions of the channel 208 which are disposed outside of this reference circle 232 are defined as that portion of the channel 208 which includes primarily RBCs or which defines VBC (e.g., about 77.85 cc in the illustrated embodiment), while those portions of the channel 208 which are disposed inside of the reference circle 232 are defined as that portion of the channel 208 which includes primarily plasma or which defines $V_{PL}$ (e.g., about 19.6 cc in the illustrated embodiment). In the illustrated embodiment, the ratio of $V_{PL}/V_{RBC}$ is about 0.25 which is less than that noted above for the theoretical calculation for the blood prime (i.e., 0.30 based upon comparison of the hematocrits). In order to further achieve the noted desired ratio, the width and height of the channel 208 throughout that portion of the second stage 316 disposed in a clockwise direction from the platelet collect well 236, also in third stage 320, are each less than the width and height of the channel 208 throughout the entire first stage 312.

Another important feature relating to the configuration of the channel 208 is that the radially inwardmost portion of the inner channel wall 212 is at the interface with the plasma outlet slot 256. That is, the entirety of the inner channel wall 212 slopes toward the plasma outlet slot 256. This allows any air which is present in the blood processing vessel 352 during priming to be removed from the blood processing vessel 352 through the plasma outlet slot 256 and more specifically the plasma outlet port assembly 452 since the air will be the least dense fluid within the blood processing vessel 352 at this time.

Another desirable attribute of the channel 208 is that it contributes to being able to utilize a high packing factor in an apheresis procedure. A "packing factor" is a dimensionless quantification of the degree of packing of the various blood component types in the first stage 312 and is thus reflective of the spacings between the various blood component types. The packing factor may thus be viewed similarly to a theoretical density of sorts (e.g., given a quantity of space, what is the maximum number of a particular blood component type that can be contained in this space).

The packing factor is more specifically defined by the following equation:

$$PF = \omega^2 \times R \times (v_{RBC}/W) \times V/Q_{IN},$$

where:

PF=packing factor;

$\omega$=rotational velocity;

R=the average radius of the outer channel wall 216 in the first cell separation stage 312;

$v_{RBC}$=the sedimentation velocity of RBCs at 1G;

V=the functional volume of the first cell separation stage 312;

W=the average sedimentation distance or width of the channel 208; and $Q_{IN}$=the total inlet flow to the channel 208.

Consequently, the packing factor as used herein is dependent upon not only the configuration of the channel 208, particularly the first stage 312, but the rotational velocities being used in the apheresis procedure as well as the inlet flow to the blood processing vessel 352. The following are packing factors associated with the blood processing channel 208 having the above-described dimensions:

| N (rpm) | $Q_{in}$ ml/mi | V (ml) | PF | G @ $R_{avg}$ | P @ R1st (psi) |
|---|---|---|---|---|---|
| 0 | 0 | 62.8 | 0.0 | 0.0 | 0.0 |
| 905 | 5 | 62.8 | 13.0 | 100.1 | 8.1 |
| 1279 | 10 | 62.8 | 13.0 | 200.2 | 16.2 |
| 1567 | 15 | 62.8 | 13.0 | 300.2 | 24.3 |
| 1809 | 20 | 62.8 | 13.0 | 400.3 | 32.5 |
| 2023 | 25 | 62.8 | 13.0 | 500.4 | 40.6 |
| 2216 | 30 | 62.8 | 13.0 | 600.5 | 48.7 |

-continued

| | N (rpm) | $Q_{in}$ ml/mi | V (ml) | PF | G @ $R_{avg}$ | P @ R1st (psi) |
|---|---|---|---|---|---|---|
| FF8 | 2394 | 35 | 62.8 | 13.0 | 700.6 | 56.8 |
| SLOPE = .02 | 2559 | 40 | 62.8 | 13.0 | 800.6 | 64.9 |
| | 2714 | 45 | 62.8 | 13.0 | 900.7 | 73.0 |
| | 2861 | 50 | 62.8 | 13.0 | 1100.9 | 81.1 |
| | 3001 | 55 | 62.8 | 13.0 | 1100.9 | 89.3 |
| | 3001 | 60 | 62.8 | 11.9 | 1100.9 | 89.3 |
| | 3001 | 65 | 62.8 | 11.0 | 1100.9 | 89.3 |
| | 3001 | 70 | 62.8 | 10.2 | 1100.9 | 89.3 |
| | 3001 | 75 | 62.8 | 9.5 | 1100.9 | 89.3 |
| | 3001 | 80 | 62.8 | 8.9 | 1100.9 | 89.3 |
| | 3001 | 85 | 62.8 | 8.4 | 1100.9 | 89.3 |
| | 3001 | 90 | 62.8 | 7.9 | 1100.9 | 89.3 |
| | 3001 | 95 | 62.8 | 7.5 | 1100.9 | 89.3 |
| | 3001 | 100 | 62.8 | 7.1 | 1100.9 | 89.3 |
| | 3001 | 105 | 62.8 | 6.8 | 1100.9 | 89.3 |
| | 3001 | 110 | 62.8 | 6.5 | 1100.9 | 89.3 |
| | 3001 | 115 | 62.8 | 6.2 | 1100.9 | 89.3 |
| | 3001 | 120 | 62.8 | 6.0 | 1100.9 | 89.3 |
| | 3001 | 125 | 62.8 | 5.7 | 1100.9 | 89.3 |
| | 3001 | 130 | 62.8 | 5.5 | 1100.9 | 89.3 |
| | 3001 | 135 | 62.8 | 5.3 | 1100.9 | 89.3 |
| | 3001 | 140 | 62.8 | 5.1 | 1100.9 | 89.3 |

Note the G forces are listed for the various rotational speeds at the middle of the first stage 312 and for a 10 inch outer diameter for the channel housing 204. At about 2,560 RPM, the G force is about 800 G, while at about 3,000 RPM the G force is about 1,100 Gs.

Increasing the packing factor beyond a certain point produces diminishing returns regarding the collection of blood component types. That is, further increases in packing factor may not produce correspondingly increased collection efficiencies and may in fact impede the collection of blood component types. It is believed that a packing factor ranging from about 11 to about 15, and more preferably about 13, is optimum for collection of blood component types. As such, the rotational velocity of the channel housing 204 may be adjusted based upon the inlet flows being provided to the blood processing vessel 352 to maintain the packing factor. For instance, the desired operating speed for the centrifuge housing 204 during the normal course of an apheresis procedure is about 3,000 RPM. However, this rotational speed may be reduced to "match" the inlet flow to the blood processing vessel 352 in order to retain the desired packing factor. Similarly, the rotational speed of the channel housing 204 may be increased to "match" an increased inlet flow to the blood processing vessel 352 in order to retain the desired packing factor.

Due to constraints regarding the blood processing vessel 352, more specifically the various tubes interconnected therewith (e.g., which provide the seal-less loop), the above-noted desired packing factor of about 13 may be realized for inlet flows of up to about 55 ml/min. (instantaneous). Beyond 55 ml/min., the rotational speed would have to be increased above 3000 RMP to maintain the desired packing factor of about 13. Although tubes exist which will withstand those rotational speeds, presently they are not approved for use in an apheresis system. With the presently approved tubing, the packing factor may be maintained at a minimum of about 10, and preferably at least about 10.2, for inlet flows (instantaneous) of about 40–70 ml/min.

At the above noted increased rotational speeds, the channel 208 not only provides for achieving an increased packing factor, but reduces the impact of this high packing factor on the collection efficiency regarding platelet collection. Specifically, the configuration of the channel 208 is selected to reduce the number of platelets that are retained within the first stage 312. The configuration of the channel 208 in the first stage 208 utilizes a progressively reduced width or sedimentation distance progressing from the blood inlet slot 224 to the RBC dam 232. That is, the width of the channel 208 proximate the blood inlet slot 224 is less than the width of the channel 208 proximate the RBC dam 232. This configuration of the channel 208 in the first stage 312 reduces the volume of the "buffy coat" or more specifically layer between the RBCs and platelets to be collected. As noted, this buffy coat includes primarily WBCs and lymphocytes, as well as the radially outwardmost portion of the platelet layer. The "buffy coat" is preferably retained in the first stage 312 during an apheresis procedure. Since the volume of the "buffy coat" is reduced by the reduced width of the channel 208 proximate the RBC dam 232, this reduces the number of platelets which are retained in the first stage 312, and thus increases the number of platelets which flow to the platelet collect well 236.

Disposable Set: Blood Processing Vessel

The blood processing vessel 352 is disposed within the channel 208 for directly interfacing with and receiving a flow of blood in an apheresis procedure. The use of the blood processing vessel 352 alleviates the need for sterilization of the channel housing 204 after each apheresis procedure and the vessel 352 may be discarded to provide a disposable system. There are initially two important characteristics regarding the overall structure of the blood processing vessel 352. The blood processing vessel 352 is constructed such that it is sufficiently rigid to be free standing in the channel 208. Moreover, the blood processing vessel 352 is also sufficiently rigid so as to loaded in the channel 208 having the above-identified configuration (i.e., such that the blood processing vessel 352 must be directed through the reduced width upper channel section 292 before passage into the larger width mid-channel section 300). However, the blood processing vessel 352 must also be sufficiently flexible so as to substantially conform to the shape of the channel 208 during an apheresis procedure.

In order to achieve the above-noted characteristics, the blood processing vessel 352 may be constructed as follows. Initially, materials for the blood processing vessel 352 include PVC, PETG, and polyolefins, with PVC being preferred. Moreover, the wall of thickness of the blood processing vessel 352 will typically range between about 0.030" and 0.040". Furthermore, the durometer rating of the body of the blood processing vessel 352 will generally range from about 50 Shore A to about 90 Shore A.

Referring primarily to FIGS. 16–23B, the blood processing vessel 352 includes a first end 356 and a second end 364 which overlaps with the first end 356 and is radially spaced therefrom. A first connector 360 is disposed proximate the first end 356 and a second connector 368 is disposed proximate the second end 364. When the first connector 360 and second connector 368 are engaged (typically permanently), a continuous flow path is available through the blood processing vessel 352. This construction of the blood processing vessel 352 facilitates loading in the channel 208 in the proper position and as noted also contributes to the automatic control of the interface between the separated RBCs and the buffy coat relative to the RBC dam 232.

The blood processing vessel 352 includes an inner sidewall 372 and an outer sidewall 376. In the illustrated embodiment, the blood processing vessel 352 is formed by sealing two pieces of material together (e.g., RF welding).

More specifically, the inner sidewall 372 and outer sidewall 376 are connected along the entire length of the blood processing vessel 352 to define an upper seal 380 and a lower seal 384. Seals are also provided on the ends of the vessel 352. The upper seal 380 is disposed in the reduced width upper channel section 292 of the channel 208, while the lower seal 384 is disposed in the reduced width lower channel section 304 of the channel 208 (e.g., FIG. 19F). This again reduces the stresses on the upper seal 380 and lower seal 384 when a flow of blood is provided to the blood processing vessel 352 and pressurizes the same. That is, the upper seal 380 and lower seal 384 are effectively supported by the channel 208 during an apheresis procedure such that a resistance is provided to a "pulling apart" of the upper seal 380 and lower seal 384. By utilizing two separate sheets to form the blood processing vessel 352, a "flatter" profile may also be achieved. This type of profile is beneficial during rinseback, and also facilitates loading and unloading of the vessel 352 relative to the channel 208.

Blood is introduced into the interior of the blood processing vessel 352 through a blood inlet port assembly 388 which is more particularly illustrated in FIGS. 19A–G. Initially, the port 392, as all other ports, is welded to the blood processing vessel 352 over a relatively small area. This results in less movement of materials due to the welding procedure which provides a smoother surface for engagement by the blood and/or blood component types.

The blood inlet port assembly 388 includes a blood inlet port 392 and a blood inlet tube 412 which is fluidly interconnected therewith exteriorly of the blood processing vessel 352. The blood inlet port 392 extends through and beyond the inner sidewall 372 of the blood processing vessel 352 into an interior portion of the blood processing vessel 352. Generally, the blood inlet port assembly 388 is structured to allow blood to be introduced into the blood processing vessel 352 during an apheresis procedure without substantially adversely affecting the operation of the apheresis system 2.

Figure 19A:
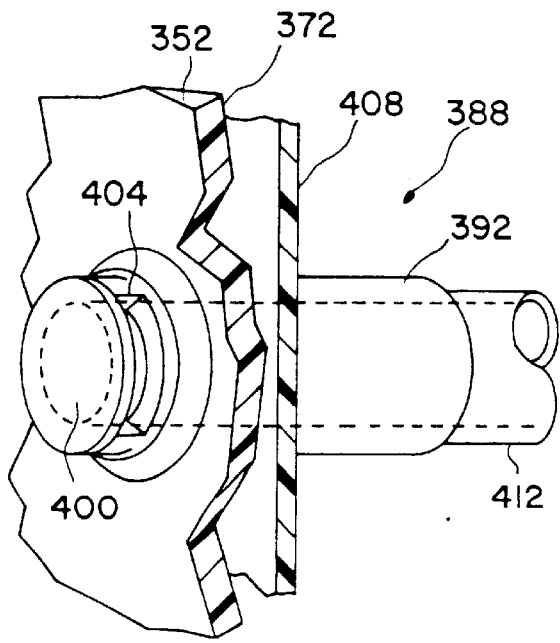
FIG. 19A is a cutaway, perspective view of the blood inlet port assembly for the blood processing vessel of FIG. 8.
Figure 19B:
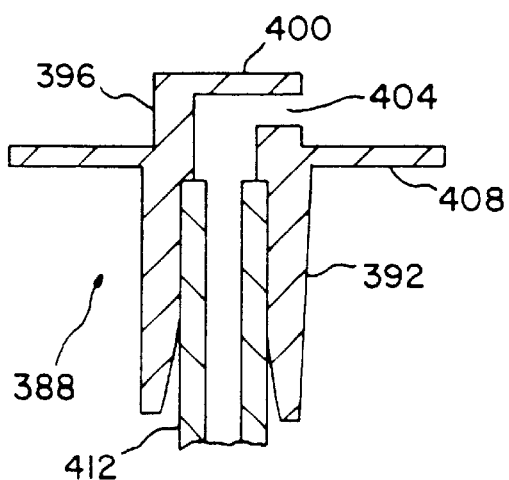
FIG. 19B is a longitudinal cross-sectional view of the blood inlet port assembly for the blood processing vessel of FIG. 8.
Figure 19C:
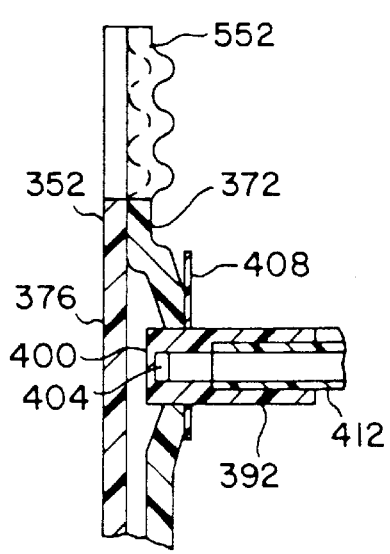
FIG. 19C is a cross-sectional view of the blood inlet port assembly interfacing with the blood processing vessel of FIG. 8.
Figure 19D:
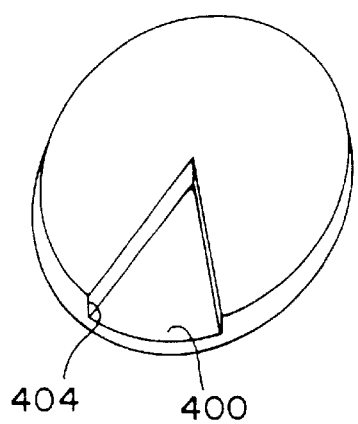
FIG. 19D is a perspective view of the interior of the vane of the blood inlet port of FIG. 19C.

The blood inlet port 392 includes a substantially cylindrical sidewall 396. A generally vertically extending slot 404 is disposed proximate an end of the sidewall 396 of the blood inlet port 392 such that the slot 404 is substantially parallel with the inner sidewall 372 and outer sidewall 376 of the blood processing vessel 352. The slot 404 projects in the clockwise direction, and thus directs the flow of blood in the channel 208 generally toward the RBC dam 232. A vane 400 is positioned on the end of the cylindrical sidewall 396, is disposed to be substantially parallel with the inner sidewall 372, and thereby directs the flow of blood out through the slot 404. As illustrated in FIG. 19D, the vane 400 includes a generally V-shaped notch on the interior of the blood inlet port 392, the arcuate extent of which defines the "height" of the slot 404.

The desired manner of flow of blood into the blood processing vessel 352 during an apheresis procedure is subject to a number of characterizations, each of which is provided by the above-described blood inlet port assembly 388. Initially, the flow of blood into the blood processing vessel may be characterized as being at an angle of less than 900 relative a reference line which is perpendicular to the inner sidewall 372 of the blood processing vessel 352. That is, the blood is injected in a direction which is at least partially in the direction of the desired flow of blood through the blood processing vessel 352. Moreover, the desired flow of blood into the blood processing vessel 352 may be characterized as that which reduces the effect on other flow characteristics within blood processing vessel 352 at the blood inlet port 392.

Figure 19E:
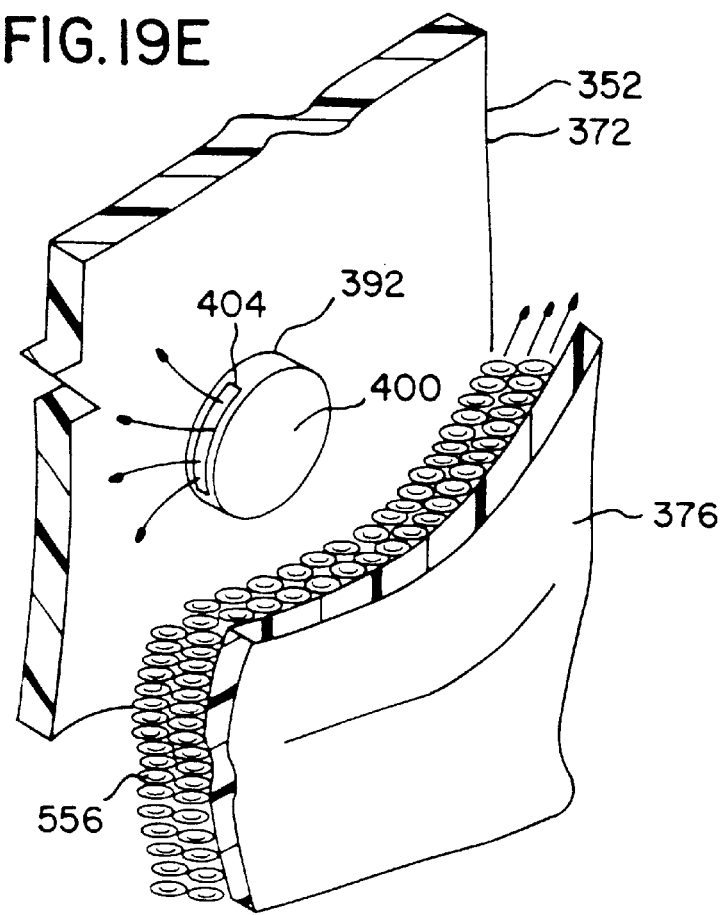
FIG. 19E is a cutaway, perspective view of blood being introduced into the blood processing vessel of FIG. 8 during an apheresis procedure.
Figure 19F:
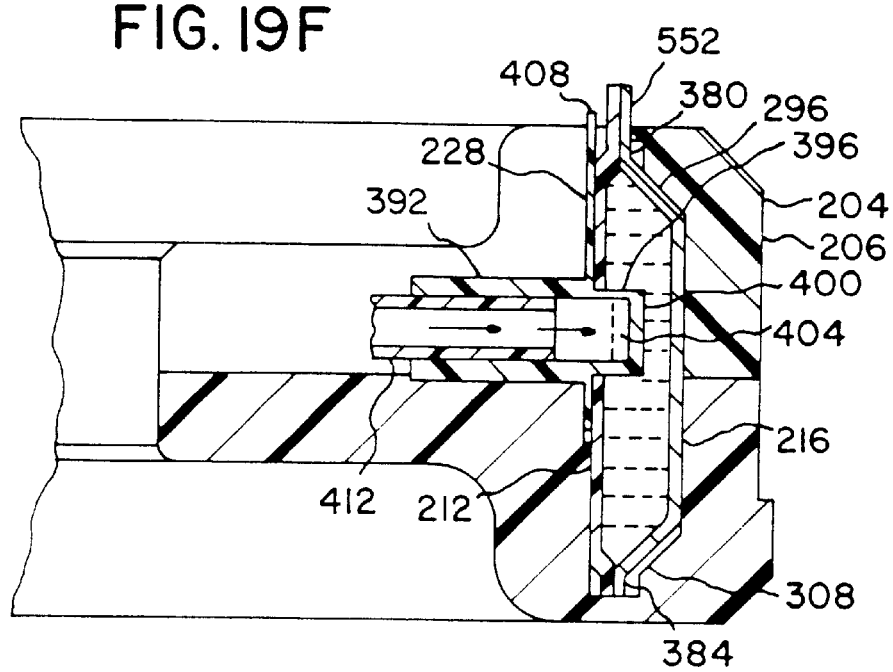
FIG. 19F is a cross-sectional view of blood being introduced into the blood processing vessel and channel of FIG. 8 during an apheresis procedure.
Figure 20A:
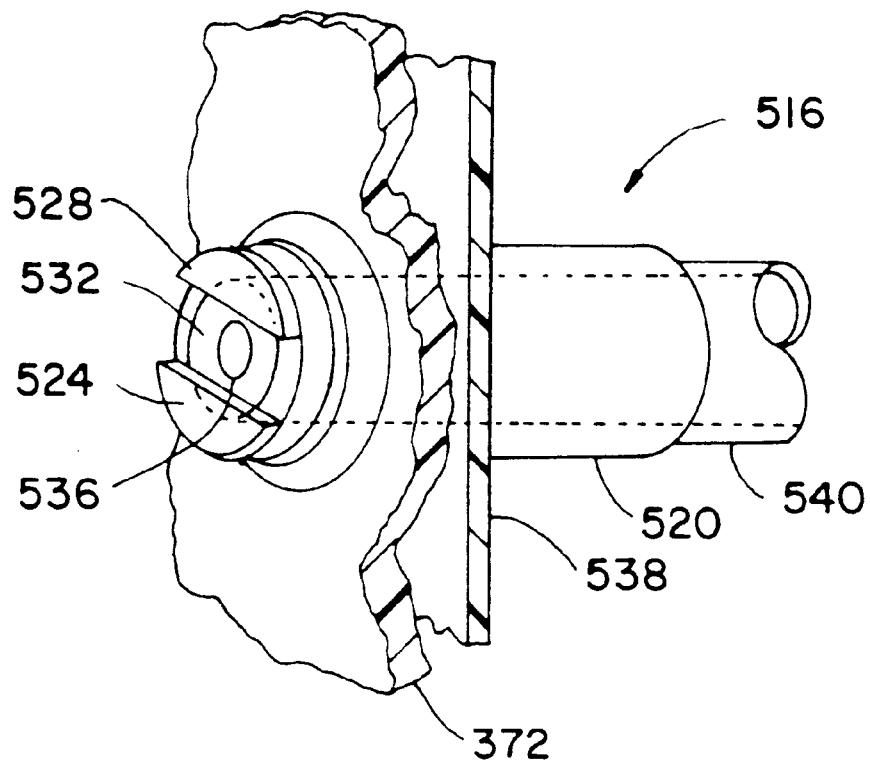
FIG. 20A is a cutaway, perspective view of the red blood cell outlet port assembly interfacing with the blood processing vessel of FIG. 8.
Figure 20B:
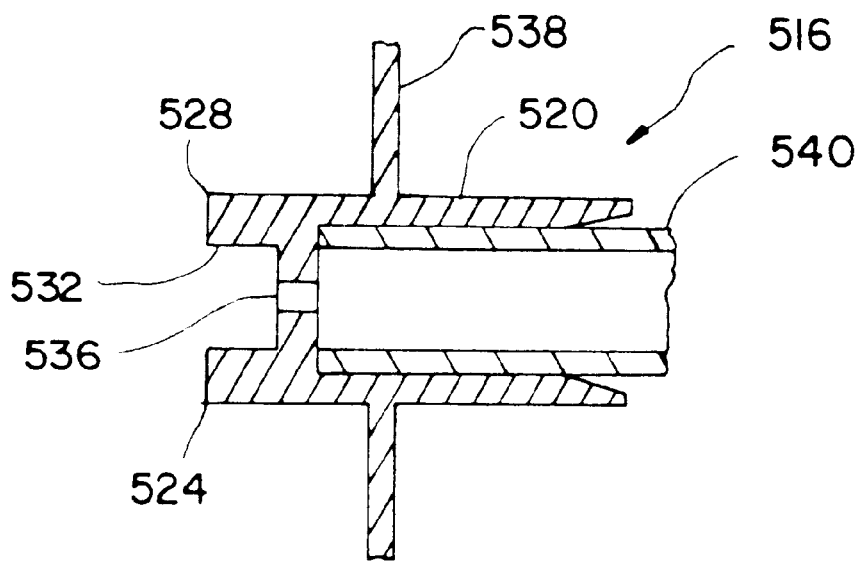
FIG. 20B is a longitudinal, cross-sectional view of the red blood cell outlet port assembly of FIG. 20A.
Figure 20C:
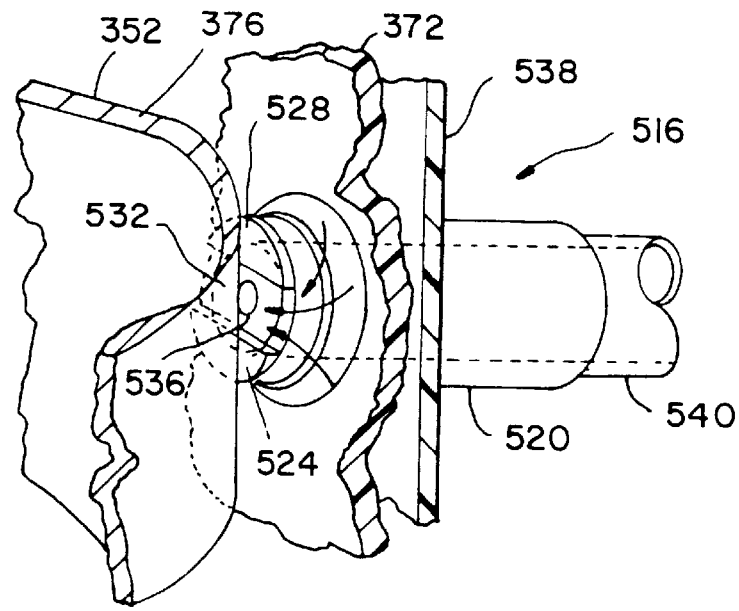
FIG. 20C is a cutaway, perspective view of the red blood cell port assembly interfacing with the blood processing vessel of FIG. 8 during rinseback at the end of an apheresis procedure.
Figure 20D:
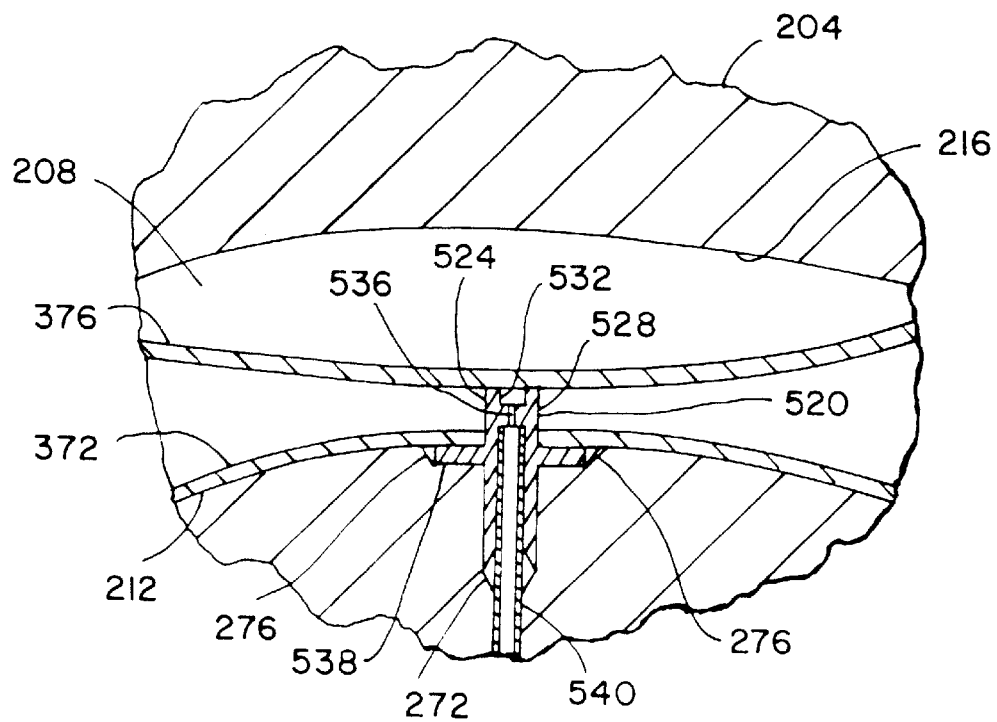
FIG. 20D is a cross-sectional view, looking downwardly, of the red blood cell outlet port assembly interfacing with the blood processing vessel in the channel of FIG. 8 during rinseback at the end of an apheresis procedure.
Figure 21A:
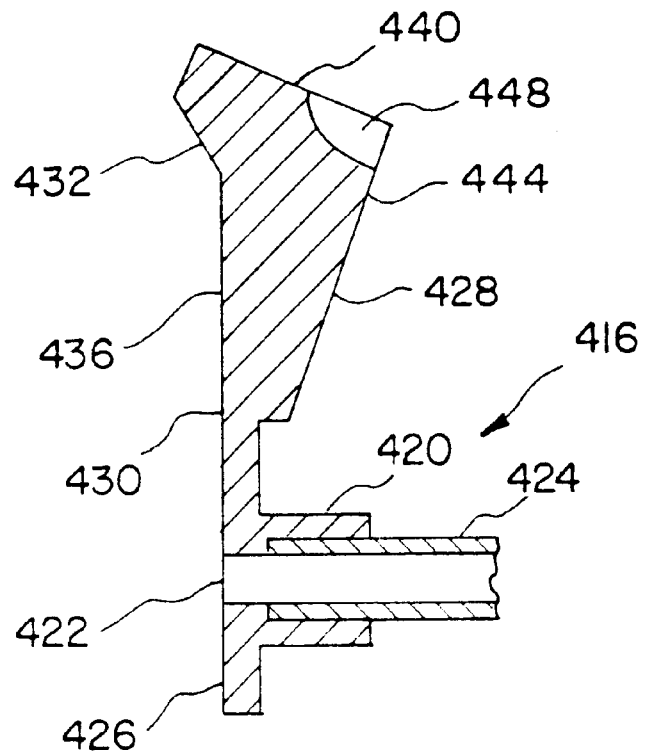
FIG. 21A is a cross-sectional view of the platelet outlet port assembly for the blood processing vessel of FIG. 8.
Figure 21B:
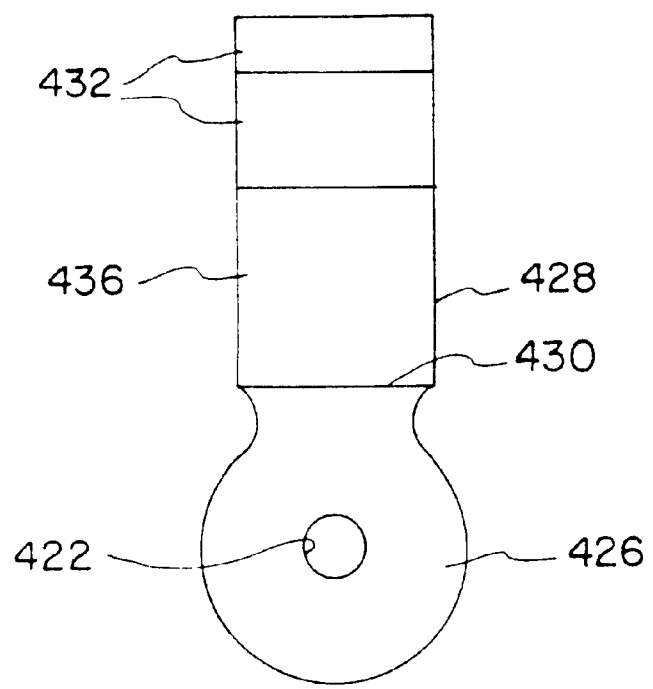
FIG. 21B is a plan view of the platelet outlet port assembly of FIG. 21A from the interior of the channel.

Separated RBCs 556 again flow along the outer sidewall 376 of the blood processing vessel 352 adjacent the outer channel wall 216, past the blood inlet port 392, and to the RBC outlet port assembly 516 as illustrated in FIGS. 19E and 19G. The desired flow of blood into the blood processing vessel 352 may then be further characterized as that which is substantially parallel with at least one other flow in the region of the blood inlet port 392 (e.g., inject the blood substantially parallel with the flow of RBCs 556). This manner of introducing blood into the blood processing vessel 352 may then be further characterized as that which does not significantly impact at least one other flow in the region of the blood inlet port 392.

As noted above, the blood inlet port assembly 388 interfaces with the inner sidewall 372 of the blood processing vessel 352 in a manner which minimizes the discontinuity along the inner channel wall 212 in the region of the blood inlet slot 224 in which the blood inlet port 392 is disposed. Specifically, a shield 408 may be integrally formed with and disposed about the blood inlet port 392. The shield 408 is disposed on an exterior surface of the blood processing vessel 352 and interfaces with its inner sidewall 372. The shield 408 is at least in partial overlapping relation with the inner sidewall 372. Moreover, in the case where the shield 408 is integrally formed with the port 392, it need not be attached to the inner sidewall 372. The port 392 is installed asymmetrical relative to the shield 408 which is beneficial for manufacturability. All shields and their blood-related ports discussed below also include this feature.

Generally, the shield 408 is more rigid than the inner sidewall 372 of the blood processing vessel 352. This increased rigidity may be provided by utilizing a more rigid material for the shield 408 than is used for the inner sidewall 372. For instance, the durometer rating of the material forming the shield 408 may range from about 90 Shore A to about 130 Shore A, while the durometer rating of the material forming the inner sidewall 372 of the blood processing vessel 352 again ranges from about 50 Shore A to about 90 Shore A in one embodiment. This durometer rating (when the shield 408 and port 392 are integrally formed) also enhances the seal between the port 392 and the tube installed therein.

When the blood inlet port 392 is disposed in the blood inlet slot 224 when loading the blood processing vessel 352 in the channel 208, the shield 408 is positioned within the recess 228 formed in the inner channel wall 212. Again, the blood inlet slot 224 intersects with the inner channel wall 212, and more specifically the recess 228. That is, the recess 228 contains and is disposed about one end of the blood inlet slot 224. Preferably, the thickness of the shield 408 is substantially equal to the depth or thickness of the recess 228 such that the amount of discontinuity along the inner channel wall 212 in the region of the blood inlet slot 224 is reduced or minimized. Due to the increased rigidity of the shield 408 in comparison to the materials forming the blood processing vessel 352, when the blood processing vessel 352 is pressurized during an apheresis procedure the shield 408 restricts movement of the blood processing vessel 352 and/or the blood inlet port 392 into the blood inlet slot 224. That is, the shield 408 restricts and preferably minimizes any deflection of the blood processing vessel 352 into the blood inlet slot 224 during the procedure. Moreover, with the shield 408 being integrally formed with the blood inlet port 392, the radial position of the vertical slot 404 in the blood inlet port 392 is not dependent upon the thickness of the materials forming the blood processing vessel 352.

In the first stage 312, blood which is provided to the blood processing vessel 352 by the blood inlet port assembly 388 is separated into RBCs, WBCs, platelets, and plasma. The RBCs, as well as the WBCs, are retained within the first stage 312 and are preferably precluded from flowing in a clockwise direction past the RBC dam 232 into the platelet collect well 236. Instead, the RBCs and WBCs are induced to flow along the outer channel wall 216 in a counterclockwise direction past the blood inlet port 392 and toward the RBC outlet port assembly 516 of the blood processing vessel 352. That is, the RBC outlet port assembly 516 is disposed in a counterclockwise direction from the blood inlet port assembly 388. However, as noted above, the control port dam 280 impedes the flow buffy coat control port assembly 488 to provide a sharp interface between the separated RBCs and the plasma proximate the control port assembly 488 such that this may be used to control the radial position of the interface between the RBCs and the buffy coat in the area of the RBC dam 232.

The RBC outlet port assembly 516 is more specifically illustrated in FIGS. 20A–D and generally includes an RBC outlet port 520 and an RBC outlet tube 540 fluidly interconnected therewith exteriorly of the blood processing vessel 352. The RBC outlet port 520 extends through and beyond the inner sidewall 372 of the blood processing vessel 352 into an interior portion of the blood processing vessel 352. In addition to removing separated RBCs from the blood processing vessel 352 during an apheresis procedure, the RBC outlet port assembly 516 also functions in combination with the control port assembly 488 to automatically control the radial position of the interface between separated RBCs and the buffy coat relative to the RBC dam 232 (e.g., to prevent RBCs from flowing beyond the RBC dam 232) in a manner discussed in more detail below.

The RBC outlet port 520 is also configured to reduce the potential for the flow therethrough being obstructed during rinseback (i.e., during an attempted evacuation of the blood processing vessel 352 upon completion of blood component separation so as to provide as much of the contents thereof back to the donor/patient 4). During rinseback, the rotation of the channel housing 204 is terminated and a relatively significant drawing action (e.g., by pumping) is utilized to attempt to remove all contents from the blood processing vessel 352. The end of the RBC outlet port 520 includes a first protrusion 524 and a second protrusion 528 displaced therefrom, with a central recess 532 being disposed therebetween which contains the noted orifice 536 for the blood outlet port 520. The first protrusion 524 and the second protrusion 528 each extend further beyond the inner sidewall 372 of the blood processing vessel 352 a greater distance then the central recess 532. As such, during rinseback if the outer sidewall 376 attempts to contact the inner sidewall 372, the first protrusion 524 and second protrusion 528 will displace the central recess 532 and its orifice 536 away from the outer sidewall 376. This retains the orifice 536 in an open condition such that the flow therethrough is not obstructed during rinseback.

As noted above, the RBC outlet port assembly 516 interfaces with the inner sidewall 372 of the blood processing vessel 352 in a manner which minimizes the discontinuity along the inner channel wall 212 in the region of the RBC outlet 272 in which the RBC outlet port 520 is disposed. Specifically, a shield 538 is integrally formed with and disposed about the RBC outlet port 520. The shield 538 is disposed on an exterior surface of the blood processing vessel 352 and interfaces with its inner sidewall 372. The shield 538 is at least in partial over-lapping relation with the inner sidewall 372. Moreover, in the case where the shield 538 is integrally formed with the port 520, it need not be attached to the inner sidewall 372. Generally, the shield 538 is more rigid than the inner sidewall 372. This increased rigidity may be provided by utilizing a more rigid material for the shield 538 than is used for the inner sidewall 372. For instance, the durometer rating of the material forming the shield 538 may range from about 90 Shore A to about 130 Shore A, while the durometer rating of the material forming the inner sidewall 372 of the blood processing vessel 352 again ranges from about 50 Shore A to about 90 Shore A in one embodiment.

When the RBC outlet port 520 is disposed in the RBC outlet slot 272 when loading the blood processing vessel 352 in the channel 208, the shield 538 is positioned within the recess 276 formed in the inner channel wall 212. Again, the RBC outlet slot 272 intersects with the inner channel wall 212, and more specifically the recess 276. That is, the recess 276 contains and is disposed about one end of the RBC outlet slot 272. Preferably, the thickness of the shield 538 is substantially equal to the depth or thickness of the recess 276 such that the amount of discontinuity along the inner channel wall 212 in the region of the RBC outlet slot 272 is reduced or minimized. Due to the increased rigidity of the shield 538 in comparison to the materials forming the blood processing vessel 352, when the blood processing vessel 352 is pressurized during an apheresis procedure, the shield 538 restricts movement of the blood processing vessel 352 and/or the RBC outlet port 520 into the RBC outlet slot 272. That is, the shield 538 restricts and preferably minimizes any deflection of the blood processing vessel 352 into the RBC outlet slot 272. Moreover, with the shield 538 being integrally formed with the RBC outlet port 520, the radial position of the orifice 536 is not dependent upon the thickness of the materials forming the blood processing vessel 352.

Separated platelets are allowed to flow beyond the RBC dam 232 and into the second stage 316 of the channel 208 in platelet-rich plasma. The blood processing vessel 352 includes a platelet collect port assembly 416 to continually remove these platelets from the vessel 352 throughout an apheresis procedure and such is more particularly illustrated in FIGS. 8, 16, and 21A–B. Generally, the platelet collect port assembly 416 is disposed in a clockwise direction from the blood inlet port assembly 388, as well as from the RBC dam 232 when the blood processing vessel 352 is loaded into the channel 208. Moreover, the platelet collect port assembly 416 interfaces with the outer sidewall 376 of the blood processing vessel 352.

The platelet collect port assembly 416 is disposed in the platelet support recess 249 and the platelet outlet tube recess 254 which are disposed radially outwardly from the portion of the platelet collect well 236 defined by the outer channel wall 216 of the channel 208. The platelet collect port assembly 416 generally includes a platelet collect port 420 and a platelet collect tube 424 which is fluidly interconnected therewith exteriorly of the blood processing vessel 352. The orifice 422 of the port 420 may be substantially flush with the interior surface of the outer sidewall 376 of the blood processing vessel 352. Moreover, the radial position of the orifice 422 is established by engagement of part of the platelet collect port 420 with boundaries of the recess 249 and/or 254.

The platelet collect port 420 is welded to the blood processing vessel 352. The thickness of the overlapping portions of the port 420 and vessel 352 are substantially equal. The weld area is overheated such that there is a mixing of the two materials. This results in the platelet collect port 420 being able to flex substantially against the outer channel wall 216 when the vessel 352 is pressurized.

The blood processing vessel 352 and the outer channel wall 216 of the channel 210 collectively define the platelet collect well 236. The contribution of the blood processing vessel 352 to the platelet collect well 236 is provided by a substantially rigid support 428 which is disposed vertically above the platelet collect port 420 and hingedly interconnected at location 430 with the outer sidewall 376 and/or a mounting plate 426 of the platelet collect port 420. The contoured support 428 includes a first face 432 and a second face 436 which interface with the exterior surface of the outer sidewall 376 of the blood processing vessel 352 (i.e., the support overlaps with the sidewall 376 of the blood processing vessel 352 and need not be attached thereto over the entire interface therewith) and which are disposed in different angular positions. The upper portion of the first face 432 extends over the top of the blood processing vessel 352, while the lower portion of the first face 432 generally coincides with the upper seal 380 on the blood processing vessel 352. The second face 436 interfaces with the outer sidewall 376 in a region of the fluid-containing volume of the blood processing vessel 352 and is the primary surface which directs platelets toward the platelet collect port 420.

When the blood processing vessel 352 is pressurized, the support 428 moves into a predetermined position defined by portions of the platelet collect recess 252. Specifically, a third face 440 is retained under an upper lip 254 on the upper perimeter of the platelet support recess 249, and the two sides of a fourth face 444 seat against a shoulder 252 disposed on each side of the platelet support recess 249. A platelet tubing notch 448 is formed in the support 428 at generally the intersection between the third face 440 and the fourth face 444. The platelet collect tube 426 thus may extend out from the platelet collect port 420, up the platelet collect tube recess 254, against the platelet tube notch 448 if necessary, and above the channel housing 204 to pass down through the central opening 328 therein.

In order to increase the purity of platelets that are collected, a platelet purification system as described in U.S. patent application Ser. Nos. 08/423,578 and 08/423,583 may be disposed in the platelet collect tube 424, and the entire disclosures of these patent applications is incorporated by reference in their entirety herein.

Figure 22:
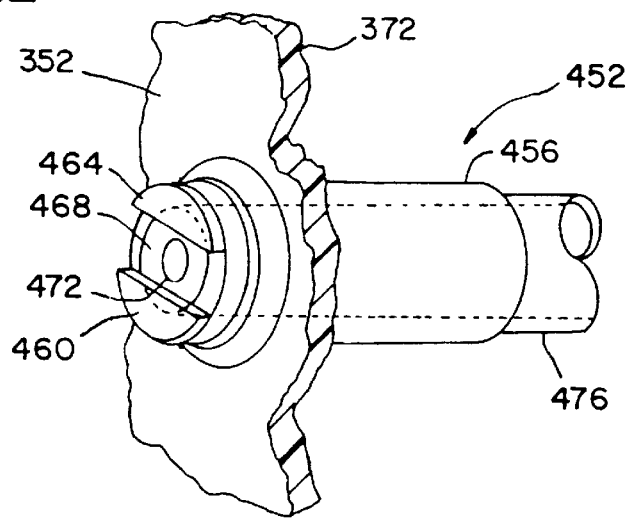
FIG. 22 is a cutaway, perspective view of the plasma port assembly for the blood processing vessel of FIG. 8.

Platelet-poor plasma flows beyond the platelet collect well 236 and to the plasma outlet port assembly 452. Here, some of the platelet-poor plasma may be removed from the blood processing vessel 352 and collected, although this "separated" plasma may also be returned the donor/patient 4 in some instances. The plasma port 456 is also used in the blood priming of the vessel 352 in that air is removed from the vessel 352 through the plasma port 456. Referring to FIG. 22, the plasma outlet port assembly 452 includes a plasma outlet port 456 and a plasma outlet tube 476 which is fluidly interconnected therewith exteriorly of the blood processing vessel 352. The plasma outlet port 456 extends through and beyond the inner sidewall 372 of the blood processing vessel 352 into an interior of the blood processing vessel 352. The plasma outlet port 456 is disposed between the second end 364 of the blood processing vessel 352 and the second connector 368.

The plasma outlet port 456 is configured to reduce the potential for the flow therethrough being obstructed during rinseback (i.e., during an attempted evacuation of the blood processing vessel 352 upon completion of an apheresis procedure so as to provide as much of the contents thereof back to the donor/patient 4). During rinseback, the rotation of the channel housing 204 is terminated and a relatively significant drawing action (e.g., by pumping) is utilized to attempt to remove all contents from the blood processing vessel 352. The end of the plasma outlet port 456 includes a first protrusion 460 and a second protrusion 464 displaced therefrom, with a central recess 468 being disposed therebetween which contains an orifice 472 for the plasma outlet port 456. The first protrusion 460 and the second protrusion 464 each extend further beyond the inner sidewall 372 of the blood processing vessel 352 a greater distance then the central recess 468. As such, during rinseback if the outer sidewall 376 attempts to contact the inner sidewall 372, the first protrusion 460 and second protrusion 464 will displace the central recess 468 and its orifice 472 away from the outer sidewall 376. This retains the orifice 472 in an open condition such that the flow therethrough is not obstructed during rinseback.

In order to further assist in withdrawal from the blood processing vessel 352 after completion of an apheresis procedure and thus during rinseback, a first passageway 480 and a second passageway 484 are formed in the blood processing vessel 352 (e.g., via heat seals, RF seals) and generally extend downwardly from the plasma outlet port 456 toward a lower portion of the blood processing vessel 352. The first passageway 480 and second passageway 484 are disposed on opposite sides of the plasma outlet port 456. With this configuration, a drawing action through the plasma outlet port 456 is initiated in a lower portion of the blood processing vessel 352 at two displaced locations.

Figure 23A:
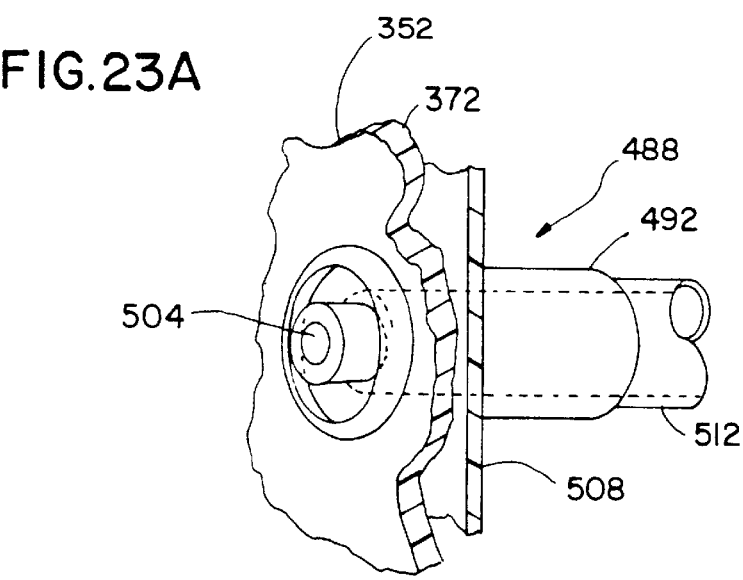
FIG. 23A is a cutaway, perspective view of the control port assembly for the blood processing vessel of FIG. 8.
Figure 23B:
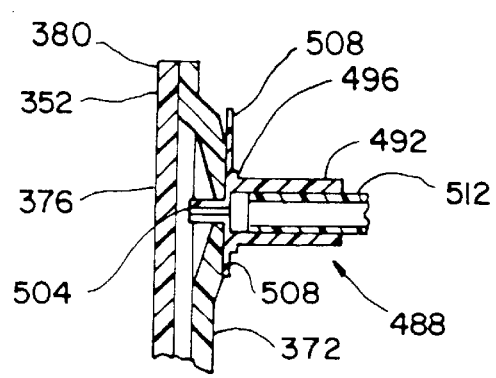
FIG. 23B is a cross-sectional view of the control port assembly interfacing with the blood processing vessel of FIG. 8.
Figure 24:
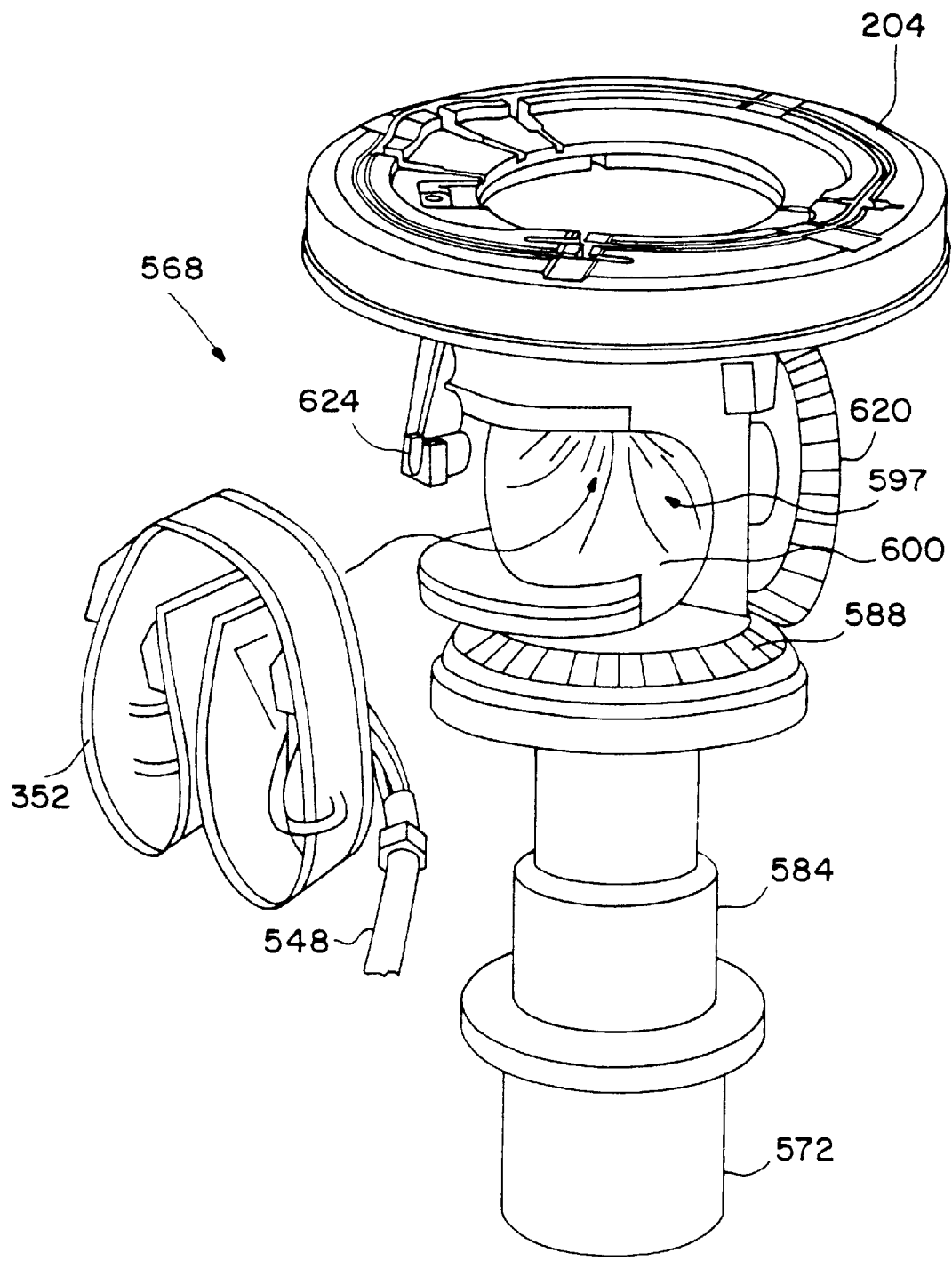
FIG. 24 is a perspective view of the centrifuge rotor assembly for the system of FIG. 1.

Some of the separated plasma is also utilized to automatically control the location of the interface between separated RBCs and the buffy coat in the first stage 312, specifically the radial position of this interface relative to the RBC dam 232. Plasma which provides this interface control function is removed from the blood processing vessel 352 by a control port assembly 488 which is illustrated in FIGS. 23A–B. The control port assembly 488 is disposed in a clockwise direction from the plasma outlet port assembly 452 and proximate the RBC outlet port assembly 516, and thus between the first end 284 of the channel 208 and the RBC outlet port assembly 516. This plasma thus flows from the second stage 316 and into the third stage 320 to provide this function.

The control port assembly 488 generally includes a control port 492 and control port tube 512 which is fluidly interconnected therewith exteriorly of the blood processing vessel 352. The control port 492 extends through and beyond the inner sidewall 372 of the blood processing vessel 352 into an interior portion of the blood processing vessel 352. The radial positioning of the orifice 504 of the control port 492 is not dependent upon the thickness of the material forming the blood processing vessel 352. Instead, the control port 492 includes a shoulder 496 which engages or seats upon structure within the control port slot 264 to accurately place the orifice 504 at a predetermined radial position within the channel 208. Moreover, this predetermined radial position is substantially maintained even after the blood processing vessel is pressurized. In this regard, the control port assembly 488 interfaces with the inner sidewall 372 of the blood processing vessel 352 in a manner which minimizes the discontinuity along the inner channel wall 212 in the region of the control port slot 264 in which the control port 492 is disposed. Specifically, a shield 508 is integrally formed with and disposed about the control port 492. The shield 508 is disposed on an exterior surface of the blood processing vessel 352 and interfaces with its inner sidewall 372. The shield 508 is at least in partial over-lapping relation with the inner sidewall 372. Moreover, in the case where the shield 508 is integrally formed with the port 492, it need not be attached to the inner sidewall 372. Generally, the shield 508 is more rigid than the inner sidewall 372 and this assists in maintaining the orifice 504 of the control port 492 at the desired radial position within the channel 208. This increased rigidity may be provided by utilizing a more rigid material for the shield 508 than is used for the inner sidewall 372. For instance, the durometer rating of the material forming the shield 508 may range from about 90 Shore A to about 130 Shore A, while the durometer rating of the material forming the inner sidewall 372 of the blood processing vessel 352 again ranges from about 50 Shore A to about 90 Shore A in one embodiment.

The control port assembly 488 and the RBC outlet port assembly 516 function in combination to control the radial position of the interface between separated RBCs and the buffy coat relative to the RBC dam 232. Two structural differences between the RBC outlet port assembly 516 and the control port assembly 488 contribute to achieving this automatic control. Initially, the orifice 536 to the RBC outlet port 520 is disposed further into the interior of the blood processing vessel 352 than the control port 492. In one embodiment, the orifice 538 of the RBC outlet port 520 is disposed more radially outwardly than the orifice 504 of the control port 492. Moreover, the diameter of the RBC outlet tube 540 is greater than that of the control port tube 512. In one embodiment, the inner diameter of the RBC outlet tube 54 is about 0.094", while the inner diameter of the control port tube 512 is about 0.035". The control port tube 512 and RBC outlet tube 540 also join into a common return tube 546 via a three-way tubing jack 544 which further assists in providing the automatic interface control feature.

The automatic interface position control is provided as follows utilizing the RBC outlet port assembly 516 and the control port assembly 488. Initially, there are two interfaces in the channel 208 of significance with regard to this automatic interface position control feature. One of these interfaces is the RBC/buffy coat interface in relation to the RBC dam 232. However, there is also an RBC/plasma interface in the region of the control port assembly 488 which again is available through use of the control port dam 280. The control port dam 280 allows substantially only RBCs to flow to the control port assembly 488 in a counterclockwise direction.

In the event that the interface between the RBCs and plasma moves radially inwardly toward the rotational axis 324, RBCs will begin flowing out the control port tube 512 in addition to the RBC outlet tube 540. This decreases the flow through the smaller diameter control port tube 512 due to the higher viscosity and density of the RBCs compared to the plasma which typically flows through the control port tube 512. Consequently, the flow through the larger diameter RBC outlet tube 540 must increase since the flow through the return tube 546 must remain the same. This removes more RBCs from the first stage 312 such that both the interface between the RBCs and the buffy coat in relation to the RBC dam 232 and the interface between the RBCs and the plasma both move radially outwardly. That is, this changes the radial position of each of these interfaces. As such, the potential for RBCs flowing beyond the RBC dam 232 and into the platelet collect well 236 is reduced.

In the event that the location of the interface between the RBCs and plasma progresses radially outward, the flow through the control port tube 512 will increase since the quantity of RBCs exiting the blood processing vessel 352 through the control port 512 will have decreased. Since the flow through the return tube 546 must remain the same, this results in a decrease in the flow of RBCs through the RBC outlet tube 540. This reduces the number of RBCs being removed from the channel 208 such that both the interface between the RBCs and the buffy coat in relation to the RBC dam 232 and the interface between the RBCs and the plasma both move radially inwardly. That is, this changes the radial position of each of these interfaces.

The above-described tubes which interface with the blood processing vessel 352, namely the blood inlet tube 412, the platelet collect tube 424, the plasma outlet tube 476, the return tube 546, each pass downwardly through the central opening 328 in the channel housing 204. A tubing jacket 548 is disposed about these various tubes and protects such tubes during rotation of the channel housing 204. These tubes are also fluidly interconnected with the extracorporeal tubing circuit 10 which again provides for fluid communication between the donor/patient 4 and the blood processing vessel 352.

The blood processing vessel 352 also includes features for loading and unloading the same from the channel 208. Referring back to FIG. 16, the vessel 352 includes at least one and preferably a plurality of tabs 552. The tabs 552 may be integrally formed with the blood processing vessel 352 (e.g., formed by the seal which also forms the upper seal 380). However, the tabs 552 may also be separately attached. The tabs 552 nonetheless extend vertically above the fluid-containing volume of the blood processing vessel 352, preferably a distance such that the tabs 552 actually project above the channel housing 204. The tabs 552 thereby provide a convenient non-fluid-containing structure for the operator to grasp and load/remove the blood processing vessel 352 into/from the channel 208 (i.e., they provide structure for the operator to grasp which has had no blood-related flow therethrough during the apheresis procedure). The tabs 552 are particularly useful since there may be resistance provided to a loading and an unloading of the blood processing vessel 352 into/from the channel 208.

Centrifuge Rotor Assembly

The channel assembly 200 is mounted on the centrifuge rotor assembly 568 which rotates the channel assembly 200 to separate the blood into the various blood component types by centrifugation. The centrifuge rotor assembly 568 is principally illustrated in FIGS. 24–25 and generally includes a lower rotor housing 584 having a lower gear 588. An input or drive shaft 576 is disposed within the lower rotor housing 584 and is rotatably driven by an appropriate motor 572. The input/drive shaft 576 includes a platform 580 mounted on an upper portion thereof and a rotor body 592 is detachably interconnected with the platform 580 such that it will rotate therewith as the input/drive shaft 576 is rotated by the motor 572.

The centrifuge rotor assembly 568 further includes an upper rotor housing 632 which includes a mounting ring 644 on which the channel housing 204 is positioned. In order to allow the channel housing 204 to rotate at twice the speed of the rotor body 592, the upper rotor housing 632 and lower rotor housing 584 are rotatably interconnected by a pinion assembly 612. The pinion assembly 612 is mounted on the rotor body 592 and includes a pinion mounting assembly 616 and a rotatable pinion 620. The pinion 620 interfaces with the lower gear 588 and a driven gear 636 which is mounted on the mounting ring 644. The gear ratio is such that for every one revolution of the rotor body 592, the upper rotor housing 632 rotates twice. This ratio is desired such that no rotary seals are required for the tubes interfacing with the blood processing vessel 352. In one embodiment, the lower gear 588, the pinion 620, and the driven gear 636 utilize straight bevel gearing.

The centrifuge rotor assembly 568 is also configured for easy loading of the blood processing vessel 352 in the channel 208 of the channel housing 204. In this regard, the rotor body 592 includes a generally L-shaped blood processing vessel loading aperture 597. The aperture 597 includes a lower aperture 600 which extends generally horizontally into the is rotor body 592 through its sidewall 596 of the rotor body 592, but only partially therethrough. The perimeter of the lower aperture 600 is defined by a left concave wall 601, a back concave wall 603, and a right concave wall 602.

The loading aperture 597 also includes an upper aperture 598 which intersects with the lower aperture 600 at 599 and extends upwardly through an upper portion of the rotor body 592. The upper aperture 598 is aligned with a generally vertically extending central opening 640 in the upper rotor housing 632. As noted above, the channel housing 204 also includes a central opening 328. As such, a blood processing vessel 352 may be folded if desired, inserted into the lower aperture 600, deflected upwardly by the back concave wall 603, through the upper aperture 598, through the central opening 640 in the upper rotor housing 632, and through the central opening 328 of the channel housing 204. The operator may then grasp the blood processing vessel 352 and load the same in the channel 208.

The centrifuge rotor assembly 568 includes a number of additional features to facilitate the loading of the blood processing vessel 352 in the channel 208. Initially, the pinion 620 is radially offset in relation to the lower aperture 600 of the rotor body 592. In one embodiment, a reference axis laterally bisects the lower aperture 600 and may be referred to as the "zero axis". The axis about which the pinon 620 rotates is displaced from this "zero axis" by an angle α of about 40° in the illustrated embodiment. An angle α of −40° could also be used. Positioning the pinion 620 at an angle of "greater" than ±40° will result in the pinion 620 beginning to interfere with the access to the loading aperture 597. Although the angle a may be less than 40° and may even be 0°, having the pinion 620 at 0° will result in the counterweights 608 potentially interfering with the access to the loading aperture 597. Based upon the foregoing, in FIG. 25 pinion assembly 612 has therefore been rotated about the axis which the centrifuge rotor assembly 568 rotates for ease of illustration.

Since only a single drive gear is utilized to rotate the upper rotor housing 632 relative to the rotor body 592, an upper counterweight 604 and lower counterweight 608 are disposed or detachably connected to the rotor body 592 proximate the upper and lower extremes of the lower aperture 600. Due to the offset positioning of the pinion 620 in relation to the lower aperture 600, the upper and lower counterweights 604, 608 are also radially offset in relation to the lower aperture 600. That is, the upper and lower counterweights 604, 608 are "off to the side" in relation to the lower aperture 600 such that access thereto is not substantially affected by the counterweights 604 and 608. A tube mounting arm 624 is also appropriately attached to the rotor body 592 and engages the tubing jacket 548. The tubing mounting arm 624 serves to further the rotational balance of the rotor body 592.

Figure 25A:
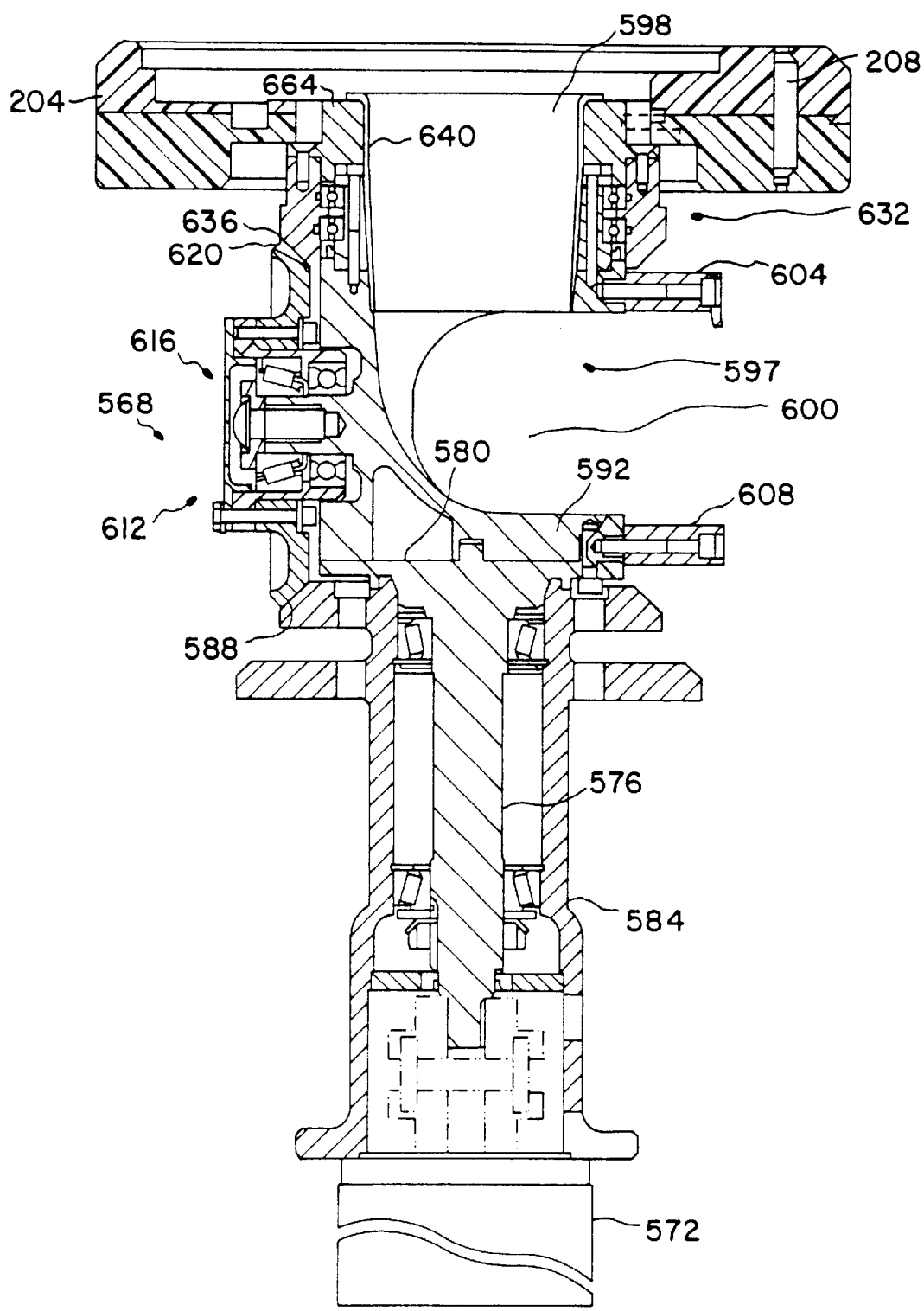
FIG. 25A is a longitudinal cross-sectional view of the rotor assembly of FIG. 24.
Figure 25B:
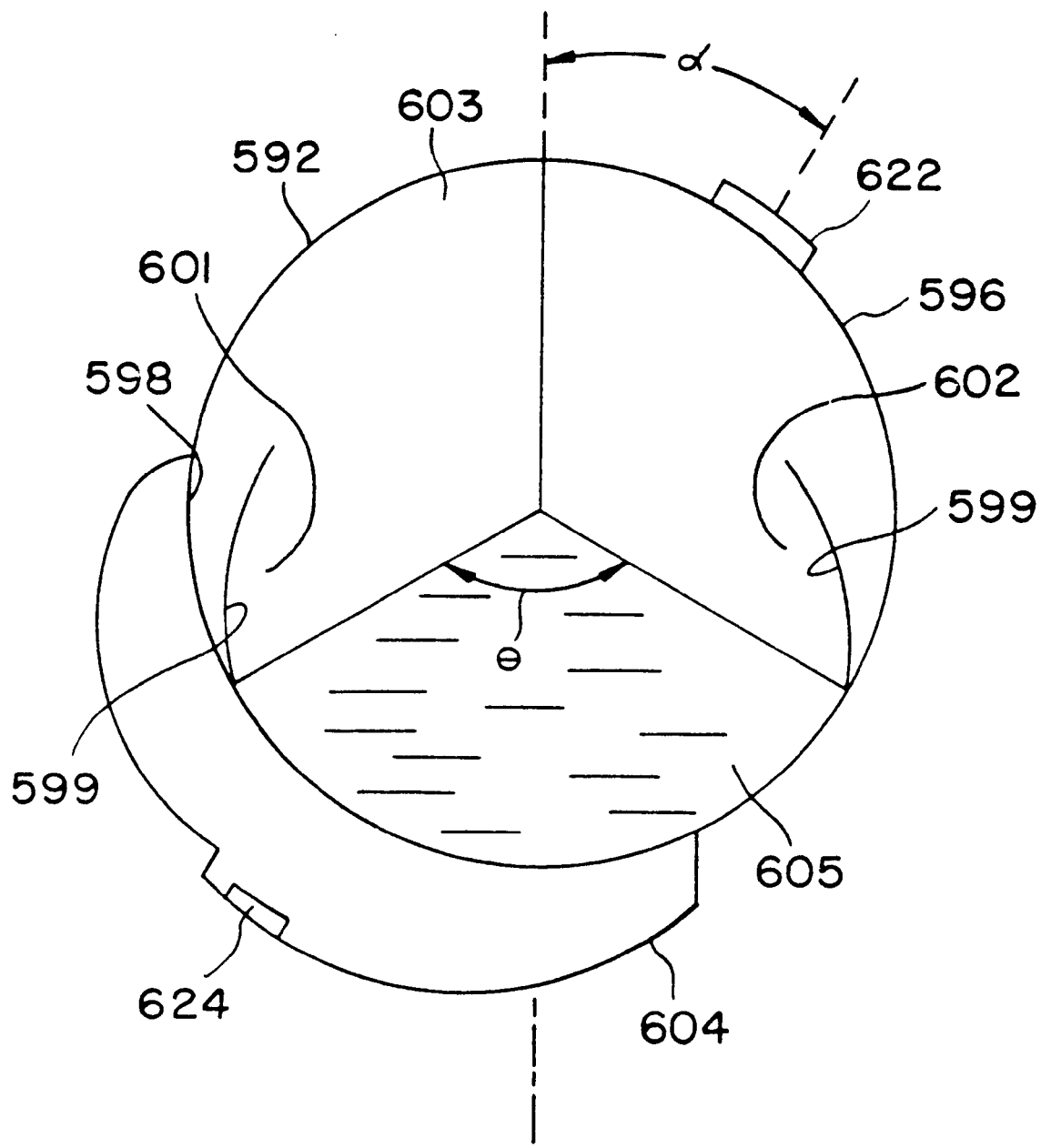
FIG. 25B is a top view of the rotor body of the rotor assembly of FIG. 24.
Figure 25C:
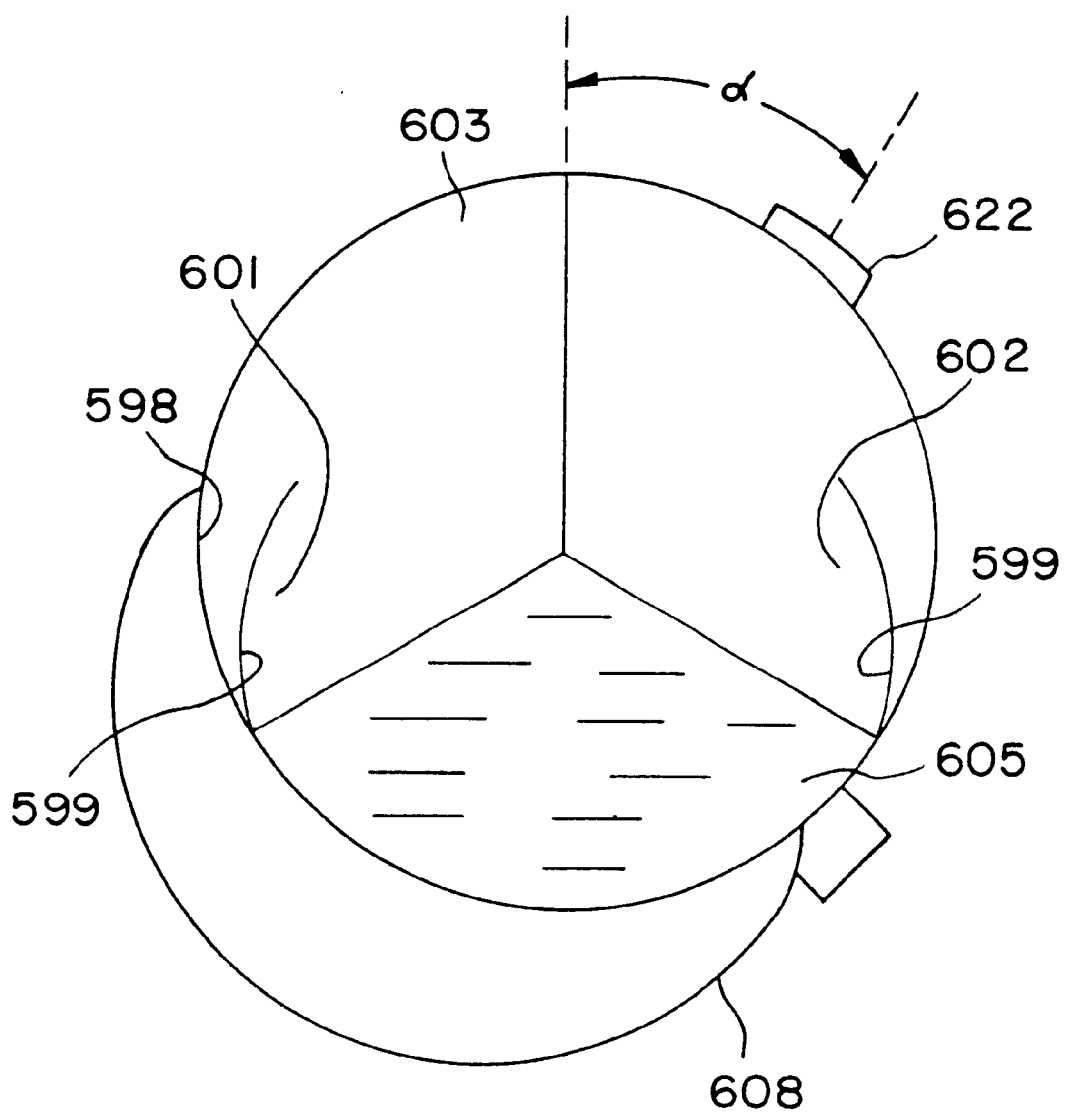
FIG. 25C is a top view of the rotor body of the rotor assembly of FIG. 24 with the upper counterweight removed so as to illustrate the lower counterweight.
Figure 25D:
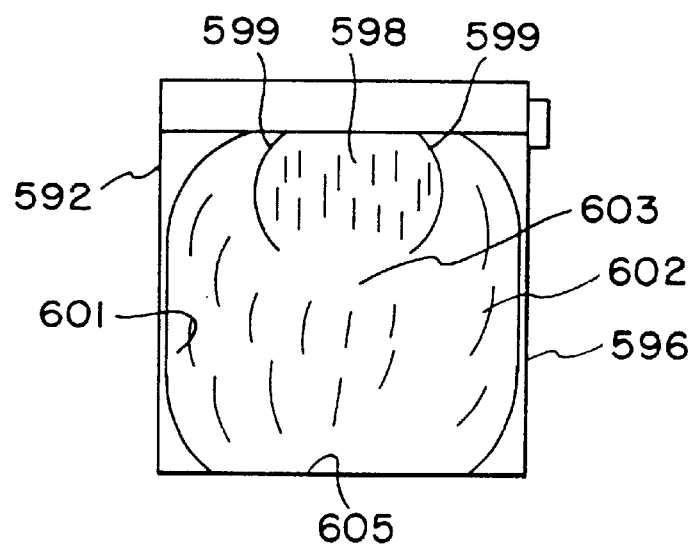
FIG. 25D is a front view of the rotor body of FIG. 24.
Figure 25E:
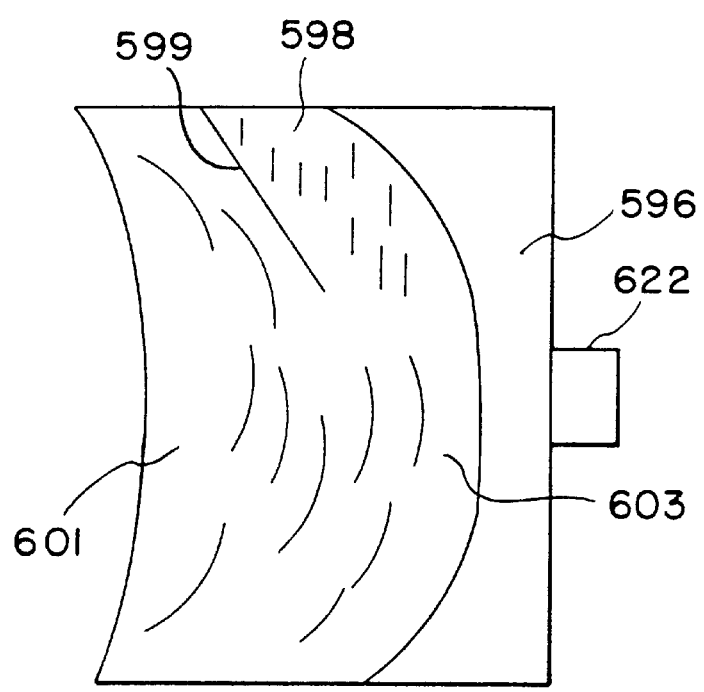
FIG. 25E is a perspective view of the left side of the blood processing vessel aperture in the rotor body of FIG. 24.
Figure 25F:
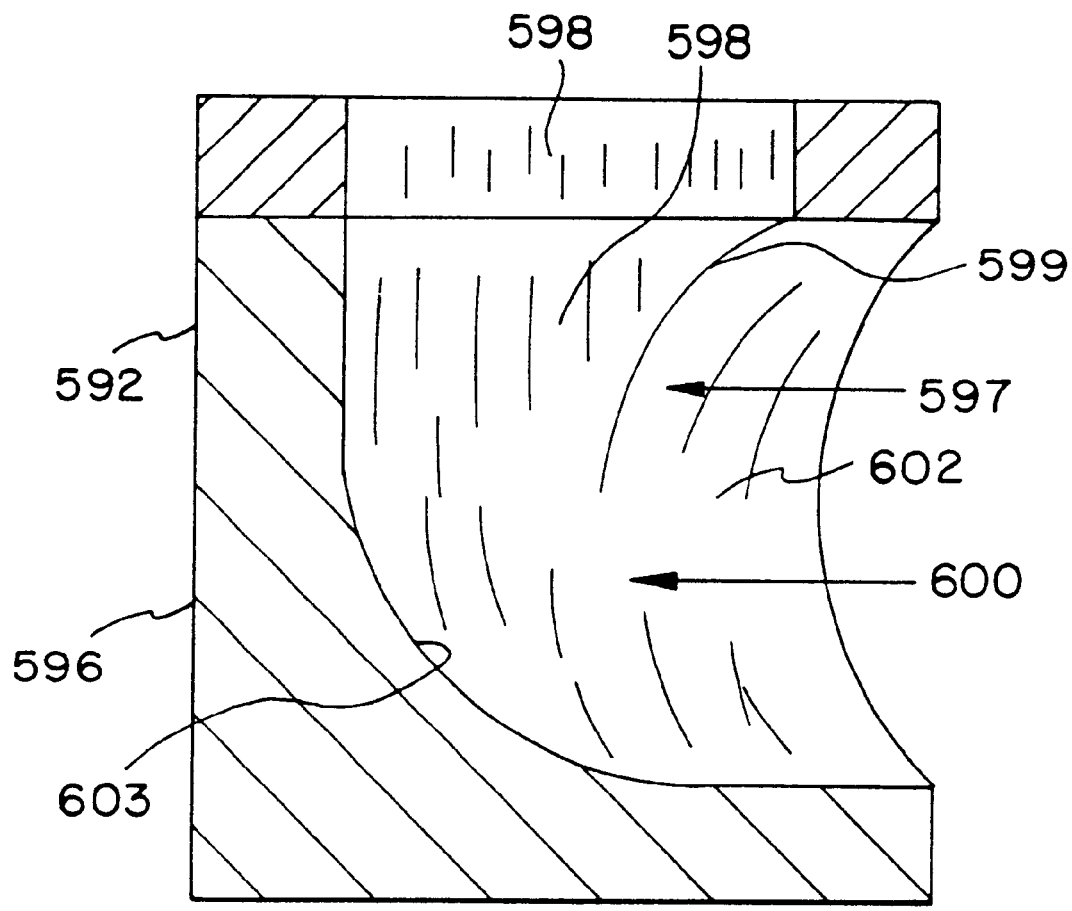
FIG. 25F is a cross-sectional view of the rotor body of FIG. 24.

Another feature of the centrifuge rotor assembly 568 which contributes to the loading of the blood processing vessel 352 upwardly through the rotor body 592 is the size of the lower aperture 600. As illustrated in FIG. 25B, the "width" of the lower aperture may be defined by an angle θ which may range from about 70° to about 90°, and in the illustrated embodiment is about 74°. The back wall 603, left wall 601, and right wall 602 are also defined by a radius ranging from about 1.751" to about 2.250", and in the illustrated embodiment this radius is between about 2.008" and about 2.032".

Apheresis Protocol

One protocol which may be followed for performing an apheresis procedure on a donor/patient 4 utilizing the above-described system 2 will now be summarized. Initially, an operator loads the cassette assembly 110 onto the pump/valve/sensor assembly 1000 of the blood component separation device 6 and hangs the various bags (e.g., bags 104, 94, 84) on the blood component separation device 6. The operator then loads the blood processing vessel 352 within the channel 208 which is disposed on the channel housing 204 which is in turn mounted on the centrifuge rotor assembly 568, particularly the mounting ring 644. More specifically, the operator may fold the blood processing vessel 352 and insert the same into the blood processing vessel loading aperture 597 on the rotor body 592. Due to the arcuately-shaped, concave configuration of the loading aperture 597, specifically the lower aperture 600, the blood processing vessel 352 is deflected upwardly through the upper aperture 598, the central opening 640 in the upper rotor housing, and the central opening 328 in the channel housing 294. The operator then grasps the blood processing vessel 352 and pulls it upwardly away from the channel housing 204.

Once the blood processing vessel 352 has been installed up through the centrifuge rotor assembly 568, the operator loads the blood processing vessel 352 into the channel 208 on the channel housing 204. The operator generally aligns the blood processing vessel 352 relative to the channel 208 (e.g., such that the blood inlet port 392 is vertically aligned with the blood inlet slot 224, such that the platelet collect port 420 is vertically aligned with the platelet support recess 249 and the platelet collect tube recess 254, such that the plasma outlet port 456 is vertically aligned with the plasma outlet slot 256, such that the control port 492 is vertically aligned with the control port slot 264, and such that the RBC outlet port 520 is vertically aligned with the RBC outlet slot 272). Once again, the interconnection of the first connector 360 and second connector 368, which is preferably fixed, facilitates the loading of the blood processing vessel 352, as well as the existence of the chamfer 210.

With the blood processing vessel 352 properly aligned, the operator directs the blood processing vessel 352 through the reduced width upper channel section 292 of the channel 208 until the blood processing vessel 352 hits the channel base 220. In this case, the longitudinal extent of the blood processing vessel 352 located in the portion of the channel 208 which includes the first stage 312, the RBC dam 232, and the platelet collect stage 316 will be disposed as follows: 1) the upper seal 380 will be disposed in the upper channel section 292; 2) the fluid-containing volume of the blood processing vessel 352 will be disposed in the mid channel section 300; and 3) the lower seal 384 will be disposed in the lower channel section 304. The above-noted ports will also be disposed in their respective slots in the channel housing 204 by the operator at this time. Moreover, the shield 408 associated with the blood inlet port assembly 388 will be disposed in the recess 228 associated with the blood inlet slot 224. Similarly, the shield 538 associated with the RBC outlet port assembly 516 will be disposed in the recess 276 associated with the RBC outlet slot 272. Furthermore, the shield 508 associated with the control port assembly 488 will be disposed in the recess 268 associated with the control port slot 264.

With the extracorporeal tubing circuit 10 and the blood processing vessel 352 loaded in the above-described manner, the circuit 10 and vessel 352 are pressure tested to verify that there are no leaks. The donor/patient 4 is then fluidly interconnected with the extracorporeal tubing circuit 10 (by inserting an access needle 32 into the donor/patient 4). Moreover, the anticoagulant tubing 54 is primed between the anticoagulant supply (which interfaces with the spike drip member 52) and the manifold 48. Furthermore, blood return tubing 28 is primed with blood from the donor/patient 4 by running the blood return peristaltic pump 1090 pump in reverse to draw blood from the donor/patient 4, through the blood return tubing 28, and into the reservoir 150 until blood is detected by the low level sensor 1320.

The blood processing vessel 352 must also be primed for the apheresis procedure. In one embodiment, a blood prime may be utilized in that blood will be the first liquid introduced into the blood processing vessel 352. The flow of blood from the donor/patient 4 to the extracorporeal tubing circuit 10 is initiated with the centrifuge rotor assembly 568 rotating the channel housing 204 at a rotational velocity of from about 150 RPM to about 250 RPM for a rotor diameter of about 10", and typically about 200 RPM. This lower rotational velocity not only reduces the potential for air locks developing the in the blood processing vessel 352, but also minimizes any preheating of the blood processing vessel 352. The rotational velocity in this "first stage" need not be fixed, but may vary.

Once the flow of blood reaches the blood processing vessel 352, the rotational speed of the channel housing 204 is increased from about 1,500 RPM to about 2,500 RPM for a rotor diameter of about 10", preferably about 2000 RPM, such that blood being provided to the blood processing vessel 352 will be separated into the various blood component types even during the priming procedure. Once again, in this "second stage", the rotational velocity during need not be fixed, but may vary. In order for a blood prime to be successful, a flow must be provided to the control port assembly 488 before any RBCs flows beyond the RBC dam 232 in a clockwise direction. This is again provided by the configuration of the channel 208.

Importantly, during this "second stage" of the blood priming procedure, air present in the blood processing vessel 352 is removed from the blood processing vessel 352 and due to the noted rotational velocities in this "second stage", the potential for air locks is also reduced. More specifically, air which is present in the blood processing vessel 352 is less dense than the whole blood and all of its blood component types. As noted above, the radially inwardmost portion of the inner channel wall 212 is at the intersection between the plasma outlet slot 256 and the inner channel wall 212. Consequently, the air present in the blood processing vessel 352 collects near the plasma outlet port 456 and is removed from the blood processing vessel 352 through the plasma outlet tubing 476, and is provided to the vent bag 104.

When the blood processing vessel 352 contains blood and/or blood components throughout its entirety, the rotational velocity of the channel housing 204 is increased to its normal operation speed from about 2,750 RPM to about 3,250 RPM for a rotor diameter of about 10", and preferably about 3,000 RPM. This completes the blood priming procedure.

During the above-noted blood priming procedure, as well as throughout the remainder of the apheresis procedure, blood component types are separated from each other and removed from the blood processing vessel 352 on a blood component type basis. At all times during the apheresis procedure, the flow of whole blood is provided to the blood processing vessel 352 through the blood inlet port assembly 416 and is directed to the first stage 312. The control port dam 280 again reduces the potential for blood flowing in a counterclockwise direction in the channel 208.

In the first stage 312, blood is separated into a plurality of layers of blood component types including, from the radially outermost layer to the radially innermost layer, RBCs, WBCs, platelets, and plasma. As such, the RBCs sediment against the outer channel wall 216 in the first cell separation stage 312. By configuring the RBC dam 232 such that it is a section of the channel 210 which extends further inwardly toward the rotational axis 324 of the of the channel housing 204, this allows the RBC dam 232 to retain separated red blood cells in the first stage 312.

Separated RBCs are removed from the first stage 312 utilizing the above-noted configuration of the outer channel wall 216 which induces the RBCs to flow in a counterclockwise direction (e.g., generally opposite to the flow of blood through the first cell separation stage 312). That is, the portion of the channel 208 proximate the RBC outlet port assembly 516 is disposed further from the rotational axis 324 of the channel housing 204 than that portion of the channel 210 proximate the RBC dam 232. As such, separated RBCs flow through the first stage 312 in a counterclockwise direction along the outer channel wall 216, past blood inlet port assembly 388 on the blood processing vessel 352, and to an RBC outlet port assembly 516. Since the vertical slot 404 of the blood inlet port 392 is substantially parallel with the inner channel wall 212, the outer channel wall 216, the inner sidewall 372 of the blood processing vessel 352 and the outer sidewall 376 of the blood processing vessel 352, since it directs the flow of blood in a clockwise direction in the channel 208 and thus toward the RBC dam 232, since it is disposed proximate the inner channel wall 212, the introduction of blood into the blood processing vessel 352 does not substantially affect the flow of RBCs along the outer channel wall 216. Consequently, RBCs effectively flow undisturbed past the blood inlet port 392 and to the RBC outlet port assembly 516 for removal from the blood processing vessel 352. These RBCs may either be collected and/or provided back to the donor/patient 4.

Platelets are less dense then RBCs and are thus able to flow beyond the RBC dam 232 and to the platelet collect well 236 in platelet-rich plasma where they are removed from the blood processing vessel 352 by the platelet collect port assembly 416. Again, the blood processing vessel 352 via the support 428 and the outer channel wall 216 collectively define the platelet collect well 236 when the blood processing vessel 352 is pressurized. That is, part of the platelet collect well 236 is defined by the lower face 240 and side faces 244, 248 formed in the outer channel wall 216, while the remainder thereof is defined by the second face 436 of the support 428 when the support 428 is moved into a predetermined position within and against portions of platelet support recess 249 upon pressurization of the blood processing vessel 352.

Platelet-poor plasma is less dense than the platelets and continues to flow in a clockwise direction through the second stage 316 to the plasma outlet port assembly 452 where at least some of the plasma is removed from the blood processing vessel 352. This plasma may be collected and/or returned to the donor/patient 4. However, some of the plasma flow continues in the clockwise direction into and through the third stage 320 to the control port assembly 488 to provide for automatic control of the location of the interface between the RBCs and platelets in the above-described manner.

Graphical Computer Interface

In order to assist an operator in performing the various steps of the protocol being used in an apheresis procedure with the apheresis system 2, the apheresis system 2 further includes a computer graphical interface 660 illustrated in FIG. 1. The following description describes an interface for use by an English language speaking operator. For other operations and/or languages, the textual portions of the interface would, of course, be adapted accordingly. The graphical interface 660 includes a computer display 664 which has "touch screen" capabilities. Other appropriate input devices (e.g., keyboard) may also be utilized alone or in combination the touch screen. For example, a pump pause and a centrifuge stop button of the well known membrane type may be provided. The graphics interface 660 not only allows the operator to provide the necessary input to the apheresis system 2 such that the parameters associated with operation of the apheresis system may be determined (e.g, data entry to allow determination of various control parameters associated with the operation of the apheresis system 2), but the interface 660 also assists the operator by providing pictorials of at least certain steps of the apheresis procedure. Moreover, the interface 660 also effectively conveys the status of the apheresis procedure to the operator. Furthermore, the interface 660 also may be used to activate standardized corrective actions (i.e., such that the operator need only identify the problem and indicate the same to the interface 660 which will then direct the apheresis system 2 to correct the same).

Figure 26:
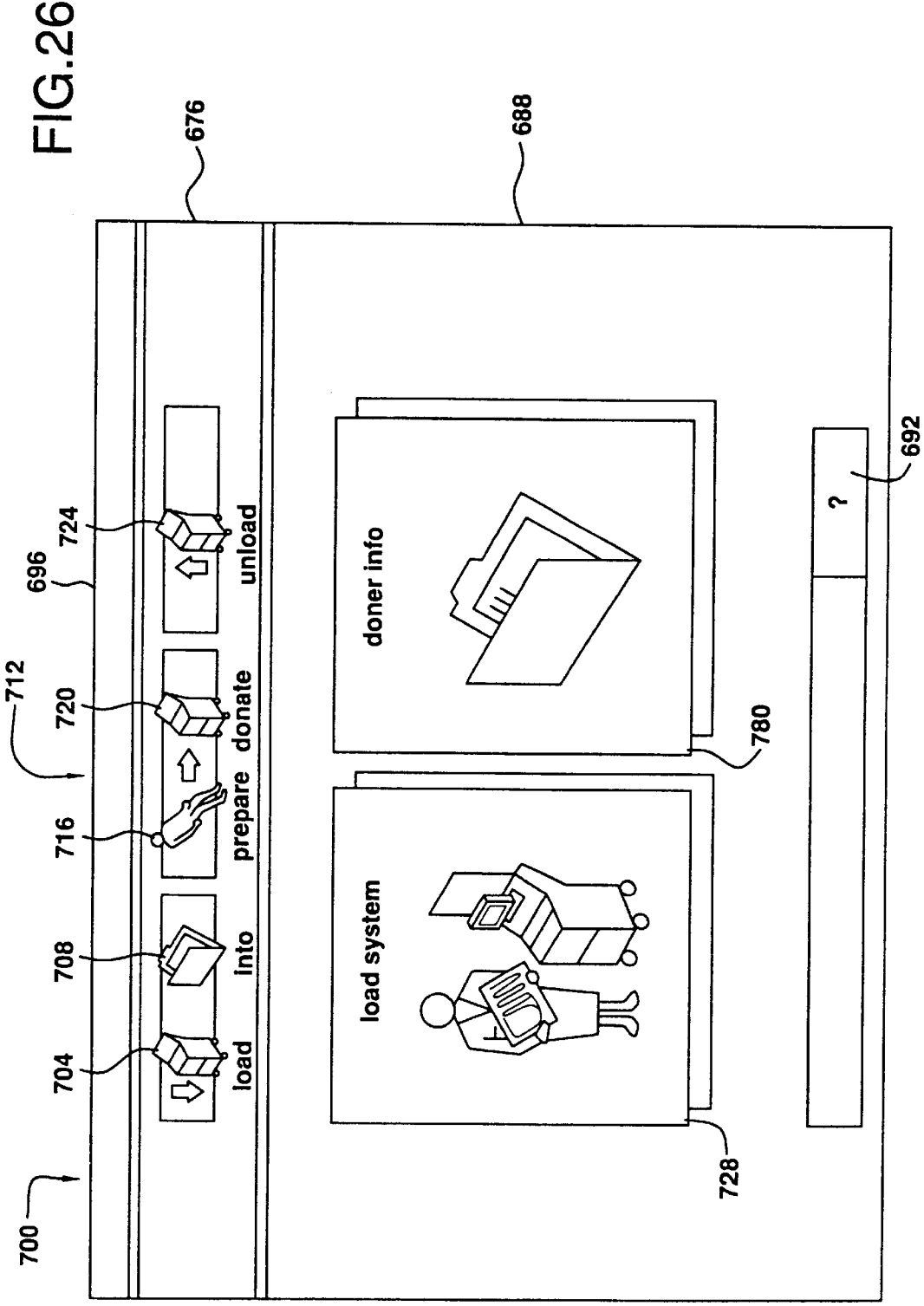
FIG. 26 is a "master screen" for the computer graphics interface of the apheresis system of FIG. 1.

Referring to FIG. 26, at the start of an apheresis procedure a master screen 696 is displayed to the operator on the display 664. The master screen 696, as well as each of the screens displayed to the operator by the interface 600, includes a status bar 676. The status bar 676 includes a system prep icon set 700. The system prep icon set 700 includes a load icon 704 (representing the shape of blood component separation device 6) with a downwardly extending arrow which collectively pictorially conveys to the operator that the disposable set 8 must be loaded onto the blood component separation device 6. The word "LOAD" is also positioned below the load icon 704 to provide a short textual instruction to the operator of the required action(s).

The system prep icon set 700 also includes an information icon 708 (representing the shape of an open filing folder) which pictorially conveys to the operator that certain information relating to the donor/patient 4, the procedure protocol, and/or the blood component separation device 6 must be obtained and entered. This information may be utilized by the apheresis system 2 to calculate one or more of the parameters associated with the apheresis procedure (e.g., inlet flow rate to the blood processing vessel 352) and/or to generate predicted yields of one or more blood component types (e.g., the amount of a certain blood component type which is anticipated to be collected based upon certain parameters such as donation time). The word "INFO" is also positioned below the information icon 708 to provide a short textual instruction to the operator of the required action(s). The information icon 708 is also positioned to the right of the load icon 704 to indicate to the operator that it is preferred, although not required, to perform the step(s) associated with the information icon 708 after the step(s) associated with the load icon 704 have been completed.

The status bar 676 also includes a collection icon set 712. The collection icon set 712 includes a donor/patient prep icon 716 (representing the shape of the donor/patient 4) which pictorially conveys to the operator that the donor/patient 4 must now be fluidly interconnected with the blood component separation device 6. The word "PREPARE" is also positioned below the donor/patient prep icon 716 to provide a short textual instruction to the operator of the required action(s). The donor/patient prep icon 716 is also positioned to the right of the information icon 708 to indicate to the operator that the step(s) associated with the donor/patient prep icon 716 may only be performed after the step(s) associated with the load icon 704 and the information icon 708 have been completed.

The collection icon set 712 also includes a donate icon 720 with a laterally extending arrow which collectively pictorially conveys to the operator that the actual collection procedure may be initiated and that the step(s) to initiate this action should now be performed. The word "DONATE" is also positioned below the donate icon 720 to provide a short textual instruction to the operator of the required action(s) The donate prep icon 720 is also positioned to the right of the donor/patient prep icon 716 to indicate to the operator that the step(s) associated with the donate icon 720 must be performed after the step(s) associated with the donor/patient prep icon 716 have been completed.

The status bar 676 also includes an unload icon 724 (representing the shape of the blood component separation device 6) and a generally upwardly extending arrow which collectively pictorially convey to the operator that the disposable set must now be removed from the blood component separation device 6. The word "UNLOAD" is also positioned below the unload icon 724 to provide a short textual instruction to the operator of the required action(s). The unload icon 724 is also positioned to the right of the donate icon 720 to indicate to the operator that the step(s) associated with the unload icon 724 must be performed after the step(s) associated with the donate icon 720 have been completed.

The system preparation icon set 700, collection icon set 712, and unload icon 724 in the status bar 676 sequentially set forth certain basic steps for the apheresis procedure. That is, the left to right positioning of the various icons conveys to the operator the desired/required order in which the step(s) associated with the icons should/must be performed. Moreover, the individual icons 704, 708, 716, 720, and 724 are also utilized to convey the status of the apheresis procedure to the operator via three-way color differentiation (i.e., one status per color) and/or by three-way shade differentiation. "Shades" includes variations of a given color and also encompasses using variations based upon being "lighter" and/or "darker" (e.g., using light gray, medium gray, and dark gray). That is, a "gray-scale" technique may also be utilized and is encompassed by use of color and/or shade differentiation.

The first status conveyed to the operator by the icons in the status bar 676 is that the step(s) associated with respective icon are not ready to be performed. That is, the performance of this step(s) would be premature. This first status is conveyed to the operator by displaying the associated icon in a first color, such as white. The corresponding textual description may also be presented in this first color as well. As noted, a first "shade" may also be utilized to convey this first status as well.

The second status conveyed to the operator by the icons in the status bar 676 is that the step(s) associated with the respective icon is either ready for execution or is in fact currently being executed. That is, an indication is provided to the operator that performance of this step(s) of the apheresis procedure is now timely. This second status is conveyed to the operator by displaying the associated icon in a second color, such as yellow. The corresponding textual description may also be presented in this second color as well. As noted, second "shade" may also be utilized to convey this second status as well.

The third status conveyed to the operator by the icons in the status bar 676 is that the step(s) associated with the respective icon has been executed. That is, an indication is provided to the operator that performance of this step(s) of the apheresis procedure has been completed. This third status is conveyed to the operator by displaying the associated icon in a third color, such as gray. The corresponding textual description may also be presented in this third color as well. As noted, third "shade" may also be utilized to convey this third status as well.

Based upon the foregoing, it will be appreciated that significant information is conveyed to the operator by merely viewing the status bar 676. For instance, the operator is provided with a pictorial graphic indicative of the fundamental steps of an apheresis procedure. Moreover, the operator is provided with a textual graphic indicative of the fundamental steps of an apheresis procedure. Furthermore, the operator is provided with a desired/required order in which these steps should/must be performed. Finally, the operator is provided with the status of the apheresis procedure via the noted three-way color/shade differentiation.

The master screen 696, as well all other screens displayed to the operator by the interface 660 during an apheresis procedure, also include a work area 688. The work area 688 provides multiple functions. Initially, the work area 688 displays additional information (pictorially and textually in some instances) on performing the apheresis procedure to the operator (e.g., certain additional substeps of the apheresis procedure, addressing certain "conditions" encountered during the apheresis procedure). Moreover, the work area 688 also displays additional information on the status of the apheresis procedure to the operator. Furthermore, the work area 688 also provides for operator interaction with the computer interface 660, such as by allowing/requiring the operator to input certain information.

Continuing to refer to FIG. 26, the work area 688 of the master screen 696 displays a load system button 728 and a donor/patient info button 780. The operator may touch either of these buttons 728, 780 (i.e., since the display 696 has "touch screen" capabilities) to generate further screens for providing information to the operator and/or to facilitate the inputting of information to the computer interface 660. The operator may initially touch either the load system button 728 or the donor/patient info button 780 at the start of an apheresis procedure. That is, the order in which the step(s) associated with the load system button 728 are performed in relation to the apheresis step(s) associated with the donor/patient info button 780 are performed is not important (i.e., the steps associated with the load system button 728 may be performed before or after the steps associated with the donor/patient info button 780). The apheresis procedure will be described with regard to the operator electing to initially activate the load system button 728 via the touch screen feature.

Figure 27:
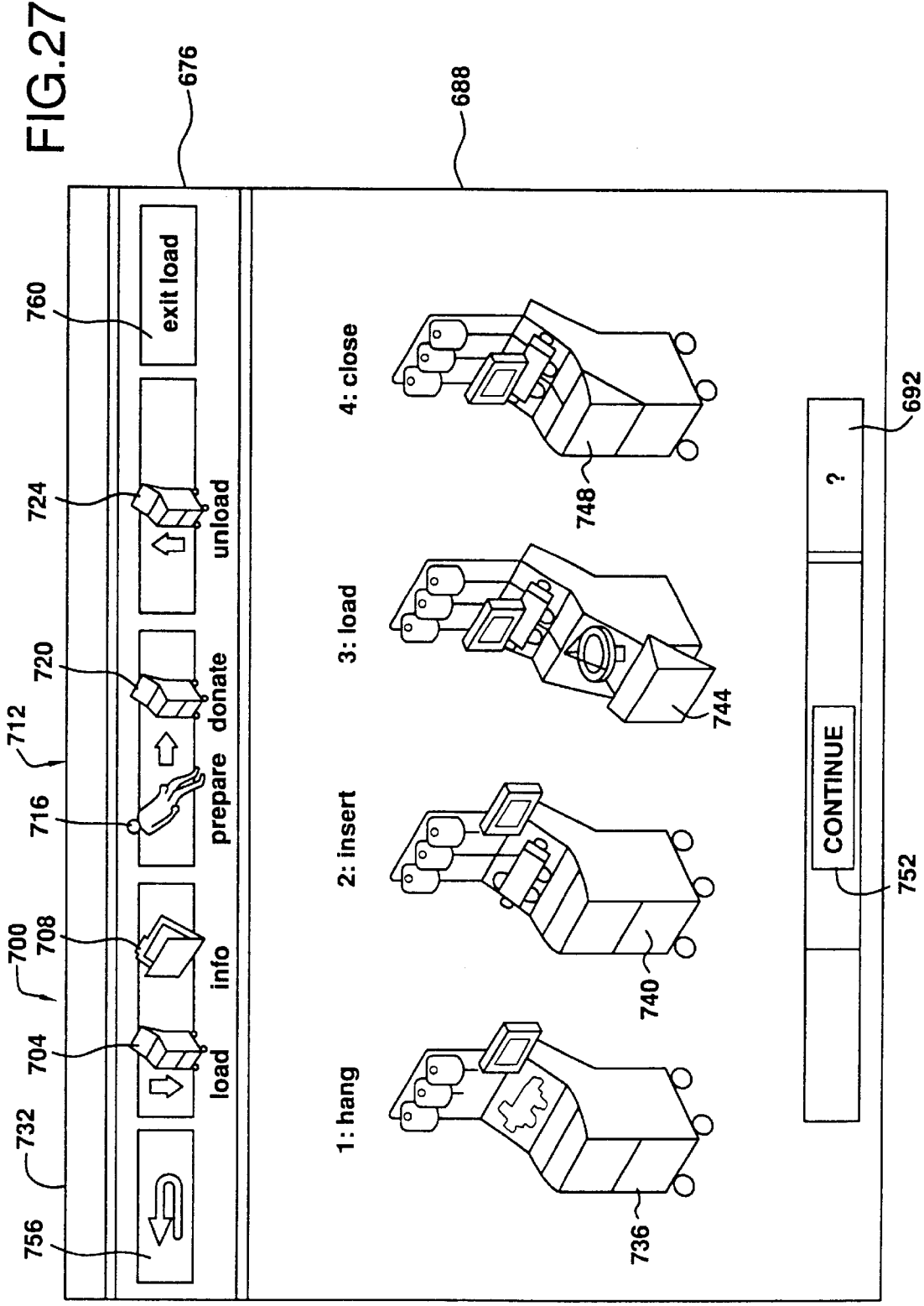
FIG. 27 is a "loading procedures screen" for the computer graphics interface of the apheresis system of FIG. 1.

Activation of the load system button 728 generates a loading procedure screen 732 on the computer display 664 which is illustrated in FIG. 27. The loading procedure screen 732 displays multiple pictorials to the operator in the work area 688 which relate to the steps which need to be performed to prepare the blood component separation device 6 for an apheresis procedure. Initially, a hang pictorial 736 is displayed which pictorially conveys to the operator that the various bags (e.g., an AC bag(s) (not shown), plasma collect bag(s) 94 platelet collect bag(s) 84) need to be hung on the blood component separation device 6 and generally how this step may be affected by the operator. The word "HANG" is also positioned above the hang pictorial 736 to provide a short textual instruction to the operator of the required action(s). Consequently, there are two different types of graphical representations provided to the operator relating to a specific operator action which is required to prepare the blood component separation device 6 for the apheresis procedure. Moreover, the hang pictorial 736 is disposed on the left side of the loading procedure screen 732 which indicates that this is the first step or substep associated with the load icon 704. In order to provide further indications of the desired order to the operator, the number "1" is also disposed adjacent to the word "HANG."

A focus color (e.g., yellow) or shade may be used to direct the operator's attention to specific areas of the machine or screen. The loading procedure screen 732 also displays an insert pictorial 740 to the operator in the work area 688. The insert pictorial 740 pictorially conveys to the operator that the cassette assembly 110 needs to be mounted on the pump/valve/sensor assembly 1000 of the blood component separation device 6 an d generally how this step may be affected by the operator. The word "INSERT" is also positioned above the insert pictorial 740 to provide a short textual instruction to the operator of the required action(s). The insert pictorial 740 is also positioned to the right of the hang pictorial 736 to indicate to the operator that it is preferred, although not required, to perform the step(s) associated with the insert pictorial 740 after the step(s) associated with the hang pictorial 736 have been completed. In order to provide further indications of the desired order to the operator, the number "2" is also disposed adjacent to the word "INSERT."

The loading procedure screen 732 also displays a load pictorial 744 to the operator in the work area 688. The load pictorial 744 pictorially conveys to the operator that the blood processing vessel 352 needs to be loaded into the channel 208 of the channel housing 204 on the centrifuge rotor assembly 568 and generally how this step may be affected by the operator. The word "LOAD" is also positioned above the load pictorial 744 to provide a short textual instruction to the operator of the required action(s). The load pictorial 744 is also positioned to the right of the insert pictorial 740 to indicate to the operator that it is preferred, although not required, to perform the step(s) associated with the load pictorial 744 after the step(s) associated with the insert pictorial 740 have been completed. In order to provide further indications of the desired order to the operator, the number "3" is also disposed adjacent to the word "LOAD."

Finally, the loading procedure screen 732 displays a close pictorial 748. The close pictorial 748 pictorially conveys to the operator that the door of the blood component collection device housing the centrifuge rotor assembly 568 needs to be closed and generally how this step may be affected by the operator. The word "CLOSE" is also positioned above the close pictorial 748 to provide a short textual instruction to the operator of the required action(s). The close pictorial 748 is also positioned to the right of the load pictorial 744 to indicate to the operator that it is required to perform the step(s) associated with the close pictorial 748 after the step(s) associated with the load pictorial 744 have been completed. In order to provide further indications of the desired order to the operator, the number "4" is also disposed adjacent to the word "CLOSE."

In summary, the work area 688 of the loading procedure screen 732 not only conveys to the operator what type of steps must be performed for this aspect of the apheresis procedure and generally how to perform these steps, the work area 688 of the loading procedure screen 732 also specifies the order in which these steps should be performed by two "methods." Initially, the pictorial graphics 736, 740, 744 and 748 are sequentially displayed in left-to-right fashion to specify the desired/required order of performance. Moreover, the four steps are also numerically identified next to their associated one-word textual description.

Figure 28:
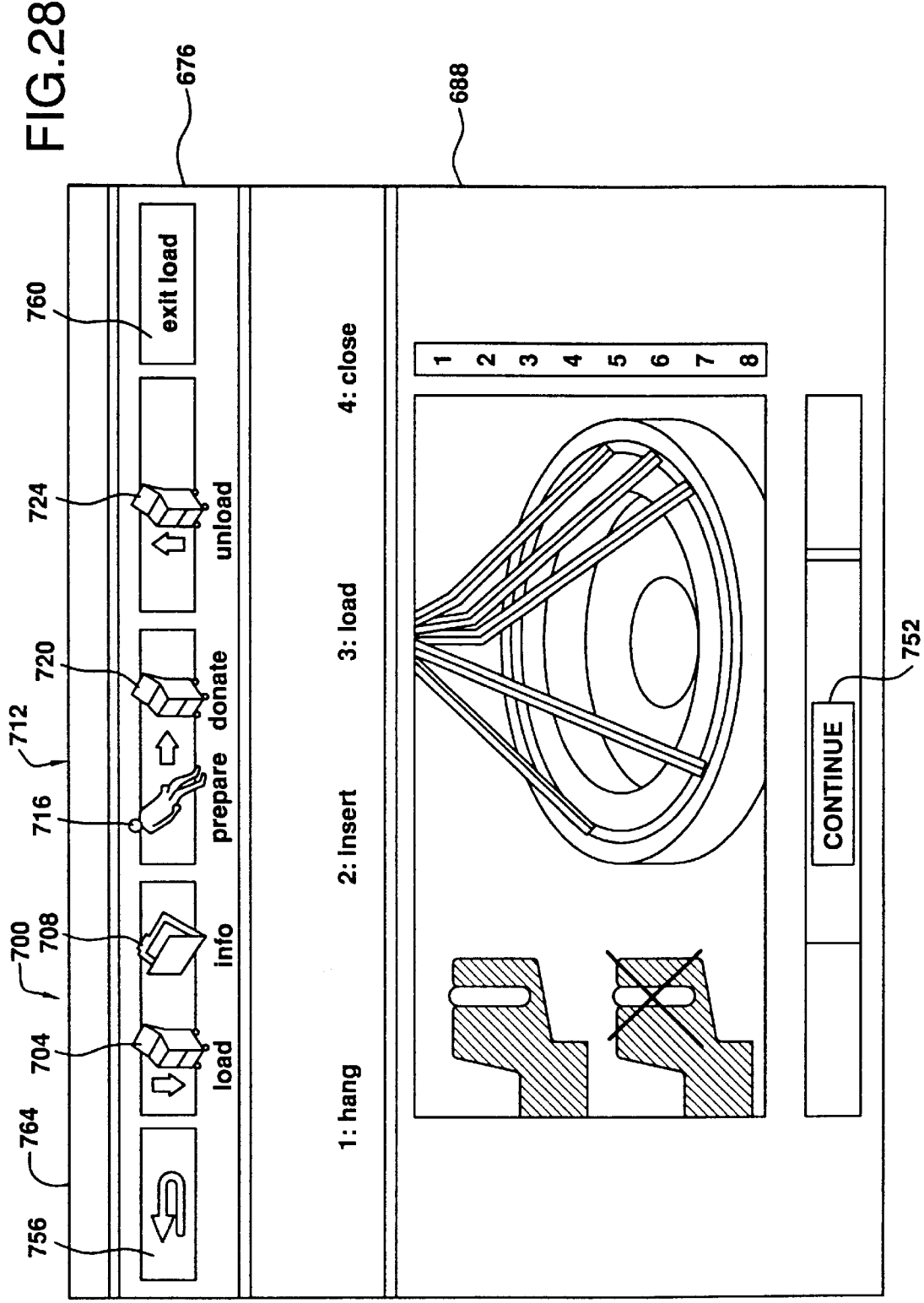
FIG. 28 is one embodiment of a "help screen" for the loading procedures screen of FIG. 27.

In the event that the operator requires additional guidance with regard to any of the steps presented on the loading procedure screen 732, the operator may touch the help button 692 provided on the loading procedure screen 732. This may display a menu of screens which the operator may view and/or may sequentially present a number of help screens associated with the loading procedure screen 732. FIG. 28 illustrates a help screen 764 which relates to the loading of the blood processing vessel 352 into the channel 208 on the channel housing 204. Note that in the case of the help screen 764 the upper portion of the work area 688 of the loading procedure screen 732 is retained (i.e., the one word textual descriptions of the four basic steps and the associated numerical ordering identifier). Moreover, the help screen 764 provides the operator with more detail, in the nature of additional pictorials, regarding one or more aspects of the particular step(s) or substep or in this case on the loading of the blood processing vessel 352 in the channel 208. Once the operator exits the help screen 764 via touching the continue button 752 on the help screen 764, the operator is returned to the loading procedure screen 732 of FIG. 22. Various other screens in the graphics interface 660 may include a help button 692 to provide this type of feature.

When the operator has completed each of the four steps or substeps presented on the loading procedure screen 732, the operator touches the continue button 752 on the bottom of the loading procedure screen 732. In the event that during the time in which the operator is performing the steps or substeps associated with the loading procedure screen 732 the operator wants to return to the begin operations screen 696, the operator may touch the display screen 664 in the area of the return button 756. The return button 756 may be provided on various of the screens to return the operator to the previous screen when acceptable. Moreover, in the event that during the time in which the operator is performing the steps or substeps associated with the loading procedure screen 732 the operator wants to terminate the loading procedure, the operator may touch the display screen 664 in the area of the exit load or cancel button 760. The exit load or cancel button 760 may be provided on various of the other screens to provide the operator with the option to exit the loading procedure where appropriate.

Figure 29:
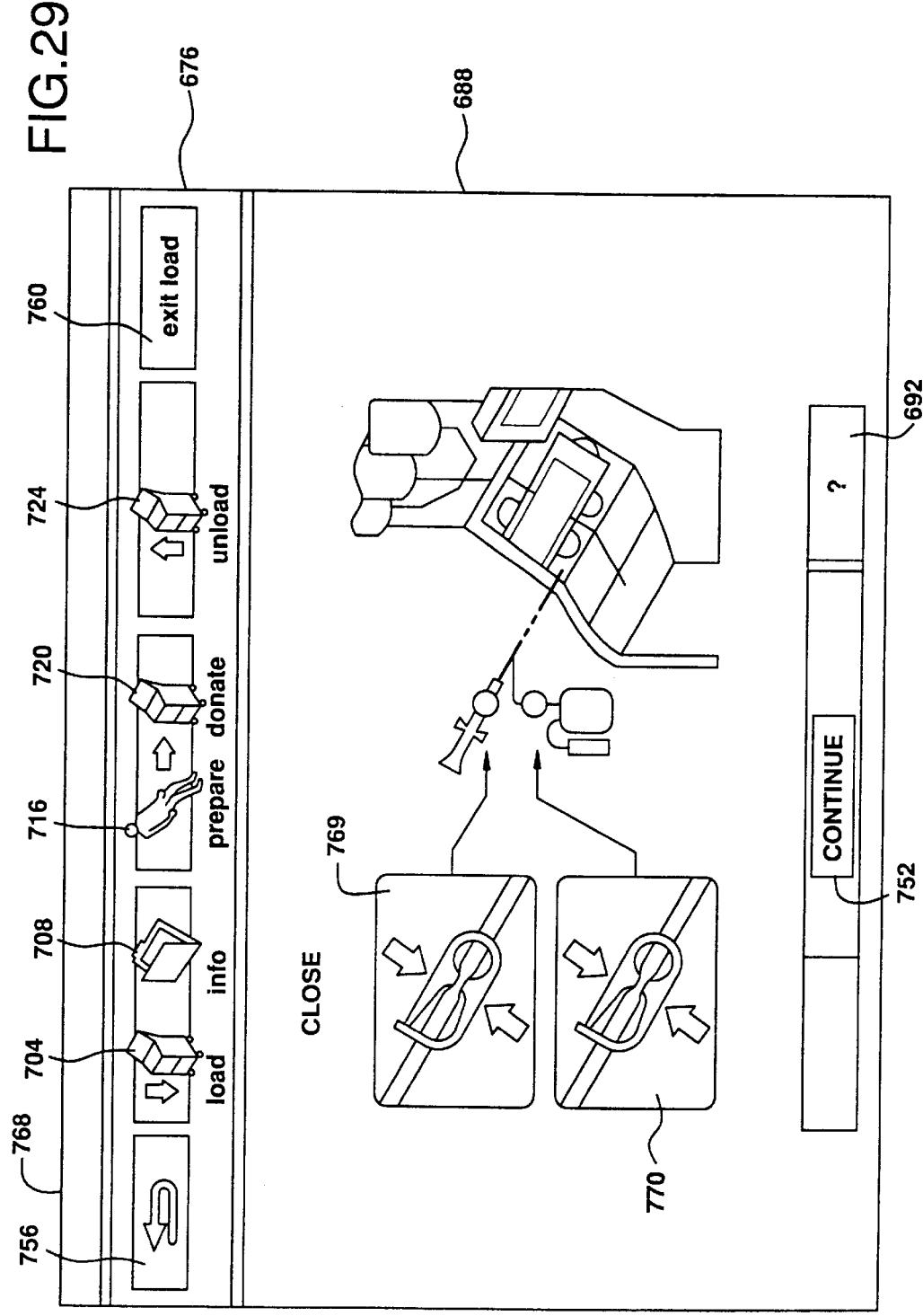
FIG. 29 is a "disposable pressure test screen" for the computer graphics interface of the apheresis system of FIG. 1.
Figure 30:
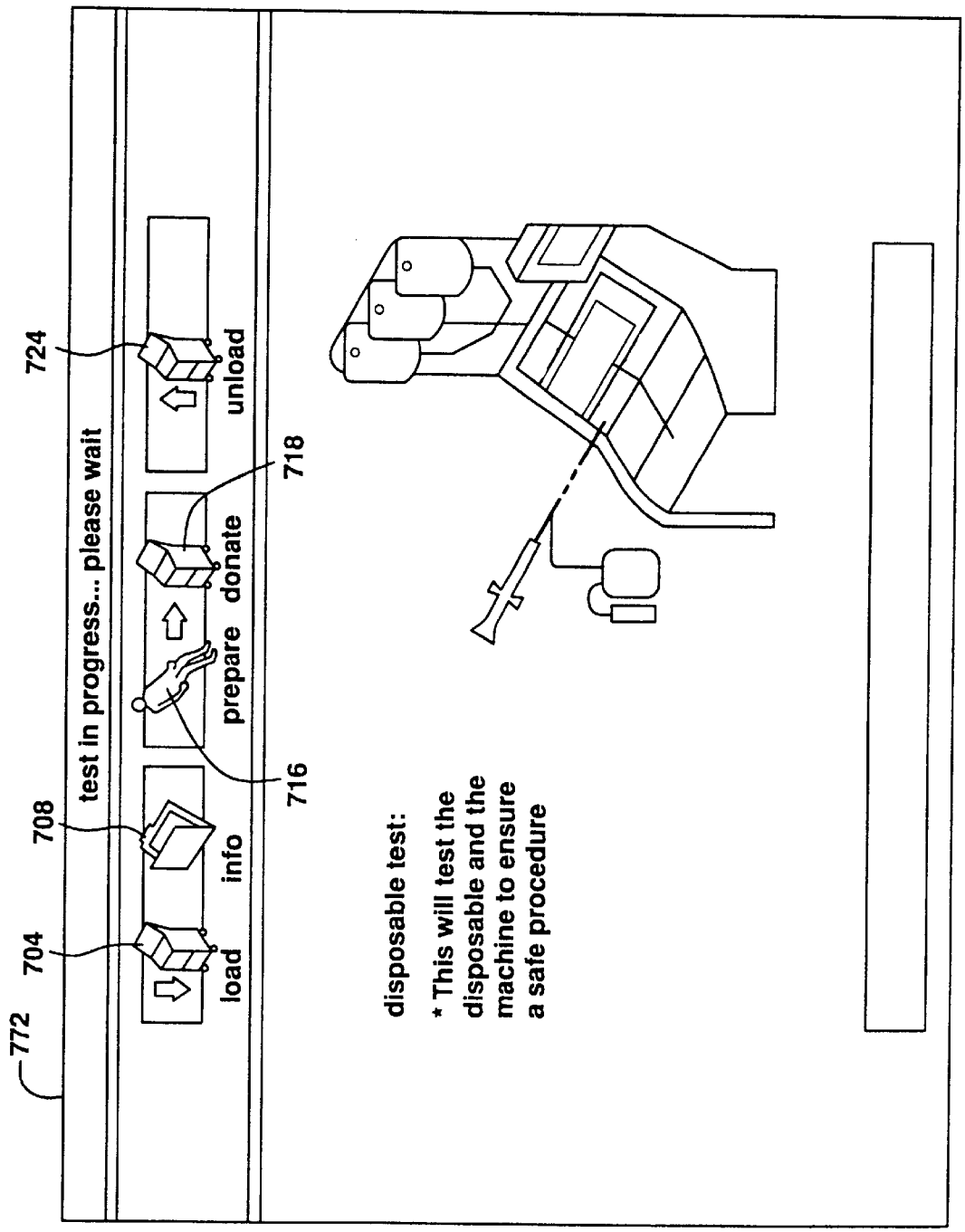
FIG. 30 is a "pressure test in progress screen" for the computer graphics interface of the apheresis system of FIG. 1.

When the operator touches the continue button 752 on the loading procedure screen 732, a disposable pressure test screen 768 is produced on the display 664, one embodiment of which is illustrated in FIG. 29. Generally, the disposable pressure test screen 768 pictorially conveys to the operator that certain steps must be undertaken to allow for pressure testing of the disposable set 8 and how this may be affected by the operator. In this regard, a donor/patient access line clamp pictorial 769 pictorially conveys to the operator that the blood removal/return tubing assembly 20, specifically the interconnect tubing 38, to the donor/patient 4 must be sealed off. A donor/patient sample line clamp pictorial 770 pictorially conveys to the operator that the sample line of the sample subassembly 46 must also be sealed off as well. When the operator has completed these steps, the operator touches the continue button 752 and a test in progress screen 772 is displayed to the operator to pictorially and textually convey to the operator that the testing procedure is underway and such is illustrated in FIG. 30.

Figure 31:
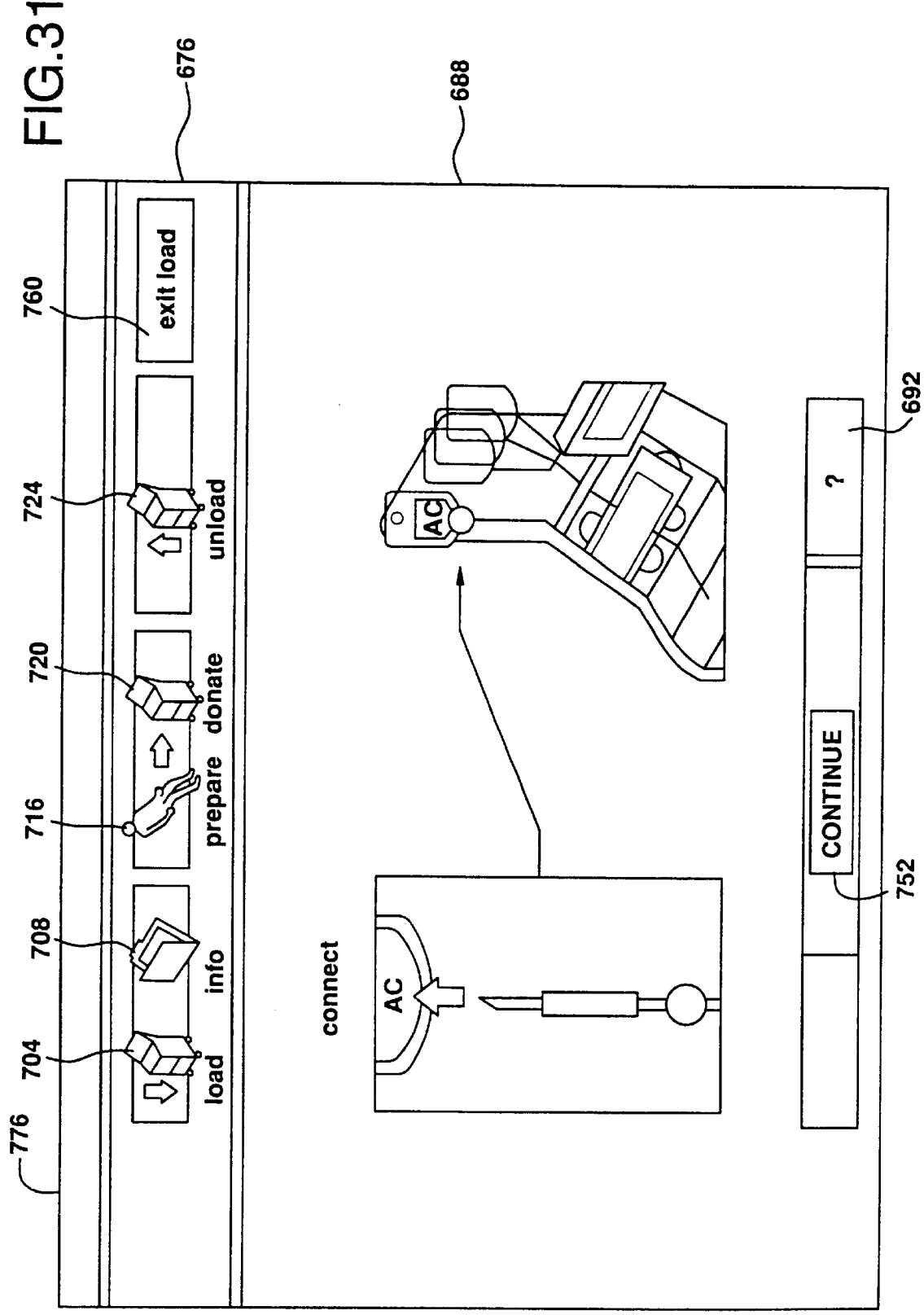
FIG. 31 is a "AC interconnect screen" for the computer graphics interface of the apheresis system of FIG. 1.

After the pressure test of the disposable set 8 is complete, an AC interconnect screen 776 is produced on the display 664 and one embodiment of which is illustrated in FIG. 31. The AC interconnect screen 776 pictorially conveys to the operator that the anticoagulant tubing assembly 50, specifically the spike drip member 52, of the extracorporeal tubing circuit 10 needs to be fluidly interconnected with the AC bag (not shown), as well as generally how this step may be affected by the operator. When this step has been completed by the operator, the operator touches the continue button 752 on the display 664.

Figure 32:
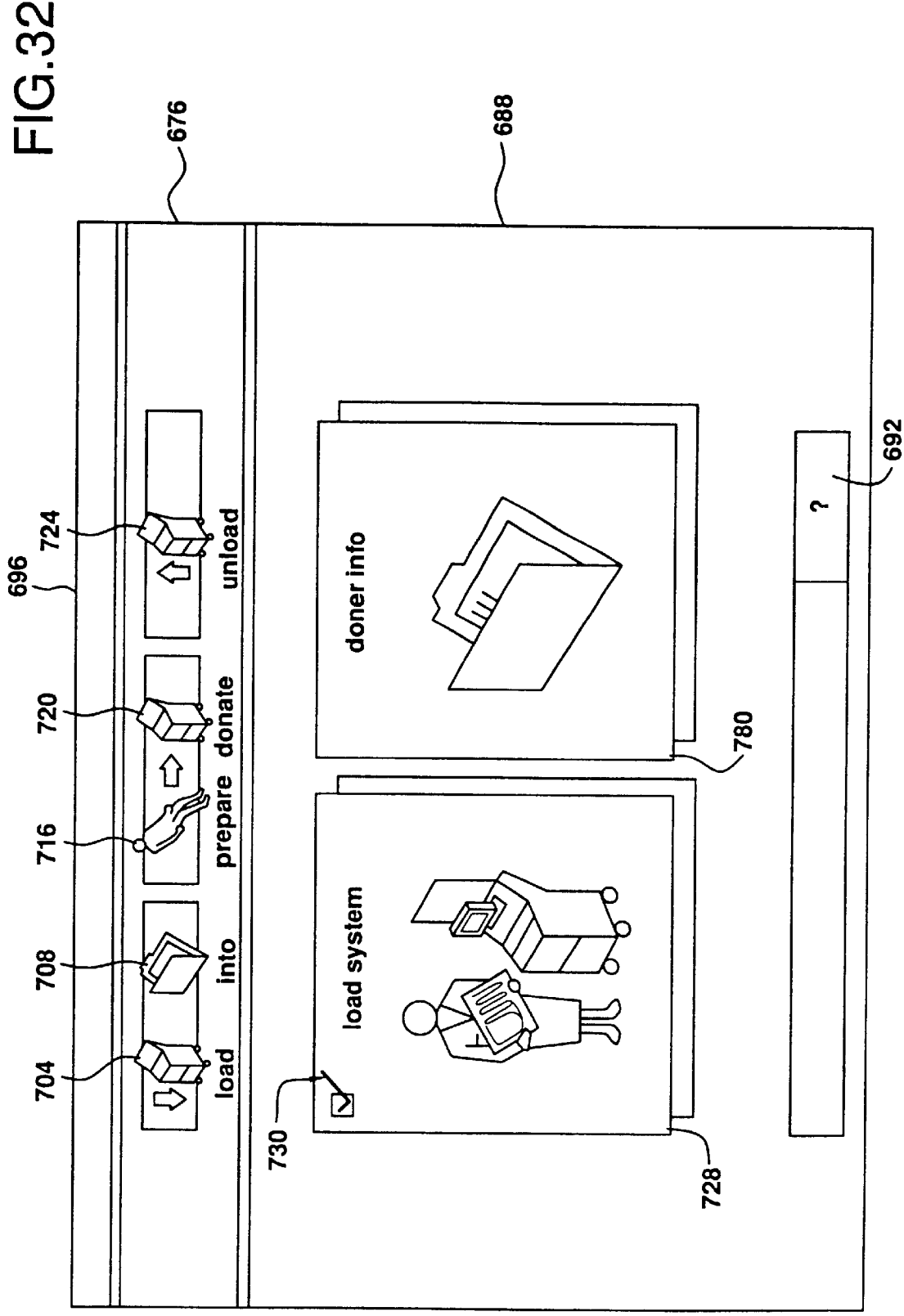
FIG. 32 is the "master screen" of FIG. 26 which has been updated to reflect completion of the loading of the disposables.

The AC interconnect is the last of the steps associated with the load icon 704 such that the operator is returned to the master screen 696. The master screen 696 now reflects the current status of the apheresis procedure and is illustrated in FIG. 32. That is, the color or shade of the load icon 704 is changed from the second color/shade to the third color/shade to that which indicates that all steps associated with the load icon 704 have been completed by the operator. Moreover, a status check 730 appears on the load system button 728 in the work area 688 as well. The load system button 728 is grayed out for the duration of the procedure and thus indicates that the system setup may not be repeated. Consequently, two different types of indications are provided to the operator of the current status regarding the loading procedure. The change in status of the donor/patient data entry portion of the apheresis procedure is also updated by presenting the information icon 708 in the status bar 676 in the second color/shade which indicates to the operator that it is now appropriate to begin this aspect of the apheresis procedure.

Figure 33:
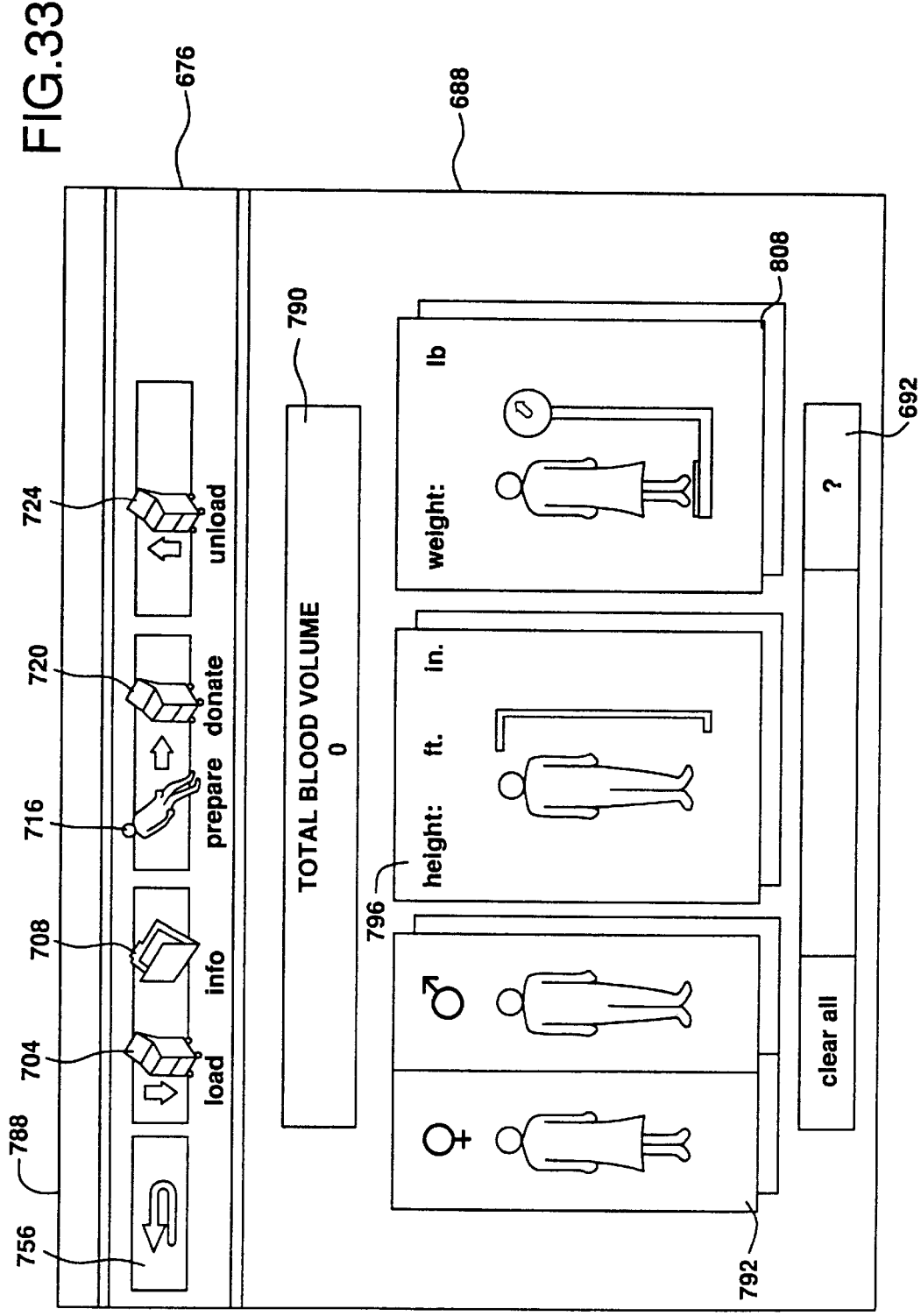
FIG. 33 is a "donor/patient data screen" for the computer graphics interface of the apheresis system of FIG. 1.
Figure 34:
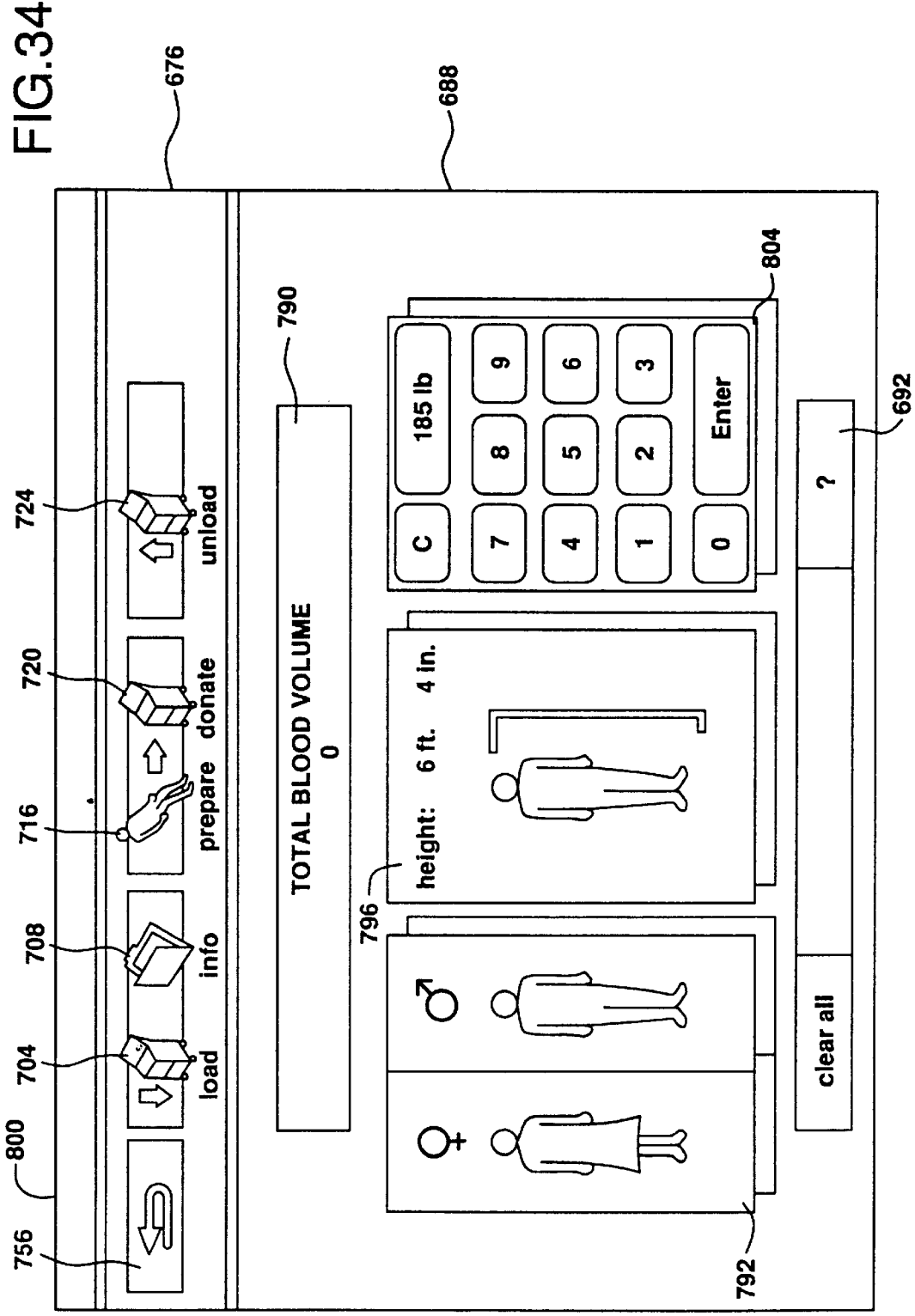
FIG. 34 is a "weight input screen" for the computer graphics interface of the apheresis system of FIG. 1.

The operator enters the information entry portion of the apheresis procedure by touching the info button 780 on the display 664 of the master screen 696. This produces a donor/patient data screen 788 on the display 664, one embodiment of which is illustrated in FIG. 33. The donor/patient data screen 788 which includes a sex-type button 792, a height button 796, and a weight button 808. The operator may indicate the sex of the donor/patient 4 by touching the relevant portion of the split sex-type button 792 and the selected sex may be displayed to the operator (e.g, via color differentiation). Moreover, the operator may enter the height and weight of the donor/patient 4 by touching the height button 796 and the weight button 808, respectively. When the height button 796 and weight button 808 are engaged by the operator, a keypad 804 is superimposed over the button whose information is to be entered as illustrated in FIG. 34. The keypad 804 may be used to enter the donor/patient's 4 height and weight and this information may also be displayed to the operator.

The information entered by the operator on the donor/patient data screen 788 is used to calculate, for instance, the donor/patient's 4 total blood volume which is presented in a total blood volume display 790 on the donor/patient data screen 788. The donor/patient's 4 total blood volume may be utilized in the determination of various parameters associated with the apheresis procedure and/or in the estimation of the numb r of blood components which are anticipated to be collected in the procedure. When the operator has completed these data entry procedures, the operator touches the continue button 752 which will be displayed on the bottom of the donor/patient data screen 788 after all requested information has been input.

Figure 35:
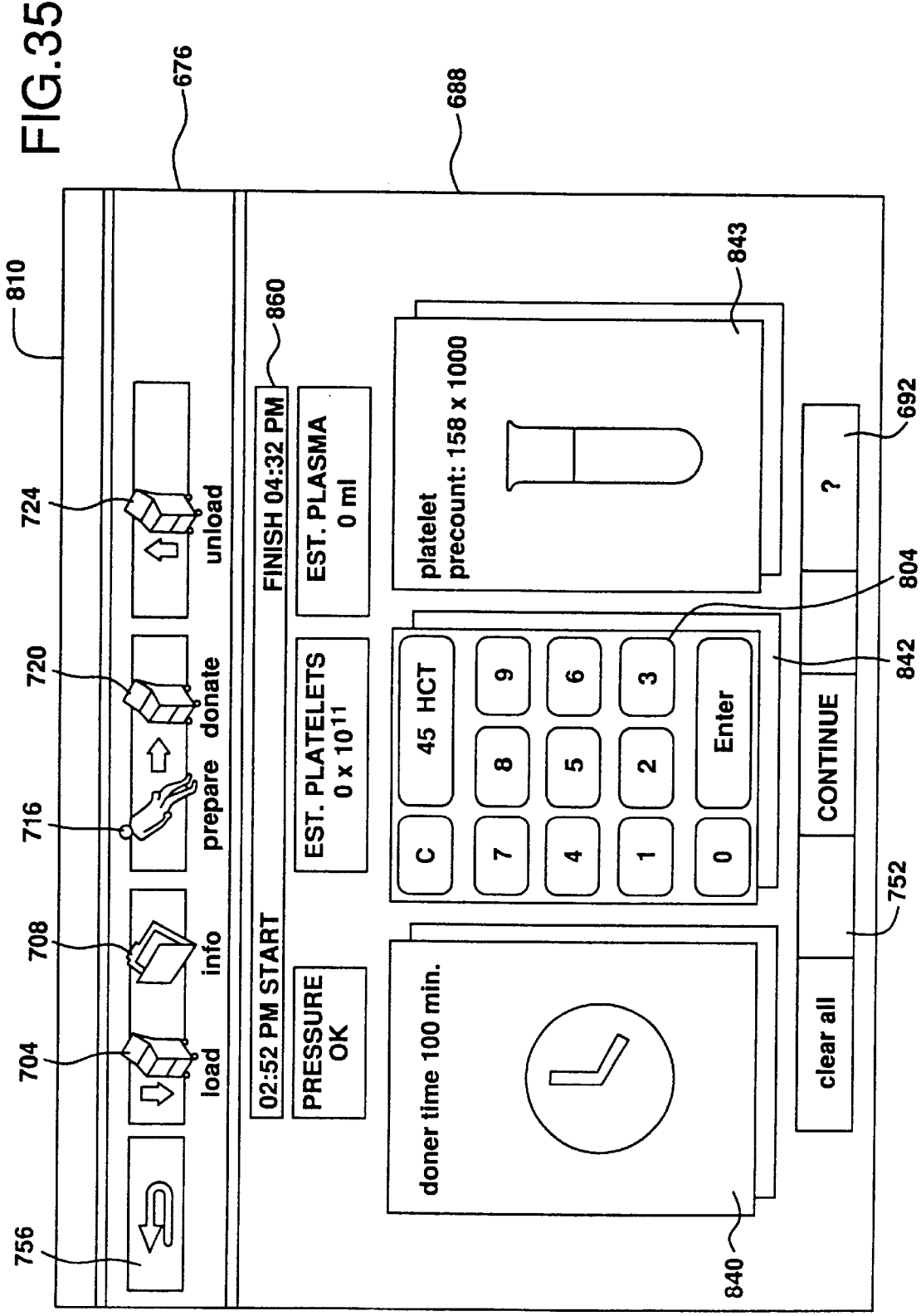
FIG. 35 is a "lab data screen" for the computer graphics interface of the apheresis system of FIG. 1.

A lab data entry screen 810 is generated on the computer display 664 after the steps associated with the donor/patient data screen 788 have been completed and as indicated by the operator, one embodiment of which is illustrated in FIG. 35. The lab data entry screen 810 requests the operator to enter the time for the collection procedure by touching a donation time button 840 which results in the keypad 804 being superimposed over the donation time button 832 (not shown). The donation time entered by the operator will be displayed on a time display 860, which specifies the duration for the procedure. Moreover, the donation time entered by the operator may also be displayed on the donation time button 840. The donation time is used, for instance, to predict the number of the blood component(s) (e.g., platelets, plasma) which is anticipated to be collected during the procedure.

The lab data screen 810 also prompts the operator to enter the donor/patient's 4 hematocrit by touching a hematocrit button 842. This results in the keypad 804 being superimposed over the hematocrit button 842. The operator may then enter the donor/patient's 4 hematocrit (e.g., as determined via laboratory analysis of a blood sample from the donor/patient 4) and such may be displayed on the hematocrit button 842. The donor/patient's 4 hematocrit is also utilized by one or more aspects of the apheresis procedure.

The lab data screen 810 also prompts the operator to enter the donor/patient's 4 platelet precount by touching a platelet precount button 843. This results in the keypad 804 being superimposed over the platelet precount button 843. The operator may then enter the donor/patient's 4 platelet precount (e.g., as determined via laboratory analysis of a blood sample from the donor/patient 4) and such may be displayed on the platelet precount button 843. The donor/patient's 4 platelet precount is also utilized by one or more aspects of the apheresis procedure.

Figure 36:
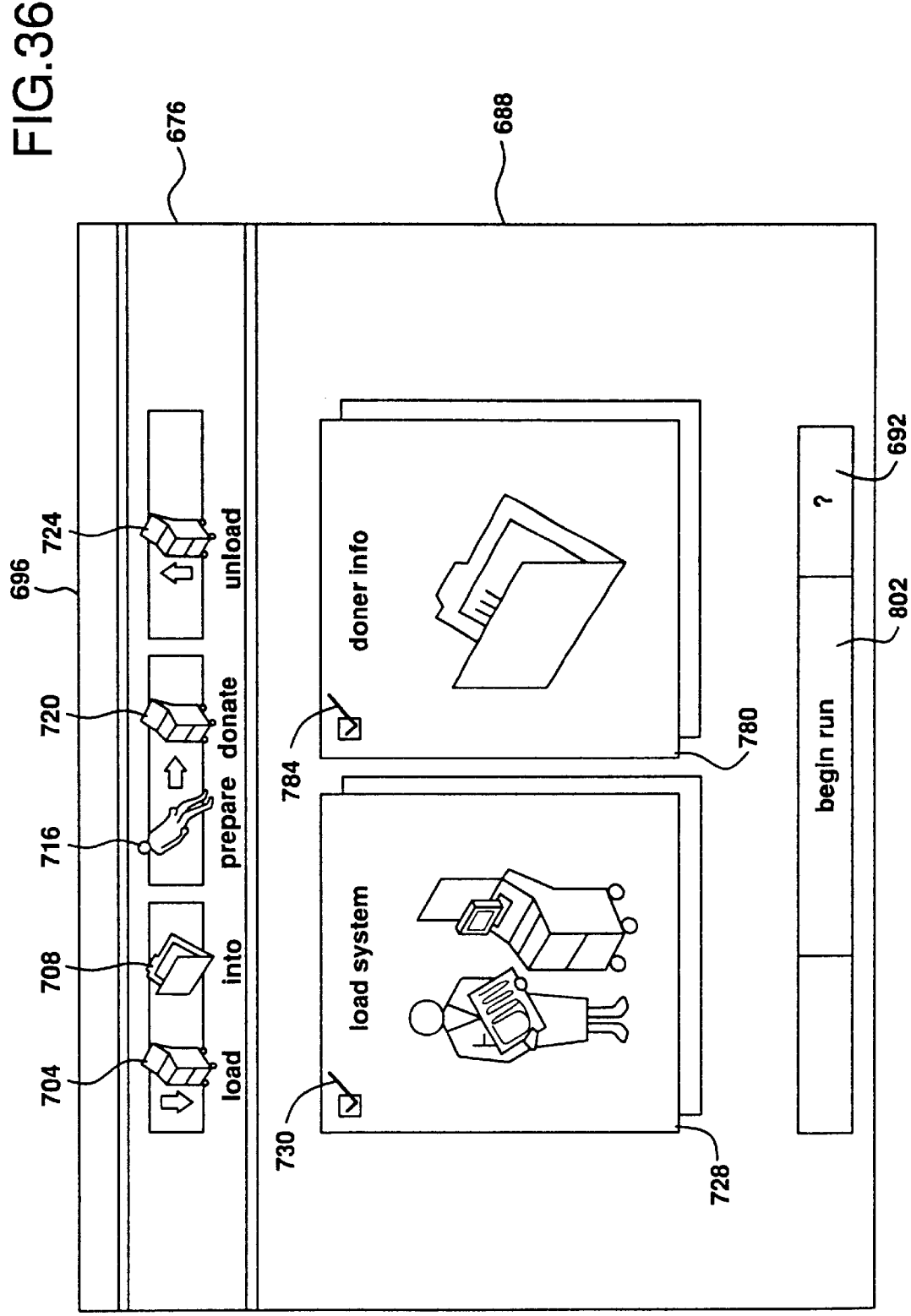
FIG. 36 is the "master screen" of FIG. 26 which as been updated to reflect completion of the donor/patient preps.

Once the operator has entered all of the requested information, the operator touches the continue button 752 which returns the operator to the master screen 696 which now reflects the current status of the apheresis procedure and as illustrated in FIG. 36. Since all of the steps associated with the information icon 708 have now been completed, the color/shade of the information icon 708 is changed from the second color/shade to the third color/shade to convey to the operator that all associated steps have been completed. Moreover, a status check 784 appears on the donor/patient info button 780 in the work area 688 as well. Consequently, two different types of indications are provided to the operator of the current status of this aspect of the apheresis procedure. Moreover, the change in status of the collection icon set 712 of the apheresis procedure is updated by changing the color/shade of the donor/patient prep icon 716 in the status bar 676 from the first color/shade to the second color/shade. A run button 802 is also now presented on the master screen 696 such that the steps associated with the collection icon set 712 may now be undertaken and further such that pictorial representations of the same may be provided to the operator.

Figure 37:
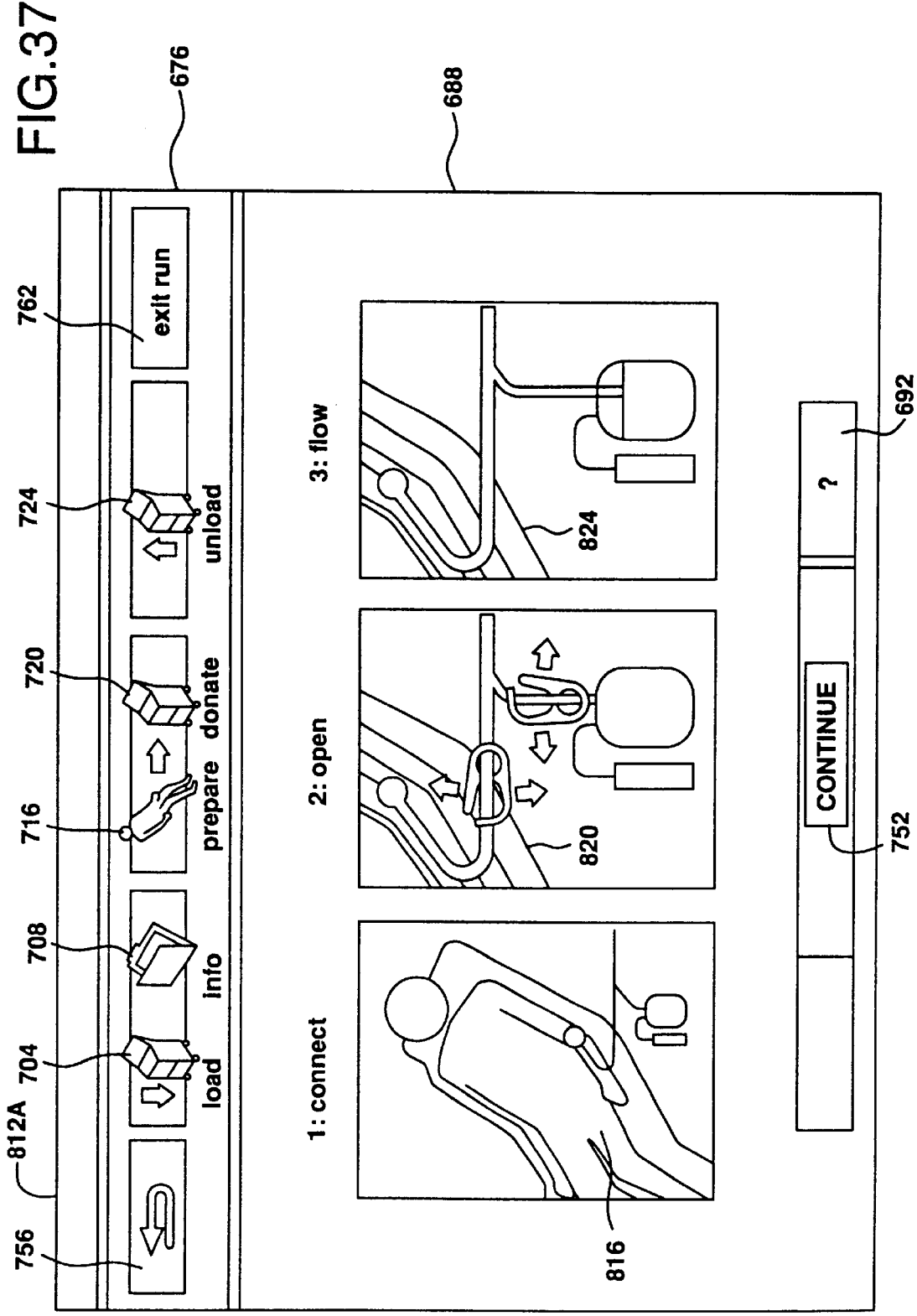
FIG. 37 is a first "donor/patient preps screen" for the computer graphics interface of the apheresis system of FIG. 1.

The initial screen for steps associated with the collection icon set 712 is a donor/patient prep screen 812A which is illustrated in FIG. 37. The donor/patient prep screen 812A pictorially conveys to the operator the steps which must be undertaken in relation to the donor/patient 4 being fluidly interconnected with the blood component separation device. Initially, a donor/patient connect pictorial 816 is displayed which pictorially conveys to the operator that an access needle 32 must be installed on the donor/patient 4, as well as generally how this step may be affected by the operator. The word "CONNECT" is also positioned above the donor/patient connect pictorial 816 to provide a short textual instruction to the operator of the required action(s). The donor/patient connect pictorial 816 is disposed on the left side of the donor/patient prep screen 812A which indicates that this is the first step or substep associated with the donor/patient prep icon 716. In order to provide further indications of the desired order to the operator, the number "1" is also disposed adjacent the word "CONNECT."

The donor/patient prep screen 812A also displays an open pictorial 820 on the display 664. The open pictorial 820 pictorially conveys to the operator that the clamps 42 in the interconnect tubing 38 and the clamp in the tubing of the sample subassembly 46 must be removed, as well as generally how these steps may be affected by the operator. The word "OPEN" is also positioned above the open flow pictorial 820 to provide a short textual instruction to the operator of the required action(s). The open pictorial 820 is disposed to the right of the donor/patient connect pictorial 816 which indicates that the step(s) associated with the open pictorial 820 should be performed only after the step(s) associated with the donor/patient connect pictorial 816 have been completed. In order to provide further indications of the desired order to the operator, the number "2" is also disposed adjacent the word "OPEN."

The donor/patient prep screen 812A also displays a flow pictorial 824 on the display 664. The flow pictorial 824 pictorially conveys to the operator that there should now be a flow of blood from the donor/patient 4 into the blood removal/return tubing assembly 20, specifically the blood removal tubing 22, and in the sample tubing of the sample subassembly 46. The word "FLOW" is also positioned above the flow pictorial 824 to provide a short textual description to the operator of what should be occurring at this time. The flow pictorial 824 is disposed to the right of the open pictorial 820 which indicates that the conditions associated with the flow pictorial 824 should occur only after the step(s) associated with the open pictorial 820 have been completed. In order to provide further indications of the desired order to the operator, the number "3" is also disposed adjacent the word "FLOW."

In summary, the work area 688 of the donor/patient prep screen 812A not only conveys to the operator what type of steps must be performed for this aspect of the apheresis procedure and how to generally perform these steps, but also specifies the order in which these steps should be performed by two methods. Initially, the pictorial graphics 816, 820, and 824 are sequentially displayed in left-to-right fashion. Moreover, the three steps are also numerically identified next to their associated one-word textual description.

Figure 38:
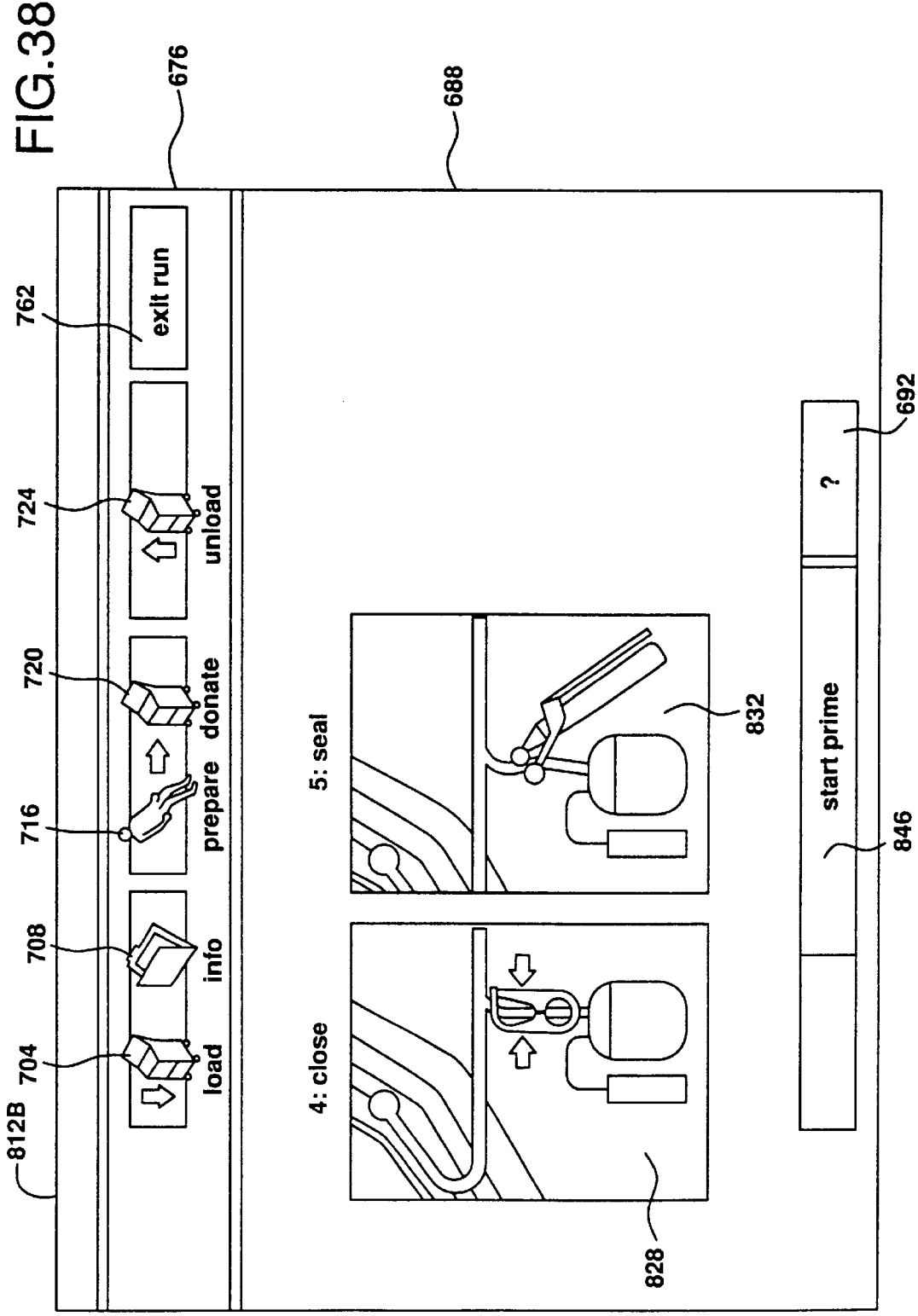
FIG. 38 is a second "donor/patient preps screen" for the computer graphics interface of the apheresis system of FIG. 1.

Once the operator completes all of the steps associated with the donor/patient prep screen 812A, the operator touches the continue button 752 which results in the display of a second donor/patient prep screen 812B as illustrated in FIG. 38. The donor/patient prep screen 812B includes a close pictorial 828 which pictorially conveys to the operator to terminate the flow of blood from the donor/patient 4 to the sample bag of the sample subassembly 46 by clamping the sample line and generally how this step may be affected by the operator. The word "CLOSE" is also positioned above the close pictorial 828 to provide a short textual instruction to the operator of the required action(s). The close pictorial 828 is disposed on the left side of the donor/patient prep screen 812B which indicates that this is the first step or substep associated with the donor/patient prep screen 812B. In order to provide an indication that this is in fact, however, the fourth step associated with the donor/patient preps, the number "4" is also disposed adjacent the word "CLOSE."

The donor/patient prep screen 812B also displays a seal pictorial 832 on the display 664. The seal flow pictorial 832 pictorially conveys to the operator that the sample line of the sample subassembly 46 should now be sealed off and generally how this step may be affected by the operator. The word "SEAL" is also positioned above the seal pictorial 832 to provide a short textual instruction to the operator of the required action(s). The seal pictorial 832 is disposed to the right of the close pictorial 828 which indicates that the step(s) associated with the seal pictorial 832 should be performed only after the step(s) associated with the close pictorial 828 have been completed. In order to provide further indications of the desired order to the operator, the number "5" is also disposed adjacent the word "SEAL" to indicate that this is actually the fifth step associated with the donor/patient preps.

In summary, the work area 688 of the donor/patient prep screen 812B not only conveys to the operator what type of steps must be performed for this aspect of the apheresis procedure and how to generally perform these steps, the work area 688 of the donor/patient prep screen 812B also specifies the order in which these steps should be performed by two methods. Initially, the pictorials 828, 832, and 836 are sequentially displayed in left-to-right fashion. Moreover, the four steps are also numerically identified next to their associated one-word textual description.

Figure 39:
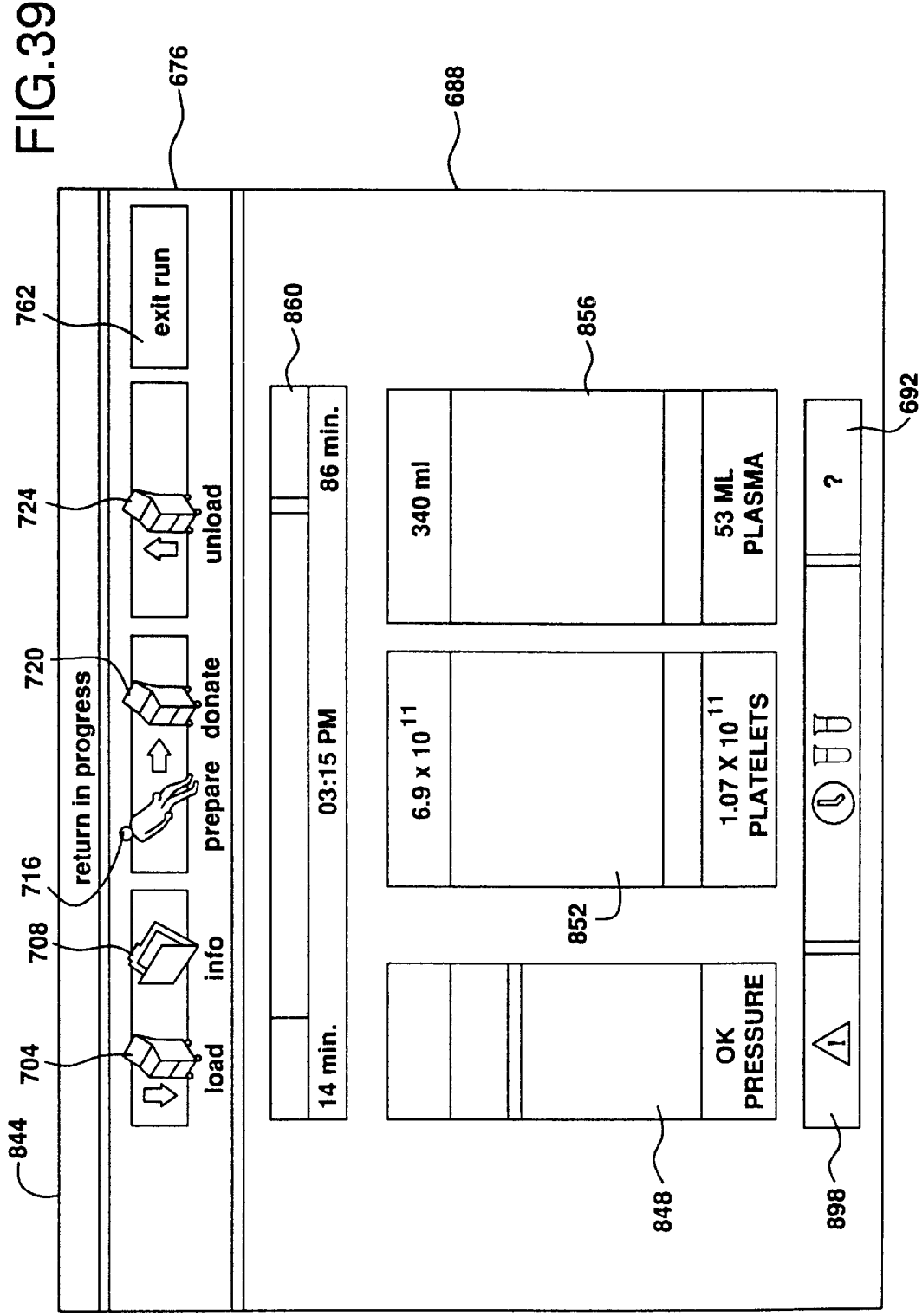
FIG. 39 is a "run screen" for the computer graphics interface of the apheresis system of FIG. 1.

Once the operator completes all of the donor/patient preps, the operator may touch the start prime button 846 on the donor/patient prep screen 812B which initiates the above-described blood prime of the extracorporeal tubing circuit 10 and blood processing vessel 352 and which results in the display of the run screen 844 illustrated in FIG. 39. The run screen 844 primarily displays information to the operator regarding the apheresis procedure. For instance, the run screen 844 includes a blood pressure display 848 (i.e., to convey to the operator the donor/patient's extracorporeal blood pressure), a platelet collect display 852 (i.e., to convey to the operator an estimate of the number of platelets which have been currently collected) a plasma collect display 856 (i.e., to convey to the operator the amount of plasma which has been currently collected), and a time display 860 (e.g., both the amount of time which has lapsed since the start of the collection procedure (the left bar graph and noted time), as well as the amount of time remaining in the collection procedure (the right bar graph and noted time). A control button (not shown) may be provided to toggle between the time remaining display and the start and stop time display.

The run screen 844 may also display, in the case of a single needle procedure (i.e., where only one needle is utilized to fluidly interconnect the donor/patient 4 with the blood component separation device 6), whether blood is being withdrawn from the donor/patient 4 (e.g., by displaying "draw in progress") or is being returned to the donor/patient 4 (e.g., by displaying "return in progress"). This information may be useful to the donor/patient 4 in that if the donor/patient 4 is attempting to maintain a certain blood pressure by squeezing an article to assist in removal of blood from the donor/patient 4, the donor/patient 4 will be provided with an indication to suspend these actions while blood is being returned to the donor/patient 4.

Figure 40:
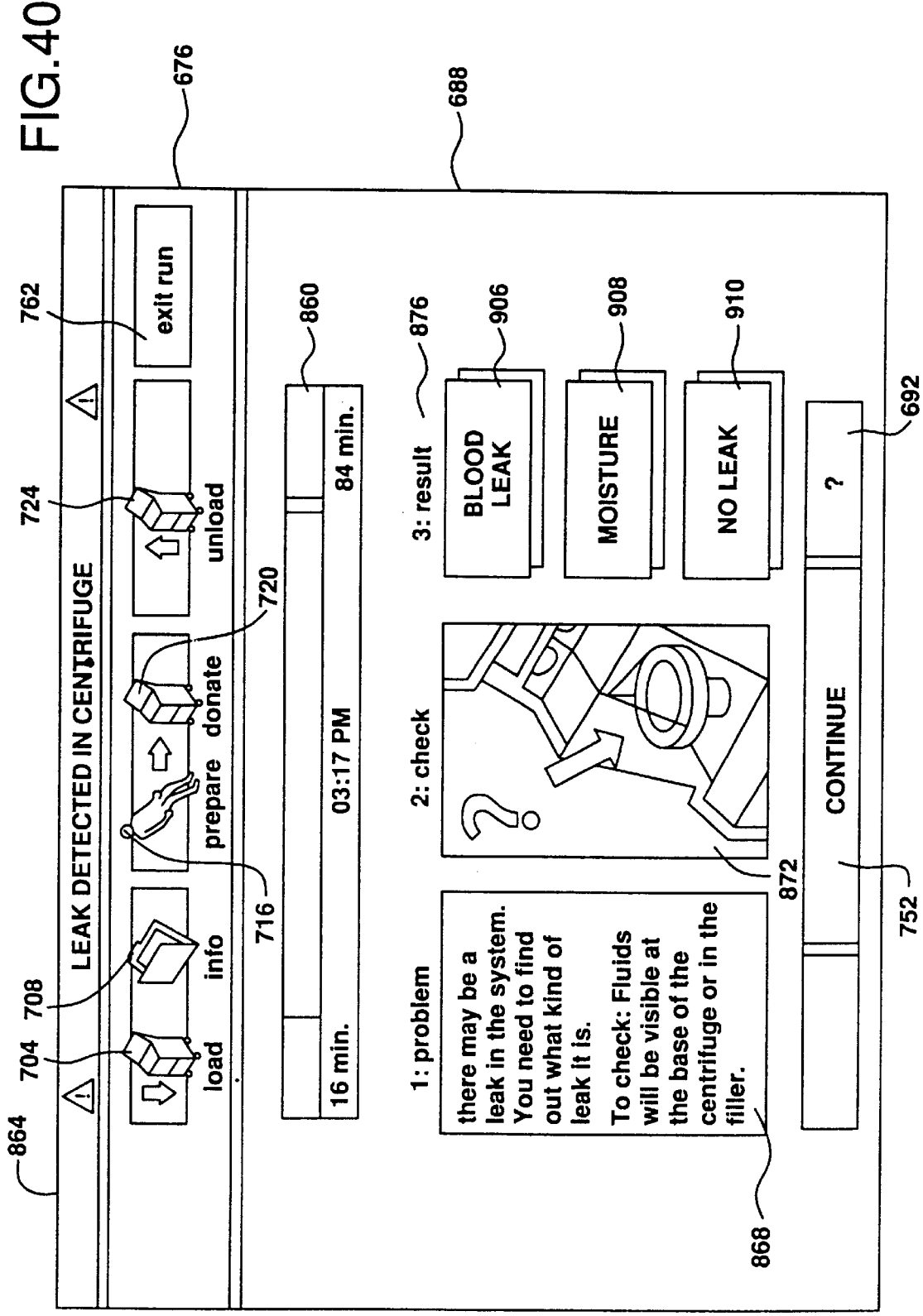
FIG. 40 is one embodiment of an "alarm screen" for the computer graphics interface of the apheresis system of FIG. 1.

During the apheresis procedure, certain conditions may be detected by the apheresis system 2 which would benefit from an investigation by the operator. If one of these types of conditions is detected, an appropriate alarm screen is displayed to the operator. One embodiment of an alarm screen 864 is illustrated in FIG. 40. Initially, the alarm screen 864 textually conveys a potential problem with the system 2 via a problem graphic 868. The text may be useful in ensuring that the operator understands the problem. The alarm screen 864 also includes an action pictorial 872 which graphically conveys to the operator the action which should be taken in relation to the problem. These are actions which may be difficult or impossible for the system 2 to take itself. Finally, the alarm screen includes an inspection results array 876 which allows the operator to indicate the results of the inspection. In the illustrated embodiment, the array 876 includes a blood leak button 906, a moisture button 908, and a no leak button 910.

Depending upon the selection made by the operator on the inspection results array 876, additional questions may be posed to the operator in further screens which require further investigation and/or which specify the desired remedial action. For instance, the supplemental alarm screen 878 of FIG. 41 may be generated by the operator touching the moisture button 908 on the alarm screen 864. The supplemental alarm screen 878 includes a remedial action pictorial 912 and remedial action text 914 to convey to the operator how to correct the identified problem.

The computer interface 660 may also allow the operator to initiate some type of corrective action based upon observations made by and/or conveyed to the operator. For instance, various screens of the interface 660 may include a trouble shooting button 898 which will generate one or more trouble shooting screens. These trouble shooting screens may include menus or the like to allow the operator to indicate what type of potential problem exists. One embodiment of a trouble shooting screen 880 is presented in FIG. 42. The trouble shooting screen 880 includes a donor/patient tingling button 922. This button 922 would be utilized by the operator to attempt to remedy the effects of AC on the donor/patient 4 in response to the donor/patient indicating a "tingling sensation" or, alternatively, "AC reaction." When the operator hits the "down arrow" of the donor/patient tingling button 922, the system 2 attempts to correct the condition in a predetermined manner (i.e., a predetermined protocol is employed preferably this protocol does not require operator actions or decisions). Once the tingling sensation no longer exists, the operator may use the "up arrow" button to return the bar on the donor/patient tingling button 922 to its original position.

The trouble shooting screen 880 also includes a clumping button 924. This button 924 would be utilized by the operator if any undesired clumping of the collected product (e.g., platelets) was observed. When the operator hits the "down arrow" of the clumping button 924, the system 2 attempts to correct the condition in a predetermined manner (i.e., a predetermined protocol is employed and preferably this protocol does not require operator actions or decisions). Once the clumping is no longer observed by the operator, the operator may use the "up arrow" button to return the bar on the clumping button 924 to its original position.

The trouble shooting screen 880 may also include a spillover button 916 and an "air in plasma line" button 918. The spillover button 916 would be engaged by the operator if red blood cells were observed in the platelet outlet tubing 66, in the platelet collect bag 84, and/or flowing beyond the RBC dam 232. Activation of the spillover button 916 via the touch screen capabilities would result in the system 2 using a predetermined and preferably automatic protocol is performed by the system 2 to correct this condition. Similarly, if the operator observes air in the plasma line 918 and engages the button 918, the system 2 again will preferably automatically employ a predetermined protocol to correct this condition.

The "other problem button" 920 may be utilized to generate further trouble shooting screens to list further problems which may occur in the apheresis procedure. Again, preferably upon the operator touching the associated button indicative of a particular problem, a predetermined protocol will be preferably automatically employed to attempt to correct the same.

Upon completion of the collection portion of the apheresis procedure, the rinseback screen 884 is produced on the display 664 which indicates that the rinseback procedure will now be performed and which is illustrated in FIG. 44. Once the rinseback is completed, the color/shade of the donate icon 720 changes from the second color to the third color/shade to indicate that all steps associated with this aspect of the apheresis procedure have been completed. Moreover, the color/shade of the unload icon 724 will also change from the first color/shade to the second color/shade to indicate to the operator that the step(s) associated therewith may now be performed.

Upon completion of the rinseback, a run finish screen may be produced on the display 664 to provide the final collection data as illustrated in FIG. 43 (e.g., the associated yields of platelets and plasma collected during the procedure) as well as the fact that the procedure is over (e.g., by displaying "run completed"). The operator may then touch the continue button 752.

Once the rinseback procedure is completed, an unload screen 892 will be presented on the display 664 and is illustrated in FIG. 45. The unload screen 892 may sequentially display a number of pictorials to the operator to convey the steps which should be completed to terminate the procedure. For instance, a seal/detach pictorial 900 may be initially displayed on the unload screen 892 to pictorially convey to the operator that the tubes leading to the platelet and plasma collect bag (s) 84, 94 should each be sealed such that the platelet and plasma collect bag (s) 84, 94 respectively, may be removed. Once the operator touches the continue button 752, a disconnect pictorial 902 may be presented on the unload screen 892 to pictorially convey to the operator that the access needle 32 should be removed from the donor/patient 4. Once the operator touches the continue button 752, a remove pictorial 904 is presented on the unload screen 892 to pictorially convey to the operator that the disposable set 8 should be removed from the blood component separation device 6 and disposed of properly.

The computer interface 660 provides a number of advantages. For instance, the computer interface 660 utilizes a three-way color/shade differentiation to conveniently convey the status of the apheresis procedure to the operator. An icon is presented in one color/shade if the step(s) associated with the icon are not yet ready to be performed, while the icon is presented in another color/shade if the step(s) associated with the icon are ready to be performed or are being performed, while the icon is presented in yet another color/shade if the step(s) associated with the icon have been completed. Moreover, the computer interface 660 provides pictorials to the operator of at least certain of the steps of the apheresis procedure. Furthermore, the desired/required ordering of at least the fundamental steps of the apheresis procedure is conveyed to the operator. Finally, the interface 660 allows for correction of certain conditions, which after appropriate operator input, are remedied by the system 2 in accordance with a predetermined protocol.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A disposable assembly for use in an extracorporeal blood processing system comprising:

a single needle for removal of whole blood from a donor and return of uncollected blood components to a donor;

a blood removal conduit fluidly interconnected to said single needle for transferring said whole blood from a donor;

a blood return conduit fluidly interconnected to said single needle for transferring said uncollected blood components;

a fluid reservoir interconnected to said blood removal and blood return conduits for accumulating and disposing of said uncollected blood components; and a gas holder interconnected to said fluid reservoir for receiving gas from said fluid reservoir as said fluid reservoir accumulates uncollected blood components and returning said gas to said fluid reservoir as said fluid reservoir disposes of uncollected components.

2. A disposable assembly as claimed in claim 1, further comprising:

a molded cassette member, wherein said fluid reservoir, a portion of said blood removal conduit and a portion of said blood return conduit are each integrally defined within said molded cassette member.

3. A disposable assembly as claimed in claim 1, wherein:

said gas holder comprises a flexible bag and a flexible tubing interconnecting said flexible bag and said fluid reservoir.

4. A disposable assembly as claimed in claim 1, further comprising:

a plurality of blood component conduits fluidly interconnected to said fluid reservoir for separately transferring uncollected blood components thereto.

5. A disposable assembly as claimed in claim 4, further comprising:

at least one blood component collector fluidly interconnected to a corresponding one of said blood component conduits.

6. A disposable assembly as claimed in claim 1, wherein said gas comprises air.

7. A disposable assembly as claimed in claim 1, wherein said gas is sterile.

8. A disposable assembly as claimed in claim 1, further comprising:

a blood separation device interconnected to said fluid reservoir wherein gas is vented from said blood separation device to said gas holder via said fluid reservoir.

9. A disposable for use in an extracorporeal blood processing system comprising:
- a single needle for removal of whole blood from a donor and return of uncollected blood components to a donor;
- a blood removal conduit fluidly interconnected to said single needle for transferring said whole blood from a donor;
- a blood return conduit fluidly interconnected to said single needle for transferring said uncollected blood components;
- a fluid reservoir interconnected to said blood removal and blood return conduits for accumulating and disposing of said uncollected blood components; and
- an air holder interconnected to said fluid reservoir for receiving air from said fluid reservoir as said fluid reservoir accumulates uncollected blood components and returning said air to said fluid reservoir as said fluid reservoir disposes of uncollected components.

10. A disposable assembly as claimed in claim 9, wherein:
said air holder comprises a flexible bag and a flexible tubing interconnecting said flexible bag and said fluid reservoir.

11. A disposable assembly as claimed in claim 9, further comprising a molded cassette member, wherein said fluid reservoir and a portion of said blood removal and blood return conduits are each integrally defined within said molded cassette member.

12. A disposable assembly as claimed in claim 9, further comprising:
- a plurality of blood component conduits fluidly interconnected to said fluid reservoir for separately transferring uncollected blood components thereto.

* * * * *